(12) United States Patent
Wucherpfennig et al.

(10) Patent No.: US 10,793,633 B2
(45) Date of Patent: Oct. 6, 2020

(54) THERAPEUTIC PEPTIDES

(71) Applicant: Dana-Farber Cancer Institute, Inc., Boston, MA (US)

(72) Inventors: Kai W. Wucherpfennig, Brookline, MA (US); Bettina Franz, Orem, UT (US); Kenneth F. May, Jr., Bozeman, MT (US); Glenn Dranoff, Sudbury, MA (US); F. Stephen Hodi, Framingham, MA (US); Christopher Harvey, Boston, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 498 days.

(21) Appl. No.: 15/211,758

(22) Filed: Jul. 15, 2016

(65) Prior Publication Data

US 2017/0008962 A1    Jan. 12, 2017

Related U.S. Application Data

(60) Division of application No. 14/025,573, filed on Sep. 12, 2013, now Pat. No. 9,402,905, which is a continuation of application No. PCT/US2012/057839, filed on Sep. 28, 2012.

(60) Provisional application No. 61/541,921, filed on Sep. 30, 2011.

(51) Int. Cl.

| | |
|---|---|
| *A61K 39/00* | (2006.01) |
| *A61K 39/395* | (2006.01) |
| *C07K 16/28* | (2006.01) |
| *C07K 16/06* | (2006.01) |
| *C07K 16/12* | (2006.01) |
| *C07K 16/22* | (2006.01) |
| *A61K 45/06* | (2006.01) |
| *A61K 31/365* | (2006.01) |
| *A61K 31/325* | (2006.01) |
| *A61K 31/16* | (2006.01) |

(52) U.S. Cl.
CPC ...... *C07K 16/2833* (2013.01); *A61K 39/3955* (2013.01); *A61K 45/06* (2013.01); *C07K 16/06* (2013.01); *C07K 16/1282* (2013.01); *C07K 16/22* (2013.01); *A61K 31/16* (2013.01); *A61K 31/325* (2013.01); *A61K 31/365* (2013.01); *A61K 39/39558* (2013.01); *C07K 2317/10* (2013.01); *C07K 2317/21* (2013.01); *C07K 2317/565* (2013.01); *C07K 2317/73* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 4,816,567 A | 3/1989 | Cabilly et al. |
| 5,122,464 A | 6/1992 | Wilson et al. |
| 5,225,539 A | 7/1993 | Winter |
| 5,530,101 A | 6/1996 | Queen et al. |
| 5,545,403 A | 8/1996 | Page |
| 5,545,405 A | 8/1996 | Page |
| 5,545,806 A | 8/1996 | Lonberg et al. |
| 5,545,807 A | 8/1996 | Surani et al. |
| 5,569,825 A | 10/1996 | Lonberg et al. |
| 5,585,089 A | 12/1996 | Queen et al. |
| 5,591,639 A | 1/1997 | Bebbington |
| 5,624,821 A | 4/1997 | Winter et al. |
| 5,625,126 A | 4/1997 | Lonberg et al. |
| 5,633,425 A | 5/1997 | Lonberg et al. |
| 5,648,260 A | 7/1997 | Winter et al. |
| 5,658,759 A | 8/1997 | Bebbington |
| 5,661,016 A | 8/1997 | Lonberg et al. |
| 5,677,425 A | 10/1997 | Bodmer et al. |
| 5,693,762 A | 12/1997 | Queen et al. |
| 5,714,350 A | 2/1998 | Co et al. |
| 5,766,886 A | 6/1998 | Studnicka et al. |
| 5,869,046 A | 2/1999 | Presta et al. |
| 5,939,598 A | 8/1999 | Kucherlapati et al. |
| 5,981,216 A | 11/1999 | Kenten et al. |
| 5,998,144 A | 12/1999 | Reff et al. |

(Continued)

FOREIGN PATENT DOCUMENTS

| | | |
|---|---|---|
| CN | 102911270 A | 2/2013 |
| EP | 0 154 316 A2 | 9/1985 |

(Continued)

OTHER PUBLICATIONS

MacCallum et al (J. Mol. Biol. (1996) 262, 732-745) (Year: 1996).*
Vajdos et al (JMB, 2002 320, 415-428) (Year: 2002).*
Wu et al (J. Mol. Biol. 1999, 294, 151-162) (Year: 1999).*
Edwards et al (JMB, 2003, 334: 103-118) (Year: 2003).*
Lloyd et al (Protein Engineering, Eng. Design & Selection, 2009, 22(3): 159-168) (Year: 2009).*
Goel et al (J. Immunol., 2004, 173: 7358-7367) (Year: 2004).*
Khan and Salunke (J. Immunol, 2014, 192: 5398-5405) teach (Year: 2014).*
Poosarla et al (Biotechn. Bioeng., 2017, 114(6): 1331-1342) (Year: 2017).*

(Continued)

*Primary Examiner* — G. R. Ewoldt
*Assistant Examiner* — Marianne DiBrino
(74) *Attorney, Agent, or Firm* — Baker Donelson

(57) ABSTRACT

The present disclosure provides, in part, compositions comprising peptides that immunospecifically bind to a defined binding partner, such as MHC class I polypeptide-related sequence A (MICA), or an epitope thereon. In some embodiments, the peptides comprise one or more complementarity determining regions relating to the complementarity regions shown in Table 1. The disclosure also provides methods of treating cancer in a subject using the compositions disclosed herein, and methods of isolating human antibodies from cancer patients following immunotherapy.

3 Claims, 40 Drawing Sheets

Specification includes a Sequence Listing.

(56) References Cited

U.S. PATENT DOCUMENTS

| | | | |
|---|---|---|---|
| 6,075,181 A | 6/2000 | Kucherlapati et al. | |
| 6,091,001 A | 6/2000 | Jakobovits et al. | |
| 6,114,598 A | 9/2000 | Kucherlapati et al. | |
| 6,121,022 A | 9/2000 | Presta et al. | |
| 6,165,745 A | 12/2000 | Ward et al. | |
| 6,180,370 B1 | 1/2001 | Queen et al. | |
| 6,194,551 B1 | 2/2001 | Idusogie et al. | |
| 6,277,375 B1 | 8/2001 | Ward | |
| 6,344,203 B1 | 2/2002 | Sandrin et al. | |
| 6,350,861 B1 | 2/2002 | Co et al. | |
| 6,737,056 B1 | 5/2004 | Presta | |
| 7,317,091 B2 | 1/2008 | Lazar et al. | |
| 7,771,718 B2 | 8/2010 | Spies et al. | |
| 7,959,916 B2 | 6/2011 | Spies et al. | |
| 8,101,720 B2 | 1/2012 | Lazar et al. | |
| 8,182,809 B1 | 5/2012 | Wu | |
| 9,402,905 B2 * | 8/2016 | Wucherpfennig | C07K 16/06 |
| 10,106,611 B2 | 10/2018 | Wucherpfennig et al. | |
| 10,279,021 B2 | 5/2019 | Dranoff et al. | |
| 2003/0022450 A1 | 1/2003 | Pan et al. | |
| 2003/0099647 A1 | 5/2003 | Deshpande et al. | |
| 2003/0118592 A1 | 6/2003 | Ledbetter et al. | |
| 2003/0133939 A1 | 6/2003 | Ledbetter et al. | |
| 2003/0153043 A1 | 8/2003 | Carr et al. | |
| 2003/0165835 A1 | 9/2003 | Spies et al. | |
| 2004/0067503 A1 | 4/2004 | Tan et al. | |
| 2004/0115198 A1 | 6/2004 | Spies et al. | |
| 2005/0053608 A1 | 3/2005 | Weber et al. | |
| 2005/0059087 A1 | 3/2005 | Weber et al. | |
| 2005/0158307 A1 | 7/2005 | Spies et al. | |
| 2005/0233391 A1 | 10/2005 | Spies et al. | |
| 2006/0024297 A1 | 2/2006 | Wood et al. | |
| 2006/0228349 A1 | 10/2006 | Acton et al. | |
| 2006/0246071 A1 | 11/2006 | Green et al. | |
| 2007/0248607 A1 | 10/2007 | Spies et al. | |
| 2008/0095803 A1 | 4/2008 | Mekalanos | |
| 2008/0148432 A1 | 6/2008 | Abad | |
| 2009/0022644 A1 | 1/2009 | Sweredjuk | |
| 2009/0175821 A1 | 7/2009 | Bridon et al. | |
| 2009/0226447 A1 | 9/2009 | Boone et al. | |
| 2009/0252729 A1 | 10/2009 | Farrington et al. | |
| 2010/0111973 A1 | 5/2010 | Dranoff et al. | |
| 2010/0189711 A1 | 7/2010 | Dranoff et al. | |
| 2010/0261269 A1 | 10/2010 | June et al. | |
| 2011/0060120 A1 | 3/2011 | Obeid | |
| 2011/0311561 A1 | 12/2011 | Martin, Jr. et al. | |
| 2012/0100182 A1 | 4/2012 | Mooney | |
| 2012/0315287 A1 | 12/2012 | Wu | |
| 2013/0202707 A1 | 8/2013 | Ali et al. | |
| 2014/0004112 A1 | 1/2014 | Wucherpfennig et al. | |
| 2014/0027630 A1 | 1/2014 | Musselman | |
| 2014/0037630 A1 | 2/2014 | Dranoff et al. | |
| 2015/0071862 A1 | 3/2015 | Sabatino et al. | |
| 2016/0027305 A1 | 1/2016 | Inabu et al. | |
| 2016/0046716 A1 | 2/2016 | Wucherpfennig et al. | |
| 2017/0000867 A1 | 1/2017 | Dranoff et al. | |
| 2017/0022275 A1 | 1/2017 | Wucherpfennig et al. | |
| 2017/0198054 A1 | 7/2017 | Harvey et al. | |

FOREIGN PATENT DOCUMENTS

| | | |
|---|---|---|
| EP | 0 401 384 A1 | 12/1990 |
| EP | 1 176 195 A1 | 1/2002 |
| EP | 2336180 A1 | 6/2011 |
| JP | 2008-543774 A | 12/2008 |
| WO | WO 88/07054 A1 | 3/1988 |
| WO | WO 88/08089 A1 | 10/1988 |
| WO | WO 91/10741 A1 | 7/1991 |
| WO | WO 94/02602 A1 | 2/1994 |
| WO | WO 94/29351 A1 | 12/1994 |
| WO | WO 96/32478 A1 | 10/1996 |
| WO | WO 96/33735 A1 | 10/1996 |
| WO | WO 97/34631 A1 | 9/1997 |
| WO | 98/19167 A2 | 5/1998 |
| WO | WO 98/24893 A2 | 6/1998 |
| WO | WO 99/051642 A1 | 10/1999 |
| WO | WO 99/54342 A1 | 10/1999 |
| WO | WO 00/42072 A2 | 7/2000 |
| WO | WO 01/58957 A2 | 8/2001 |
| WO | WO 02/06919 A2 | 1/2002 |
| WO | 02/068615 A2 | 9/2002 |
| WO | WO 03/035835 A2 | 5/2003 |
| WO | WO 03/041600 A1 | 5/2003 |
| WO | WO 2003/074679 A2 | 9/2003 |
| WO | 03/089616 A2 | 10/2003 |
| WO | WO 2004/016750 A2 | 2/2004 |
| WO | WO 2004/029207 A2 | 4/2004 |
| WO | WO 2004/035752 A2 | 4/2004 |
| WO | WO 2004/063351 A2 | 7/2004 |
| WO | WO 2004/074455 A2 | 9/2004 |
| WO | WO 2004/099249 A2 | 11/2004 |
| WO | WO 2005/040217 A2 | 5/2005 |
| WO | WO 2005/070963 A1 | 8/2005 |
| WO | WO 2005/092925 A2 | 10/2005 |
| WO | WO 2006/020114 A2 | 2/2006 |
| WO | WO 2006/068953 A2 | 6/2006 |
| WO | WO 2006/133396 A2 | 12/2006 |
| WO | 2007/055926 A1 | 5/2007 |
| WO | WO 2007/055926 A1 | 5/2007 |
| WO | 2008/036981 A1 | 3/2008 |
| WO | WO 2010/069532 A1 | 6/2010 |
| WO | WO 2011/014469 A1 | 2/2011 |
| WO | WO 2011/063336 A2 | 5/2011 |
| WO | WO 2013/049517 A2 | 4/2013 |
| WO | 2013/117647 A1 | 8/2013 |
| WO | WO 2014/144791 A2 | 9/2014 |

OTHER PUBLICATIONS

Torres and Casadevall (Trend. Immunol., 2008, 29(2): 91-97) (Year: 2008).*

Spear et al (Cancer Immunity, 2013, 13: 1-14) (Year: 2013).*

Zwirner et al (Immunologia, 2006, 25: 25-38) (Year: 2006).*

Justus et al (J. Translational Medicine, 2017, 15: 204, pp. 1-14) (Year: 2017).*

Mei et al., "Expression of NKG2D ligands in multidrug-resistant nasopharyngeal carcinoma cell line CNE2/DDP and their effects on cytotoxicity of natural killer cells," Nan Fang Yi Ke Da Xue Xue Bao.,27 (6):887-889 (2007).

Nausch et al., "NKG2D ligands in tumor immunity," Oncogene, 27: 5944-5958 (2008).

Nelson et al., "Cancer cells engineered to secrete granulocyte-macrophage colony-stimulating factor using ex vivo gene transfer as vaccines for the treatment of genitourinary malignancies," Cancer Chemother. Pharmacol., 46 (Suppl.): S67-72 (2000).

Pantazes, R.J. et al., "OptCDR: a general computational method for the design of antibody complementaritydetermining regions for targeting epitope binding," Protein Engineering, Design & Selection, vol. 23 (11 ), pp. 849-858 (2010).

Pende et al.,"Major histocompatibility complex class I-related chain A and UL16-binding protein expression on tumor cell lines of different histotypes: analysis of tumor susceptibility to NKG2D-dependent natural killer cell cytotoxicity," Cancer Res., 62 (21): 6178-6186 (2002).

Pettersen et al., "CD47 signals T cell death," J. Immunol., 162 (12): 7031-7040 (1999).

Phumyen, A. et al., "Improved Binding Activity of Antibodies Against Major Histocompatibility Complex Class I Chain-Related Gene A by Phage Display Technology for Cancer-Targeted Therapy," Journal of Biomedicine and Biotechnology, vol. 2012(597647) 8 pages, (2012).

Ponsel, Dirk et al., "High Affinity, Developability and Functional Size: The Holy Grail of Combinatorial Antibody Library Generation," Molecules, vol. 16:, pp. 3675-3700 (2011).

Rader, C. et al., "A Phage Display Approach for Rapid Antibody Humanization: Designed Combinatorial V Gene Libraries," PNAS, USA, vol. 95, pp. 8910-8915 (1998).

Riemer , A. et al. "Matching of trastuzumab (Herceptin) epitope mimics onto the surface of Her-2/neu—a new method of epitope definition", Mol. Immunol, vol. 42:, pp. 1121-1124 (2005).

(56) References Cited

OTHER PUBLICATIONS

Rudikoff, S. et al., "Single amino acid substitution altering antigen-binding specificity," Proc Natl Acad Sci USA, vol. 79, pp. 1979-1983 (1982).
Saijo, N., "What are the reasons for negative phase III trials of molecular-target-based drugs?",; Cancer Sci., vol. 95(10), pp. 772-776 (2004).
Salih, Helmut R. et al., "Cutting Edge: Down-Regulation of MICA on Human Tumors by Proteolytic Shedding," The Journal of Immunology, vol. 169, pp. 4098-4102 (2002).
Salih, Helmut R. et al., "Functional expression and release of ligands for the activating immunoreceptor NKG2D in leukemia," Blood, vol. 102(4), pp. 1389-1396 (2003).
Schoenfeld, J. et al., "Active Immunotherapy Induces Antibody Responses That Target Tumor Angiogenesis," Microenvironment and Immunology, Cancer Research, vol. 70(24), pp. 10150-10160 (2010).
Sircar, A. et al., "Rosetta Antibody: antibody variable region homology modeling server," Nucleic Acids Research, vol. 37, pp. W474-W479 (2009).
Steinle, A. et al., "Diversification, expression, and gammadelta T cell recognition of evolutionarily distant members of the MIC family of major histocompatibility complex class I-related molecules," Proc. Natl. Acad. Sci. USA, vol. 95, pp. 12510-12515 (1998).
Suarez-Alvarez, B. et al., "Identification of epitopes and immunodominant regions on the MICA protein defined by alloantibodies from kidney transplant patients," Transplantation, Williams and Wilkins, GB, vol. 88 (3) Suppl, pp. S68-S77( Aug. 15, 2009).
Tang, B. et al., "Evaluation of human major histocompatibility complex class I chain-related A as a potential target for tumor imaging," Cancer Letters, New York, NY, US, vol. 263 (1), pp. 99-106, Jan. 30, 2008.
Thom, George et al., "Probing a protein-protein interaction by in vitro evolution," PNAS, vol. 103(20):7619-7624 (2006).
Vajdos, FF et al., "Comprehensive functional maps of the antigen-binding site of an anti-ErbB2 antibody obtained with shotgun scanning mutagenesis," J Mol Biol. vol. 320(2) pp. 415-428 (2002).
Vitetta, Ellen S. et al., "Monoclonal Antibodies as Agonists: An Expanded Role for Their Use in Cancer Therapy," Cancer Research, vol. 54:5301-5309 (1994).
Weber, "Review: anti-CTLA-4 antibody ipilimumab: case studies of clinical response and immune-related adverse events," Oncologist, 12(7): 864-872 (2007).
Whiteside, T. et al., "Antigen-Processing Machinery in Human Dendritic Cells; Up-regulation by Maturation and Down-Regulation by Tumor Cells," J. Immunol., vol. 173, pp. 1526-1534 (2004).
Wongsena et al "Production and characterization of monoclonal antibodies against major histocompatibility complex class 1 chain-related gene A," Tissue Antigens, 72(5):431-440 (2008).
Wu et al., "Prevalent expression of the immunostimulatory MHC class I chain-related molecule is counteracted by shedding in prostate cancer," J. Clin. Invest.,114 (4): 560-568 (2004).
Zou, Yizhou et al., "MICA is a Target for Complement-Dependent Cytotoxicity With Mouse Monoclonal Antibodies and Human Alloantibodies," Human Immunology, vol. 63, pp. 30-39 (2002).
Zwirner, N. et al., "Immunobiology of the human MHC class I chain-related gene A (MICA): from 13 transplantation immunology to tumor immune escape," Immunologia, vol. 25(1), pp. 25-38, (Jan.-Mar. 2006).
Ali, O. A. et al., "Infection-mimicking materials to program dendritic cells in situ," Nature Materials, 8:151-158 (2009).
Ali et al. "In Situ Regulation of DC Subsets and T Cells Mediates Tumor Regression in Mice," Science Translation Medicine, 1, 8ra19, 12 pages (2009).
Almagro et al., "Humanization of antibodies," Frontiers in Bioscience, 13:1619-33 (2008).
Altschul et al. "Basic Local Alignment Search Tool," J. Mol. Biol., 215:403-10 (1990).
Altschul et al., "Gapped BLAST and PSI-BLAST: a new generation of protein database search programs," Nucleic Acids Res. 25(17):3389-3402 (1997).
Amanna et al., "Duration of Humoral Immunity to Common Viral and Vaccine Antigens," N. Engl. J. Med., 357:1903-1915, (2007).
Andrade et al., "Adsorption of complex proteins at interfaces," Pure and Appl. Chem., 64(11):1777-1781 (1992).
Balazs et al., "Antibody-based protection against HIV infection by vectored immunoprophylaxis," Nature, 481(7379):81-4 (2011).
Balmana et al. "BRCA in breast cancer: ESMO Clinical Recommendations," Annals of Oncology 20(supplement 4):iv19-20 (2009).
Banchereau et al. "Long-Term Human B Cell Lines Dependent on Interleukin-4 and Antibody to CD40," Science, 251:70 (1991).
Bendsten et al. "Improved Prediction of Signal Peptides: SignalP 3.0," J Mol Biol 340(4):783-95 (2004).
Benjamin et al. "The Antigenic Structure of Proteins: A Reappraisal," Ann Rev Immunol, 2:67-101 (1984).
Bird et al. "Single-Chain Antigen-Binding Proteins," Science 242:423-426 (1988).
Buisman et al., "Long-term presence of memory B-cells specific for different vaccine components," Vaccine, 28:179-186 (2010).
Boerner et al, "Production of antigen-specific human monoclonal antibodies from in vitro-primed human splenocytes," J Immunol, 147(1):86-95 (1991).
Bordo et al. "Suggestions for "Safe" Residue Substitutions in Site-Directed Mutagenesis," J. Mol. Biol., 217:721-729 (1991).
Caine et al., "Recombinant Human Phenylethanolamine N-Methyltransferase: Overproduction in *Escherichia coli*, Purification, and Characterization," Protein Expression and Purification, 8(2):159-166 (1996).
Canfield "The Binding Affinity of Human IgG for its High Affinity Fc Receptor Is Determined by Multiple Amino Acids in the CH2 Domain and Is Modulated by the Hinge Region," J. Exp. Med. 173:1483 (1991).
Cao et al., "An optimized assay for the enumeration of antigen-specific memory B cells in different compartments of the human body," Journal of Immunological Methods, 358:56-65 (2010).
Champe et al. "Monoclonal Antibodies That Block the Activity of Leukocyte Function-associated Antigen 1 Recognize Three Discrete Epitopes in the Inserted Domain of CD11a," The Journal of Biological Chemistry, 270:1388-1394 (1995).
Cheung et al., "Epitope-Specific Antibody Response to the Surface Antigen of Duck Hepatitis B Virus in Infected Ducks," Virology, 176:546 (1990).
Choi et al., "Evolutionary conservation in multiple faces of protein interaction," Proteins: Structure, Function, and Bioinformatics, 77(1):14-25 (2009).
Chothia et al. "Canonical Structures for the Hypervariable Regions," J Mol Biol, 196:901-917 (1987).
Clackson et al, "Making antibody fragments using phage display libraries," Nature, 352 624-628 (1991).
Cole et al, "The EBV-Hybridoma Technique and its Application to Human Lung Cancer," Monoclonal Antibodies and Cancer Therapy, pp. 77-96 (1985).
Corada et al., Monoclonal antibodies directed to different regions of vascular endothelial cadherin extracellular domain affect adhesion and clustering of the protein and modulate endothelial permeability, Blood,97:1679-84 (2001).
Corti et al., "Analysis of Memory B Cell Responses and Isolation of Novel Monoclonal Antibodies with Neutralizing Breadth from HIV-1-Infected Individuals," PLoS One, 5:e8805 (2010).
Cox et al., "Glycan optimization of a human monoclonal antibody in the aquatic plant Lemna minor," Nat. Biotechnol, 24(12):1591-7 (2006).
Cox, J. P. L. et al. "A Directory of Human Germ-line VH Segments Reveals a Strong Bias in their Usage," Eur. J Immunol., 24:827-836 (1994).
Crotty et al., "Cutting Edge: Long-Term B Cell Memory in Humans after Smallpox Vaccination," J. Immunol., 171:4969-4973 (2003).
Cunningham et al. "High-Resolution Epitope Mapping of hGH-Receptor Interactions by Alanine-Scanning Mutagenesis," Science, 244:1081-1085 (1989).

(56) References Cited

OTHER PUBLICATIONS

Dall'Acqua et al. "Increasing the Affinity of a Human IgG1 for the Neonatal Fc Receptor: Biological Consequences", Journal of Immunology, 169:5171-5180 (2002).
Dall'Acqua et al., "Properties of Human IgG1s Engineered for Enhanced Binding to the Neonatal Fc Receptor (FcRn)", Journal of Biological Chemistry 281:23514-23524 (2006).
De Genst et al., "Antibody repertoire development in camelids ", Dev Comp Immunol; 30:187-98 (2006).
De Ridder, G. et al. "Cell-Surface GRP78 and its Antibodies: Pathologic and Therapeutic Roles in Cancer", 2010. Retrieved from the Internet: URL:http://dukespace.lib.duke.edu/dspace/bitstream/handle/10161/3805/deRidder_duke_0066D_10579.pdf?sequence=1.
Duncan et al., "Localization of the binding site for the human high-affinity Fc receptoron IgG," Nature, 332:563 (1988).
Emini et al. "Antigenic Conservation and Divergence between the Viral-Specific Proteins of Poliovirus Type 1 and Various Picornaviruses", Virology 140 13-20 (1985).
Fang et al. "Stable antibody expression at therapeutic levels using the 2A peptide", Nature Biotechnology 23, 584-590 ((2005).
Fecteau et al., "Peripheral blood CD27+ IgG+ B cells rapidly proliferate and differentiate into immunoglobulin-secreting cells after exposure to low CD154 interaction", Immunology, 128:e353-e365 30 (2009).
Fields et al., Chapter 3 "Synthetic Peptides: A User's Guide", pp. 77-183 (1992).
Fishwild et al, "High-avidity human IgGk monoclonal antibodies from a novel strain of minilocus transgenic mice", Nature Biotechnology 14, 845-51 (1996).
Franz et al. "Ex vivo characterization and isolation of rare memory B cells with antigen tetramers", Blood, 118(2):348-357 (2011).
Getzoff et al. "The Chemistry and Mechanism of Antibody Binding to Protein Antigens", Advances in Immunology 43:1-98, (1988).
Gillies S.D. et al., "Improving the Efficacy of Antibody-Interleukin 2 Fusion Proteins by Reducing Their Interaction with Fc Receptors", Cancer Res. 59:2159-66 (1999).
Gong et al., "A protein domain interaction interface database: InterPare", BMC: Bioinformatics, 6:1471-2105 (2007).
Gonzalez, G. et al., "A novel cancer vaccine composed of human-recombinant epidermal growth factor linked to a carrier protein: Report of a pilot clinical trial," Annals of Oncology, 9:431-435 (1998).
Groh, V. et al., "Recognition of Stress-Induced MHC Molecules by Intestinal Epithelial gammadelta T cells," Science 279:1737-1740 (1988).
Guo et al., "Protein tolerance to random amino acid change", Proc. Natl. Acad. Sci., USA, 101(25):9205-9210 (2004).
Henn et al., "Modulation of Single-Cell IgG Secretion Frequency and Rates in Human Memory B Cells by CpG DNA, CD40L, IL-21, and Cell Division", J. Immunol., 183:31777-3187 (2009).
Hinton et al. "An Engineered Human IgG1 Antibody with Longer Serum Half-Life", Journal of Immunology 176:346-356 (2006).
Hinton et al., "Engineered Human IgG Antibodies with Longer Serum Half-lives in Primates", J. Biol. Chem. 279(8): 6213-6216 (2004).
Hofer et al., Adaptation of humoral memory, Immunological Reviews, 211:295-302 (2006).
Hofmann et al. "A database of membrane spanning proteins segments", Biol Chem Hoppe-Seyler 374,166 (1993).
Hoogenboom et al. "Human Antibodies from Synthetic Repertoires of Germline VH Gene Segments Rearranged in Vitro", J Mol Biol, 227 381 (1991).
Hopp et al. "A computer program for predicting protein antigenic determinants", Molecular Immunology 20 483-489 (1983).
Hopp et al. "Prediction of protein antigenic determinants from amino acid sequences", Proc Natl Acad Sci USA 78 3824-3828 (1981).
Hopp, Methods for identifying antigenic determinants and other interaction sites, Immunol Methods 88 1-18 (1986).
Huergo-Zapico L. et al. "Expression of ERp5 and GRP78 on the membrane of chronic lymphocytic leukemia cells: association with soluble MICA shedding", Cancer Immunology, Immunotherapy, 61(8):1201-1210 (2012).
Huggins et al., "CpG DNA activation and plasma-cell differentiation of CD27_ naïve human B cells", Blood, 109:1611-1619 (2007).
Huston et al. "Protein engineering of antibody binding sites: Recovery of specific activity in an antidigoxin single-chain Fv analogue produced in *Escherichia coli*", Proc. Natl. Acad. Sci. USA 85:5879-5883 (1988).
Jaeger et al., "Improved predictions of secondary structures for RNA", Proc. Natl. Acad. Sci. USA 86:7706-10 (1989).
Jaeger et al., "Predicting Optimal and Suboptimal Secondary Structure for RNA", Methods Enzymol. 183:281-306 (1989).
Jameson, et al. The antigenic index: a novel algorithm for predicting antigenic determinants, Comput Appl Biosci 4(1) 181-186 (1988).
Jespers et al., "Guiding the Selection of Human Antibodies from Phage Display Repertoires to a Single Epitope of an Antigen", Biotechnology 12:899, (1994).
Jiang, et al., "TLR9 stimulation drives naive B cells to proliferate and to attain enhanced antigen presenting function", Eur. J. Immunol., 37:2205-2213 (2007).
Johnson et al. A Structural Basis for Sequence Comparisons: An Evaluation of Scoring Methodologies, J. Mol. Biol. 233:716-738 (1993).
Jones, P. et al. "Replacing the complementarity-determining regions in a human antibody with those from a mouse", Nature 321:522-525 (1986).
Jourdan et al., "An in vitro model of differentiation of memory B cells into plasmablasts and plasma cells including detailed phenotypic and molecular characterization", Blood, 114:5173-5181 (2009).
Kalos M, et al., "T Cells with Chimeric Antigen Receptors Have Potent Antitumor Effects and Can Establish Memory in Patients with Advanced Leukemia", Sci Transl Med. Aug. 2010;3 (95), (2011).
Kaneko et al., "Anti-Inflammatory Activity of Immunoglobulin G Resulting from Fc Sialylation", Science 313:670-673 (2006).
Kettleborough et al, "Humanization of a mouse monoclonal antibody by CDR-grafting: the importance of framework residues on loop conformation," Protein Eng 4(7) 773 83 (1991).
Kim et al., "Targeting Heat Shock Proteins on Cancer Cells: Selection, Characterization, and Cell-Penetrating Properties of a Peptidic GRP78 Ligand," Biochemistry 45:9434-9444 (2006).
Kirkland et al., "Analysis of the Fine Specificity and Cross-Reactivity of Monoclonal Anti-Lipid A Antibodies", J Immunol. 137:3614 (1986).
Klinman "CpG DNA as a vaccine adjuvant", Expert Review Vaccines 2(2):305-15 (2003).
Kostelny et al., "Formation of a Bispecific Antibody by the Use of Leucine Zippers", Journal of Immunol. 148, 1547-1553 (1992).
Kratz et al. "Native display of complete foreign protein domains on the surface of hepatitis B virus capsids", Proc Natl Acad Sci USA. 96(5):1915-1920 (1999).
Krogh et al. "Predicting transmembrane protein topology with a hidden Markov model Application to complete genomes", Journal of Molecular Biology, 305(3) 567-580, (2001).
Kunkel et al., "Plasma-Cell Homing", Nat. Rev. Immunol., 3:822-829 (2003).
Kyte et al. "A Simple Method for Displaying the Hydropathic Character of a Protein", J Mol Biol 157 105-132 (1982).
Lanzavecchia et al., "Human B cell memory", Curr. Opin. Immunol. 21:298-304 (2009).
Li et al., "Optimization of humanized IgGs in glycoengineered *Pichia pastoris*", Nature Biotechnology 24(2):210-215 (2006).
Liu et al. "Perturbation of NK cell peripheral homeostasis accelerates prostate carcinoma metastasis", The Journal of Clinical Investigation 123(10):4410-4422 (2013).
Liu R. et al. "Monoclonal Antibody against Cell Surface GRP78 as a Novel Agent in Suppressing PI3K/AKT Signaling, Tumor Growth, and Metastasis", Clinical Cancer Research, 19(24):6802-6811 (2013).
Lonberg "Human antibodies from transgenic animals", Nature Biotechnology 23(9): 1117-1125, (2005).

(56) References Cited

OTHER PUBLICATIONS

Lonberg et al, "Antigen-specific human antibodies from mice comprising four distinct genetic modifications", Nature 368 856-859 (1994).
Lonberg et al, "Human Antibodies from Transgenic Mice", International Reviews of Immunology, 13 65-93 (1995).
Makabe et al., "Thermodynamic Consequences of Mutations in Vernier Zone Residues of a Humanized Anti-human Epidermal Growth Factor Receptor Murine Antibody, 528", Journal of Biological Chemistry, 283:1156-1166 (2008).
Marks et al, "By-Passing Immunization: Building High Affinity Human Antibodies by Chain Shuffling", Bio/Technology 10, 779-783 (1992).
Marks et al, "Human Antibodies from V-gene Libraries Displayed on Phage", J Mol Biol, 222 581-597 (1991).
McCafferty et al, "Phage antibodies: filamentous phage displaying antibody variable domains", Nature, 348 552-554 (1990).
Meyers E. et al. "Optimal alignments in linear space", CABIOS, 4:11-17 (1989).
Milone et al. "Chimeric Receptors Containing CD137 Signal Transduction Domains Mediate Enhanced Survival of T Cells and Increased Antileukemic Efficacy In Vivo", Mol. Ther. 17:1453 (2009).
Moldenhauer et al., "Identity of HML-1 Antigen on Intestinal Intraepithelial T Cells and of B-ly7 Antigen on Hairy Cell Leukaemia", Scand. J Immunol. 32:77 (1990).
Morel et al., "Monoclonal Antibodies to Bovine Serum Albumin: Affinity and Specificity Determinations", Mol. Immunol. 25(1):7 (1988).
Morrison et al, "Chimeric human antibody molecules: Mouse antigen-binding domains with human constant region domains", Proc Natl Acad Sci USA, 81 6851-6855 (1984).
Morrison et al., "Genetically Engineered Antibody Molecules," Advances in Immunology, 44:65-92 (1988).
Morrison, "Success in Specification", Nature 368, 812-13 (1994).
Nassal, M. et al., "Development of hepatitus B virus capsids into a whole-chain protein antigen display platform: New particulate Lyme disease vaccines," International Journal of Medical Microbiology, 298:135-142 (2008).
Nechansky et al., "Compensation of endogenous IgG mediated inhibition of antibody-dependent cellular cytotoxicity by glycoengineering of therapeutic antibodies", Molecular Immunology 44(7): 1815-1817 (2007).
Needleman et al. "A General Method Applicable to the Search for Similarities in the Amino Acid Sequence of Two Proteins", J. Mol. Biol. 48:443-453 (1970).
Neuberger, "Generating high-avidity human Mabs in mice", Nature Biotechnology 14,826 (1996).
Odendahl et al., "Generation of migratory antigen-specific plasma blasts and mobilization of resident plasma cells in a secondary immune response", Blood, 105:1614-1621 (2005).
Padlan, "A possible procedure for reducing the immunogenicity of antibody variable domains while preserving their ligand-binding properties", Molecular Immunology, 28 489-498 (1991).
Padlan, "Anatomy of the Antibody Molecule", Molecular Immunology 31(3) 169-217 (1994).
Padlan, "X-Ray Crystallography of Antibodies", Advances in Protein Chemistry 49:57-133 (1996).
Park et al., "Prediction of protein-protein interaction types using association rule based classification", BMC: Bioinformatics, 10:36 (2009); doi: 10.1186/1471-2105-10-36, 15 pages.
Pashine et al. "Targeting the innate immune response with improved vaccine adjuvants", Nature Med. 11(4):S63-S68 (2005).
Pearson et al. "Improved tools for biological sequence comparison", Proc. Natl. Acad. Sci. USA 85:2444 (1988).
Pearson, "Rapid and Sensitive Sequence Comparison with FASTP and FASTA", Meth. Enzymology, 183:63-98 (1990).
Pluckthun, "Mono- and Bivalent Antibody Fragments Produced in *Escherichia coli*: Engineering, Folding and Antigen Binding", Immunol. Reviews 130:151-188 (1992).

Qi, J. et al., "Immobilized MICA Could Expand Human V γ1 γδ T cells In Vitro that Displayed Major Histocompatibility Comlex Class I Chain-Related A-Dependent Cytotoxicity to Human Epithelial Carcinomas," Scandinavian Journal of Immunology, 58:211-220 (2003).
Queen, C. et al. "A humanized antibody that binds to the interleukin 2 receptor", Proc. Natl. Acad. Sci. USA 86:10029-10033 (1989).
Riechmann, L. et al. "Reshaping human antibodies for therapy", Nature 332:323-327 (1998).
Sarmay et al. "Mapping and Comparison of the Interaction Sites on the Fc Region of IgG Responsible for Triggering Antibody Dependent Cellular Cytotoxicity (ADCC) through Different Types of Human Fcγ Receptor", Molec. Immunol. 29 (5): 633-9 (1992).
Scallon et al., "Higher levels of sialylated Fc glycans in immunoglobulin G molecules can adversely impact functionality", Mol Immunol. 44(7): 1524-34 (2007).
Scatchard, "The attractions of proteins for small molecules and ions", Ann NY Acad Sci 51 660-672, (1949).
Scheid et al., "Broad diversity of neutralizing antibodies isolated from memory B cells in HIV-infected individuals", Nature, 458:636-640 (2009).
Shields, R.L. et al. "High Resolution Mapping of the Binding Site on Human IgG1 for FcgRI, FcgRII, FcgRIII, and FcRn and Design of IgG1 Variants with Improved Binding to the FcgR", J Biol. Chem. 276:6591-6604 (2001).
Shields, R.L. et al. "Lack of Fucose on Human IgG1 N-Linked Oligosaccharide Improves Binding to Human FcγRIII and Antibody-dependent Cellular Toxicity", J Biol. Chem. 277:26733-26740 (2002).
Skerra et al., "Bacterial expression of immunoglobulin fragments", Curr. Opinion in Immunol., 5:256-262 (1993).
Smith et al. "Comparison of Biosequences", Advances in Applied Mathematics, 2:482 (1981).
Songsivilai et al. "Bispecific antibody: a tool for diagnosis and treatment of disease", Clin. Exp. Immunol. 79:315-321 (1990).
Spear et al., "NKG2D ligands as therapeutic targets," Cancer Immunity, 13:1-14 (2013).
Stahli et al.,"Distinction of Epitopes by Monoclonal Antibodies", Methods in Enzymology 92:242-253 (1983).
Strohl, "Optimization of Fc-mediated effector functions of monoclonal Antibodies", Current Opinion in Biotechnology 20:685-691 (2009).
Tao et al. "Role of Carbohydrate in the Structure and Effector Functions Mediated by the Human IgG Constant Region", J. Immunol. 143:2595-2601 (1989).
Tao et al., "Structural Features of Human Immunoglobulin G that Determine Isotype-specitic Differences in Complement Activation", J. Exp. Med. 178:661 (1993).
Taylor, The Classification of Amino Acid Conservation, J. Theor. Biol. 119:205-218 (1986).
Tomlinson, I. M., et al. "The Repertoire of Human Germline VH Sequences Reveals about Fifty Groups of VH Segments with Different Hypervariable Loops" J. Mol. Biol. 227:776-798 (1992).
Umana et al. "Engineered glycoforms of an antineuroblastoma IgG1 with optimized antibodydependent cellular cytotoxic activity", Nat. Biotech. 17:176-180 (1999).
Verhoeyen et al, "Reshaping Human Antibodies: Grafting an Antilysozyme Activity", Science 239 1534 1536 (1988).
Vetter, C. S. et al., "Expression of Stress-induced MHC Class I Related Chain Molecules on Human Melanoma," The Journal of Investigative Dermatology, 118(4):600-605 (2002).
Wang, M. et al. "Role of the Unfolded Protein Response Regulator GRP78/BiP in Development, Cancer, and Neurological Disorders", Antioxidants and Redox Signaling 11(9): 2307-2316 (2009).
Wang et al., "Human immunoglobulin variable region gene analysis by single cell RT-PCR", J. Immunol. Methods, 244:217-225 (2000).
Ward et al., "Binding activities of a repertoire of single immunoglobulin variable domains secreted from *Escherichia coli*", Nature 341:544-546 (1989).
Wu et al., "Rational Design of Envelope Identifies Broadly Neutralizing Human Monoclonal Antibodies to HIV-1", Science, 329:856-861 (2010).

(56) References Cited

OTHER PUBLICATIONS

Yeung et al., "Engineering Human IgG1 Affinity to Human Neonatal Fc Receptor: Impact of Affinity Improvement on Pharmacokinetics in Primates", J Immunol, 182:7663-7671 (2010).

Yoshida et al., "Memory B and memory plasma Cells", Immunol. Rev., 237:117-139 (2010).

Yu et al. "Minimal Lipidation Stabilizes Protein-Like Molecular Architecture", J Am. Chem. Soc., 120(39):9979-9987 (1998).

Zapata et al , "Engineering linear F(ab')2 fragments for efficient production in *Escherichia coli* and enhanced antiproliferative activity", Protein Eng 8(10) 1057-1062 (1995).

Zuker, "On Finding All Suboptimal Foldings of an RNA Molecule", Science 244:48-52 (1989).

Araya, Carlos L. et al., "Deep mutational scanning: assessing protein function on a massive scale," Trends Biotechnol., vol. 29(9), pp. 435-442 (2011 ).

Barbas, S. et al., "Recognition of DNA by Synthetic Antibodies," J. Am. Chem. Soc., vol. 116 (5), pp. 2161-2162 (1994).

Beiboer, S. et al., "Guided Selection of a Pan Carcinoma Specific Antibody Reveals Similar Binding Characteristics yet Structural Divergence Between the Original Murine Antibody and its Human Equivalient," JMB, vol. 296, pp. 833-849 (2000).

Bergers et al., "Extrinsic regulators of epithelial tumor progression: metalloproteinases," Curro Opin. in Genetics and Development, vol. 10, pp. 120-127 (2000).

Bodey, B. et al., "Failure of Cancer Vaccines: The Significant Limitations of this Approach to Immunotherapy," Anticancer Research, vol. 20, pp. 2665-2676 (2000).

Brown, M. et al., "Tolerance of single, but not multiple, amino acid replacements in antibody VH CDR 2: a means of minimizing B cell wastage from somatic hypermutation?," J Immunol., vol. 156(9), pp. 3285-3291 (1996).

Casset, F. et al., "A peptide mimetic of an anti-CD4 monoclonal antibody by rational design," BBRC, vol. 307, pp. 198-205(2003).

Chen, C. et al., "Generation and Analysis of Random Point Mutations in an Antibody CDR2 Sequence: Many Mutated Antibodies Lose Their Ability to Bind Antigen," J. Exp. Med., vol. 176, pp. 855-866 (1992).

Chen, Y. et al, "Selection and analysis of an optimized anti-VEGF antibody: crystal structure of an affinity-matured Fab in complex with antigen," J. Mol. Biol., vol. 293, pp. 865-881 (1999).

Chin et al., "Immune intervention with monoclonal antibodies targeting CD152 (CTLA-4) for autoimmune and malignant diseases," Chang Gung Med J., 31 (1): 1-15 (2008).

Chothia, C. et al., "Conformations of Immunoglobulin hypervariable regions," Nature, vol. 342, pp. 877-883 (1989).

Chothia, C. et al., "Structural Repertoire of the Human VH Segments," J. Mol. Biol., vol. 227, pp. 799-817 (1992).

De Pascalis, R. et al, "Grafting of "abbreviated" complementarity-determining regions containing specificity-determining residues essential for ligand contact to engineer a less immunogenic humanized monoclonal antibody," The Journal of Immunology, vol. 169, pp. 3076-3084 (2002).

Dennis, C. "Off by a whisker", Nature, vol. 442, pp. 739-741 (2006).

Ditzel, H. et al., "Determinants of Polyreactivity in a Large Panel of Recombinant Human Antibodies from HIV-I Infection," The Journal of Immunology, vol. 157, pp. 739-749, (1996).

Doubrovina et al.,"Evasion from NK cell immunity by MHC class I chain-related molecules expressing colon adenocarcinoma," J. Immunol. 171 (12): 6891-6899 (2003).

Duquesnoy, Structurally based epitope analysis of major histocompatibility complex class I-related chain A (MICA) antibody specificity patterns, Human Immunology, vol. 69:826-832 (2008).

Extended European Search Report, EPI2835118.6, dated May 4, 2015, 9 pages.

Fonseca, C. et al., "Protein disulfide isomerases are antibody targets during immune-mediated tumor destruction", Blood, 1vol. 13, pp. 1681-1688 (2009).

Germain, C. et al., "Mhc Class I-Related Chain A Conjugated to Antitumor Antibodies Can Sensitize Tumor Cells to Specific Lysis by Natural Killer Cells," Clinical Cancer Research, The American Association for Cancer Research, US, vol. 11 (20), pp. 7516-7522, Oct. 15, 2005.

Girlanda, S. et al., "MICA Expressed by Multiple Myeloma and Monoclonal Gammopathy of Undetermined Significance Plasma Cells Costimulates Pamidronate-activated Gammadelta Lymphocytes," Cancer Research, vol. 65(16), pp. 7502-7508 (2005).

Groh, V. et al., "Broad tumor-associated expression and recognition by tumor-derived gammadelta cells of MICA and MICB," Proc. Natl. Acad. Sci. USA, vol. 96:6879-6884 (1999).

Groh, V. et al., "Cell stress-related human major histocompatibility complex class I gene expressed in gastrointestinal epithelium," Proc. Natl. Acad. Sci. USA, vol. 93:12445-12450 (1996).

Groh, V. et al., Efficient cross-priming of tumor anigen-specific T cells by dendritic cells sensistized with diverse anti-MICA opsonized tumor cells. Proc. Nat'l Acad. Sci., May 2005. vol. 102, No. 18 pp. 6461-6466.

Groh, V. et al., "Recognition of Stress-Induced MHC Molecules by Intestinal Epithelial gammadelta T Cells," Science, vol. 279:1737-1740 (1998).

Groh, V. et al., "Tumour-derived soluble MIC ligands impair expression of NKG2D and T-cell activation," Nature, vol. 419:734-738 (2002).

Gura, T. "Systems for Identifying New Drugs are Often Faulty", Science, 278: 1041-1042 (1997).

Hara et al., "Interleukin-2 potentiation of cetuximab antitumor activity for epidermal growth factor receptor-overexpressing gastric cancer xenografts through antibody-dependent cellular cytotoxicity," Cancer Sci., 99 (7): 471-478 (2008).

Holm, P. et al. "Functional mapping and single chain construction of the anti-cytokeratin 8 monoclonal antibody TS1," Mol. Immunol., vol. 44, pp. 1075-1084 (2007).

Hue, S. et al., "Potential Role of NKG2D/MHC Class I-Related Chain a Interaction in Intrathymic Maturation of Single-Positive CD8 T Cells," The Journal of Immunology, vol. 171, pp. 1909-1917 (2003).

International Preliminary Report on Patentability, PCT/US2014/029348, dated Sep. 15, 2015, 7 pages.

International Preliminary Report on Patentability, PCT/US2014/068862, dated Jun. 7, 2016, 7 pages.

International Search Report and Written Opinion, PCT/US2014/029348, dated Oct. 16, 2014, 11 pages.

Jiang, B. et al., "A Novel Peptide Isolated from a Phage Display Peptide Library with Trastuzumab Can Mimic Antigen Epitope of HER-2", J. Biol. Chem., vol. 280 (6), pp. 4656-4662 (2005).

Jinushi, M. et al. "MHC class I chain-related protein A antibodies and shedding are associated with the progression of multiple myeloma", PNAS, vol. 105, pp. 1285-1290 (2008).

Jinushi, M. et al., "Enhancing the clinical activity of granulocyte-macrophage colony stimulating factor-secreting tumor cell vaccines", Immunological Reviews, vol. 222, pp. 287-298 (2008).

Jinushi, M. et al., "Impairment of natural killer cell and dendritic cell functions by the soluble form of MHC class I-related chain A in advanced human hepatocellular carcinomas", J. of Hepatology, vol. 43, pp. 1013-1020 (2005).

Jinushi, M. et al., "Therapy-induced antibodies to Wic class I chain-related protein A antagonize immune suppression and stimulate antitumor cytotoxicity.," Proc. Nat'l Acad. Sci., vol. 103(24) pp. 9190-9195 (Jun. 2006 ).

Jordan, Peter A. et al., "A role for the thiol isomerase protein ERP5 in platelet function," Blood, vol. 105 (4), pp. 1500-1507 (2005).

Kaiser, Brett et al., "Disulphide-isomerase-enabled shedding of tumour-associated NKG2D ligands", Nature, vol. 447, pp. 482-487 (2007).

Kelland, L.R. "Of mice and men: values and liabilities of the athymic nude mouse model in anticancer drug development", Eur. J. Cancer, vol. 40 (6), pp. 827-836 (2004).

Klimka, A., et al., "Human anti-CD30 recombinant antibodies by guided phage antibody selection using cell panning," British Journal of Cancer, vol. 83(2), pp. 252-260 (2000).

(56) References Cited

OTHER PUBLICATIONS

Kuo et al.,"Anti-caveolin-1 antibodies as anti-prostate cancer therapeutics," Hybridoma, 31 (2): 77-86 (2012).
Leblond et al.,"The amphipathic alpha-helical repeats of apolipoprotein A-I are responsible for binding of high density lipoproteins to HepG2 cells," J. Biol. Chem., 266 (10): 6058-6067 (1991).
Liu et al.,"The Cutting edge: The membrane type matrix metalloproteinase MMP14 mediates constitutive shedding of MHC class I chain-related molecule A independent of A disintegrin and metalloproteinases," J. Immunol. 184 (7): 3346-3350 (2010).
MacCallum, R. et al., "Antibody-antigen interactions: contact analysis and binding site topography," J. Mol. Biol, vol. 262,pp. 732-745 (1996).
Marten et al., "Soluble MIC is elevated in the serum of patients with pancreatic carcinoma diminishing gammadelta T cell cytotoxicity," Int. J. Cancer. 119 (10): 2359-2365 (2006).
Martin, D., et al., "Symposium on Cancer Immunology and Immunotherapy," Roche/Nature Medicine, Sep. 11-13, 2011 Roche, Nutley, New Jersey, USA, 91 pages (2011).
Masahisa K. et al "WIC class 1 chain-related protein A antibodies and shedding are associated with the progression of multiple myeloma" PNAS, vol. 15(4):1285-1290 (2008).
May, K. et al., "Isolation of human anti-MICA antibody from cancer patients responding to immunotherapies," Journal of Clinical Oncology, vol. 30(15), 2012 ASCO Annual Meeting (Abstract No. 3502, 2 pages (2012).
U.S. Appl. No. 14/025,573, Dec. 17, 2015.
U.S. Appl. No. 14/025,573, Jun. 27, 2014.
U.S. Appl. No. 14/025,573, Jan. 31, 2014.
U.S. Appl. No. 14/025,573, Oct. 31, 2013.
U.S. Appl. No. 14/442,222, Jul. 25, 2014.
U.S. Appl. No. 14/442,222, May 29, 2013.
U.S. Appl. No. 14/442,222, Jun. 28, 2012.
U.S. Appl. No. 14/442,222, Oct. 6, 2011.
U.S. Appl. No. 14/021,111, Sep. 7, 2016.
U.S. Appl. No. 14/021,111, Feb. 11, 2016.
U.S. Appl. No. 14/021,111, Sep. 29, 2015.
U.S. Appl. No. 12/442,222, filed Dec. 23, 2009, Dranoff et al.
U.S. Appl. No. 14/021,111, filed Sep. 9, 2013, Dranoff et al.
U.S. Appl. No. 14/025,573, filed Sep. 12, 2013, Wucherpfennig et al.
U.S. Appl. No. 14/776,968, filed Feb. 18, 2016, Wucherpfennig et al.
De Andrade, L. F. et al., Antibody-mediated inhibition of MICA and MICB shedding promotes NK cell-driven tumor immunity, Science 359: 1537-1542 (2018).
Wang, X. et al., "An six-amino acid motif in the α3 domain of MICA is the cancer therapeutic target to inhibit shedding," Biochemical and Biophysical Research Communications, 387:476-481 (2009).

* cited by examiner

CAGGTGCAGCTACAGCAGTGGGGCGCAGGACTGTTGAAGCCTTCGGAGACCCTGTCTCT
GGTGGGTCCTTCACTGATCATTACTGGAGTTGGATCCGTCAGCCCCCAGGGAAGGGGCTGGAGTGGATTGGAGAAA
ATCAATCATAGTGGAGTCACCAACTACAACCCGTCCCTCAAGAGTAGACTCACAGACGTCCAAG
AGCCAGTTCTCCCTGAAGCTGAGCTCTGTGACCGCCGCGGACACGGCTGTGTACTACTGTGCGAAAACTGGCCTG
TATTATGATGACGTTTGGGGACTTTCGTCCAGGGGCGGGTTCGACTCCTGGGGCCAGGGAACCCTGGTCACC
GTCTCCTCA (SEQ ID NO: 1)

FIG. 1

Q V Q L Q Q W G A G L L K P S E T L A L T C A V S
G G S F S D H Y W S W I R Q A P G K G L E W I G E
I N H S G V T N Y N P S L K S R L T I S V D T S K
S Q F S L R L S S V T A A D T A L Y Y C A K T G L
Y Y D D V W G T F R P R G G F D S W G Q G T L V T
V S S (SEQ ID NO: 2)

FIG. 2

GACATCGTGATGACCCAGTCTCCGGACTCCCTGGCTGTCTCTCTGGGCGAGAGGGCCACCATCAACTGCAAGTCC
AGCCAGAGTATTTATATAGCTCCGACAATAAGAATTACTTAGCTTGGTACCAACAGAAGCCAGGACAGCCTCCT
AAGCTCCTCTTTTACTGGGCATCTATCCGGGAATCCGGGGTCCCTGACCGATTCAGTGGCGGGTCTGGGACA
GATTTCACTCTCACCATCAGCAGTCTGCAGGCTGAAGATGTGGCAGTTTATTACTGTCAGCAATATTATAGTCCT
CCTTGCAGTTTTGGCCAGGGGACCAAGCTGGAGATCCAA        (SEQ ID NO: 10)

FIG. 3

D I V M T Q S P D S L A V S L G E R A T I N C K S
S Q S I L Y S S D N K N Y L A W Y Q H K P G Q P P
K L L F Y W A S I R E S G V P D R F S G G G Y S P
D F T L T I S S L Q A E D V A V Y Y C Q Q Y Y S P
P C S F G Q G T K L E I Q        (SEQ ID NO: 11)

FIG. 4

1    GAGGTGCAGC TGGTGGAGTC TGGGGGAGGC TTGGTACAGC CTGGGGGGTC CCTGAGACTC
61   TCCTGTGCAG CCTCTGGATT CACCTTTAGT AGTTATGCCA TGAGCTGGGT CCGCCAGGCT
121  CCAGGAAGG  GGCTGGAGTG GGTCTCAGGT ATTTATTGGA GTGGTGGTAG CACATACTAC
181  GCAGACTCCG TGAAGGGCCG GTTCACCATC TCCAGAGACA TATCCAAGAA CACGCTGTAT
241  CTGCAAATGA ACAGTCTGAG AGCCGACGAC ACGGCCGTGT ATTACTGTGC GAGAGGCGAT
301  TACTATGGTT CGGGGGCTCA CTTTGACTAC TGGGGCCAGG GAACCCTGGT CACCGTCTCC
361  TCA  (SEQ ID NO: 19)

FIG. 5

1    EVQLVESGGG LVQPGGSLRL
21   SCAASGFTFS SYAMSWVRQA  CDR1
41   PGKGLEWVSG IYWSGGSTYY  CDR2
61   ADSVKGRFTI SRDISKNTLY
81   LQMNSLRADD TAVYYCARGD  CDR3
101  YYGSGAHFDY WGQGTLVTVS
121  S  (SEQ ID NO: 20)

FIG. 6

```
1    GATATTGTGA TGACCCAGAC TCCACTCTCC TCACCTGTCA CCCTTGGACA GCCGGCCTCC
61   ATCTCCTGCA GGTCTAGCCA AAGCCTCGTA CACAGTGATG GAAACACCTA CTTGAGTTGG
121  CTTCAGCAGA GGCCAGGCCA GCCTCCAAGA CTCCTAATTT ATCAGATTTC TAACCGGTTC
181  TCTGGGGTCC CAGACAGATT CAGTGGCAGT GGGGCAGGGA CAGATTTCAC ACTGAAAATC
241  AGCAGGGTGG AAGCTGAGGA TGTCGGGGTT TACTACTGCA TGCAAGGTAC ACAATTTCCT
301  CGGACGTTCG GCCAAGGGAC CAAGGTGGAA ATCAAA         (SEQ ID NO: 28)
```

FIG. 7

```
1    DIVMTQTPLS SPVTLGQPAS
21   ISCRSSQSLV HSDGNTYLSW   CDR1
41   LQQRPGQPPR LLIYQISNRF   CDR2
61   SGVPDRFSGS GAGTDFTLKI
81   SRVEAEDVGV YYCMQGTQFP   CDR3
101  RTFGQGTKVE IK    (SEQ ID NO: 29)
```

FIG. 8

```
1   GAGGTGCAGC TGGTGGAGTC CGGGGGAGGC TTAGTTCAGC CTGGGGGATC CCTGAGACTC
61  TCCTGTGCAG CCTCAGGGTT CACCTTTAGT AATAACTGGA TGCACTGGGT CCGCCAGGCT
121 CCAGGGAAGG GGCTGGAGTG GATCTCAGAG ATTAGAAGTG ATGGGAATTT CACAAGGTAC
181 GCGGACTCCA TGAAGGGCCG ATTCACCATC TCCAGAGACA ACGCCAAGAG CACACTGTAT
241 TTGCAAATGA ACAGTCTGAG AGTCGAGGAC ACGGGTCTGT ATTACTGTGC AAGAGACTAC
301 CCCTATAGCA TTGACTACTG GGGCCAGGGA ACCCTGGTCA CCGTCTCCTC A   (SEQ ID NO: 37)
```

FIG. 9

```
1   EVQLVESGGG LVQPGGSLRL
21  SCAASGFTFS NNWMHWVRQA   CDR1
41  PGKGLEWISE IRSDGNFTRY   CDR2
61  ADSMKGRFTI SRDNAKSTLY
81  LQMNSLRVED TGLYYCARDY   CDR3
101 PYSIDYWGQG TLVTVSS         (SEQ ID NO: 38)
```

FIG. 10

```
  1  GATATTGTGA TGACCCAGAC TCCACTCTCC TCACCTGTCA CCCTTGGACA GCCGGCCTCC
 61  ATCTCCTGCA CATCTAGTCA AAGCCTCGTA CACAGTAATG GAAACACCTA CTTGAGTTGG
121  CTTCAGCAGA GGCCAGGCCA GCCCCCAAGA CTCCTAATTT ATGAGATTTC TAAGCGGGTC
181  TCTGGGGTCC CAGACAGATT CAGTGGCAGT GGGGCAGGGA CAGATTTCAC ACTGAAAATC
241  AGCAGGGTGG AAGCTGAGGA TGTCGGGGTT TATTACTGCA TGCAAGGTAA ACAACTTCGG
301  ACTTTTGGCC AGGGGACCAA GCTGGAGATC AAA  (SEQ ID NO: 46)
```

FIG. 11

```
  1  DIVMTQTPLS SPVTLGQPAS
 21  ISCTSSQSLV HSNGNTYLSW  CDR1
 41  LQQRPGQPPR LLIYEISKRV  CDR2
 61  SGVPDRFSGS GAGTDFTLKI
 81  SRVEAEDVGV YYCMQGKQLR  CDR3
101  TFGQGTKLEI K  (SEQ ID NO: 47)
```

FIG. 12

```
1   GAGGTGCAGC TGGTGGAGTC TGGGGGAGGC TTGGTACAGC CTGGGGGCTC CGTGAGACTG
61  TCTTGTGCGG CCTCAGGCTT CATTCTTAGC AACTTTGCCA TGAGTTGGGT CCGCCAGGCT
121 CCAGGAAGG GGCTGGACTG GGTCTCAGGT AATTTTGGTG GTCGTGAAAA TACATATTAC
181 GCAGACTCCG TGAAGGGCCG TTTCACCATC TCCAGAGACA GTTCCAAGAG CACACTGTAT
241 CTGCAAATGA ACAATTTGAG AGCCGAGGAC ACGGCCGTAT ATTACTGTGC GCGAGGCGAT
301 TACCATGGTT CGGGGGCTCA CTTTGACTAC TGGGGCCAGG GAATACTGGT CACCGTCTCC
361 TCA  (SEQ ID NO: 55)
```

FIG. 13

```
1    EVQLVESGGG LVQPGGSVRL
21   SCAASGFILS NFAMSWVRQA  CDR1
41   PGKGLDWVSG NFGGRENTYY  CDR2
61   ADSVKGRFTI SRDSSKSTLY
81   LQMNNLRAED TAVYYCARGD  CDR3
101  YHGSGAHFDY WGQGILVTVS
121  S
     (SEQ ID NO: 56)
```

FIG. 14

```
1    GATATTGTGA TGACCCAGAG TCCACTCTCC TCACCTGTCA TCCTTGGACA GCCGGCCTCC
61   ATCTCCTGCA GGTCTAGTCA AAGCCTCCTA CACAGTGATG GAAACACCTA CTTGAGTTGG
121  CTTCACCAGA GGCCAGGCCA GCCTCCTAGA CTCCTAATTT ATCAGATTTC TAACCGGTTC
181  TCTGGGGTCC CAGACAGATT CAGTGGCAGT GGGACAGGGA CAGATTTCAC ACTGAAAATC
241  AGCAGGGTGG AAGCTGAGGA TGCCGGGATT TATTACTGCA TGCAAGGTAC AGAATTTCCT
301  CGGACGTTCG GCCAAGGGAC CAAGGTGGAA ATCAAA      (SEQ ID NO: 64)
```

FIG. 15

```
1    DIVMTQSPLS SPVILGQPAS
21   ISCRSSQSLL HSDGNTYLSW  CDR1
41   LHQRPGQPER LLIYQISNRF  CDR2
61   SGVPDRFSGS GTGTDFTLKI
81   SRVEAEDAGI YYCMQGTEFP  CDR3
101  RTFGQGTKVE IK          (SEQ ID NO: 65)
```

FIG. 16

```
1   GAGGTGCAGC TGGTGGAGTC TGGGGGAGGC TTGATACAGC CTGGGGGGTC CCTGAGACTC
61  TCCTGTGCAA CCTCTGGATT CACCTTTAGA ACTTCTTCCA TGAGTTGGGT CCGTCGGGCT
121 CCAGGGAAGG GGCTGGAATG GGTCTCAGCT ATTGGTGCTG AAAGTCATGA CACGCACTAC
181 ACAGACTCCG CGGAGGGCCG GTTCACCATC TCCAAAGACT ATTCAAAGAA CACAGTATAT
241 CTGCAGATGA ACGGCCTGAG AGTCGACGAC ACGGCCATAT ATTATTGTGC CCATCACTAT
301 TACTATGGCT CGGGCAGAA CCCAAAGAT TGGGAGATG CTTTTGATAT GTGGGGCCAG
361 GGGACAATGG TCTCCGTCTC TTCA       (SEQ ID NO: 73)
```

FIG. 17

```
1   EVQLVESGGG LIQPGGSLRL
21  SCATSGFTFR TSSMSWVRRA  CDR1
41  PGKGLEWVSA IGAESHDTHY  CDR2
61  TDSAEGRFTI SKDYSKNTVY
81  LQMNGLRVDD TAIYYCAHHY  CDR3
101 YYGSRQKPKD WGDAFDMWGQ
121 GTMVSVSS          (SEQ ID NO: 74)
```

FIG. 18

```
  1  GACATCCAGA TGACCCAGTC TCCATCTTCT GTGTCTGCAT CTGTAGGAGA CAGAGTCACC
 61  ATCACTTGTC GGGCGAGTCA GGATATTAGC ACCTGGTTAA CCTGGTATCA GCAGAGAGCA
121  GGGAAGGCCC CTAACCTCCT GATCTATGGT GCATCCACTT TGGAAGATGG GGTCCCATCC
181  AGGTTCAGCG GCAGTGGATC CGGGACAGAT TTCACTCTCA CTATCGACAG CCTGCAGCCT
241  GACGATTTTG CAACTTACTA TTGTCAACAG TCTCACAGTT TCCCCTACAC TTTTGGCCAG
301  GGGACCCAGC TGGGGATCTC A            (SEQ ID NO: 82)
```

FIG. 19

```
  1  DIQMTQSPSS VSASVGDRVT
 21  ITCRASQDIS TWLTWYQQRA  CDR1
 41  GKAPNLLIYG ASTLEDGVPS  CDR2
 61  RFSGSGSGTD FTLTIDSLQP
 81  DDFATYYCQQ SHSFPYTFGQ  CDR3
101  GTQLGIS           (SEQ ID NO: 83)
```

FIG. 20

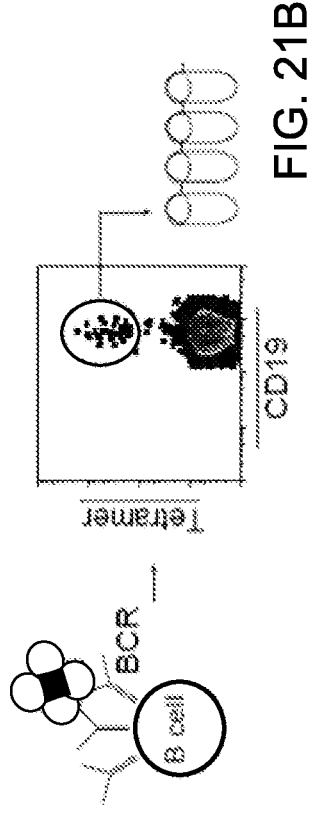
Tetramerization of antigen
FIG. 21A
B cell labeling & single cell sorting
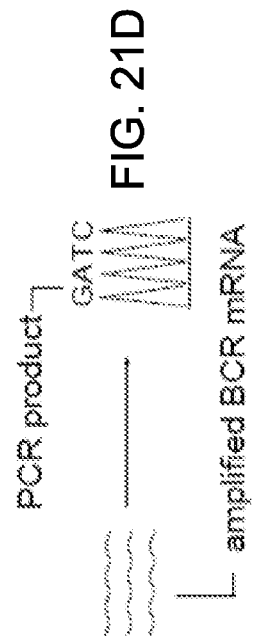
FIG. 21B
T7 mediated mRNA amplification
FIG. 21C
Nested RT-PCR & sequencing
FIG. 21D
Antibody expression
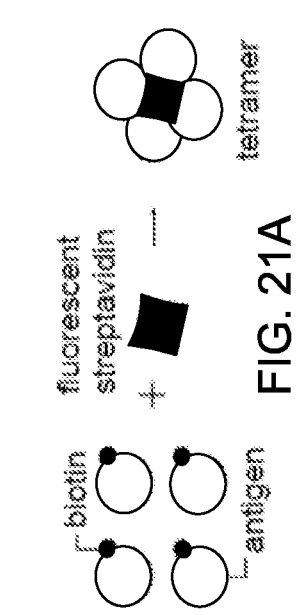
FIG. 21E
Test for activity
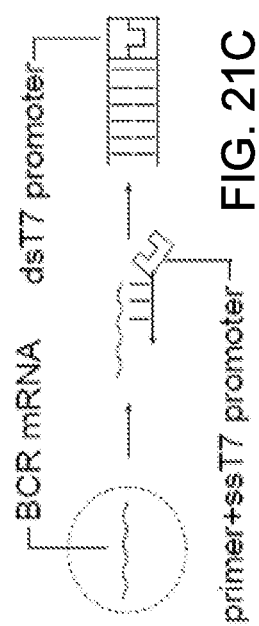
a) ADCC
b) complement activation
c) neutralization
d) crosspresentation
FIG. 21F

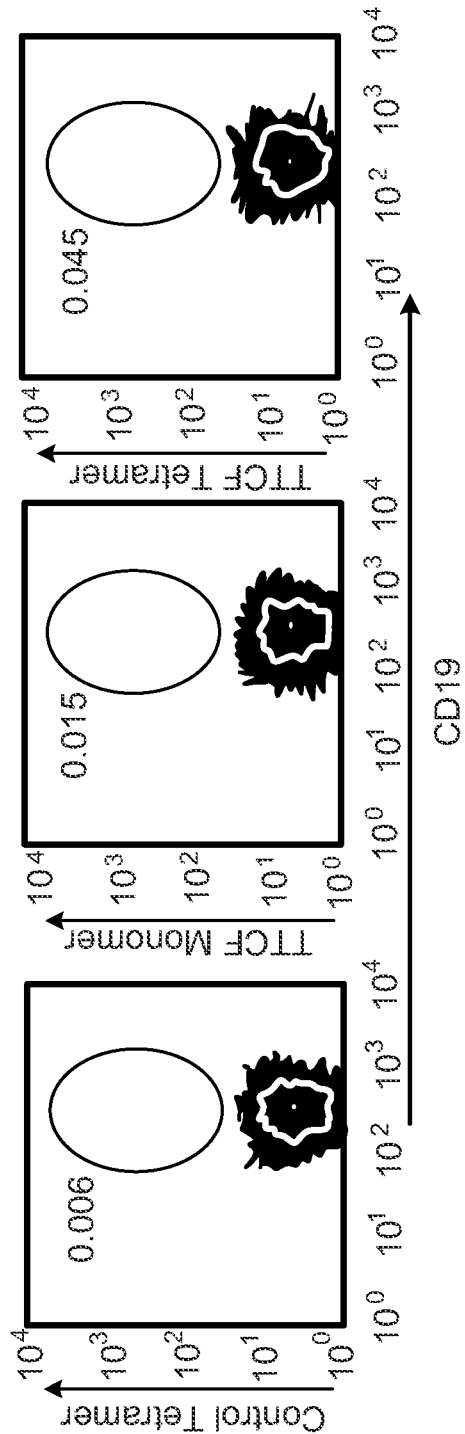

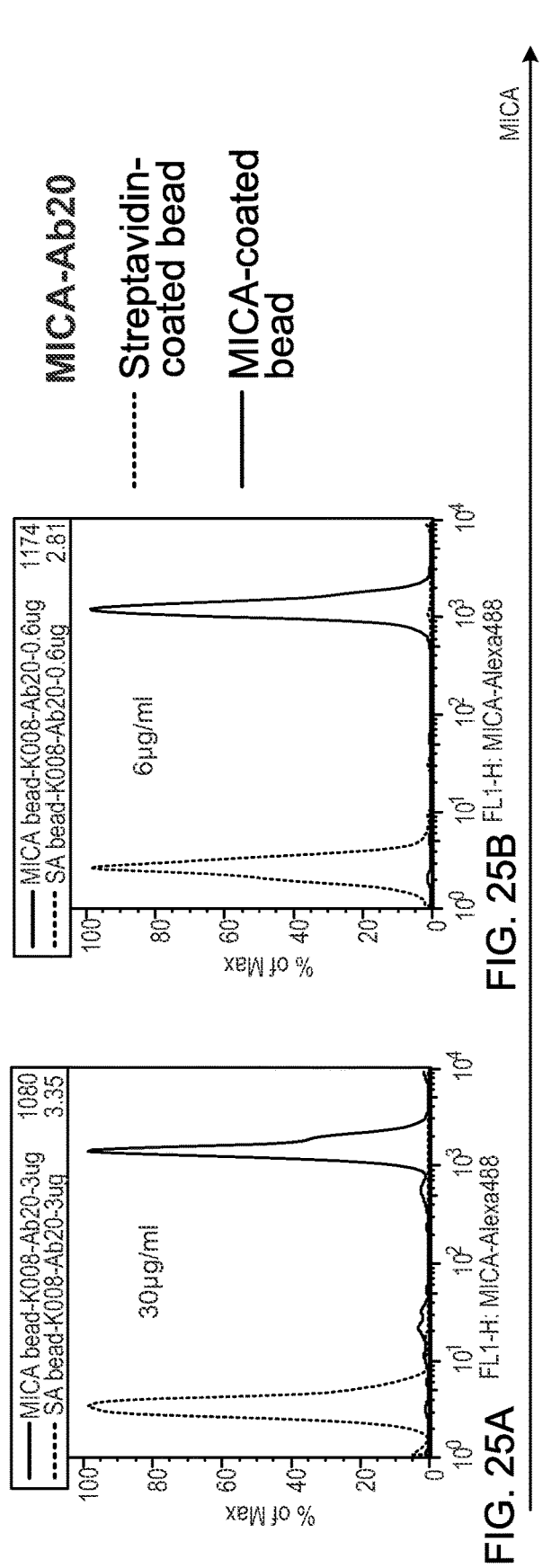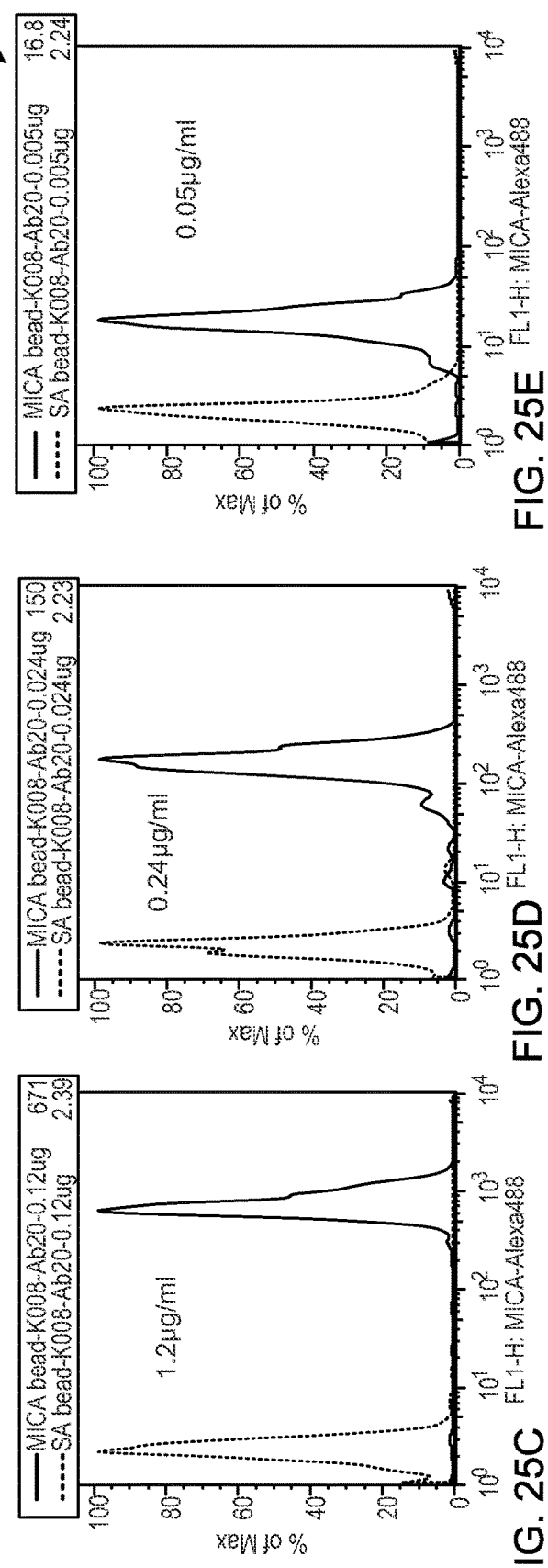

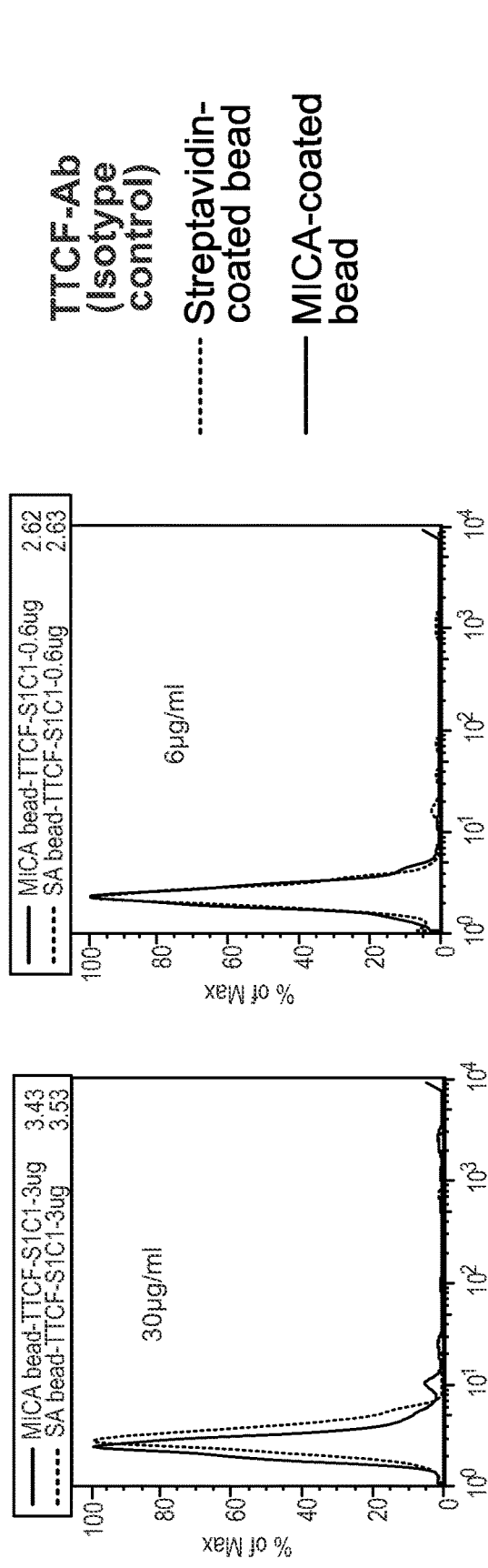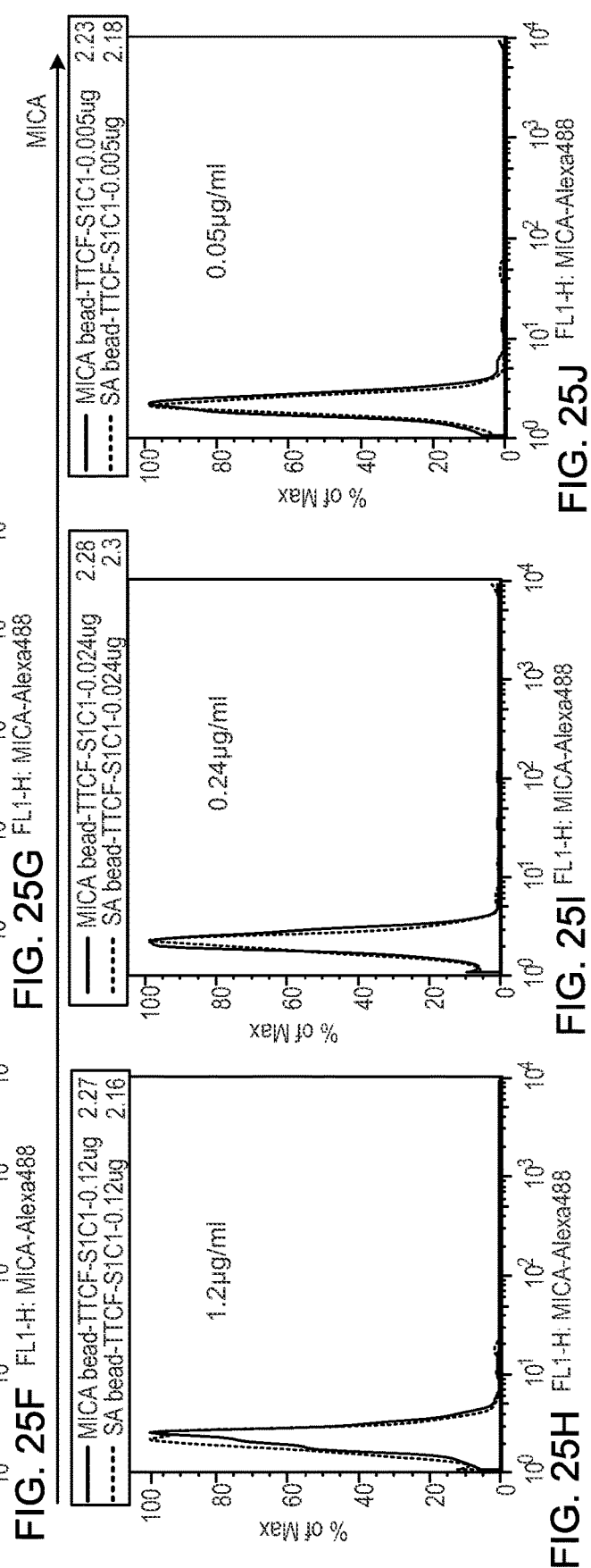

CAGGTGCAGCTGCAGGAGTCGGGCCCAGGACTGGTGGAGCCTTCGGGGACCCTGTCCCT
CACCTGCACTGTGTCTGGTGGCTCCATCAGCAGGAGTAACTGGTGGAGTTGGGTCCGCC
AGCCCCCAGGGGAGGGCTGGAATGGATTGGAGAAATCCATCACATTGGGAGGTCCAGC
TACAATCCGTCCCTCAAGAGTCGAGTCACCATGTCTGTAGACAAGTCCCAGAACCAGTT
CTCCCTGAGGCTGACCTCTGTGACCGCCGCGGACACGGCCGTGTATTACTGTGCGAAAA
ATGGCTACTACGCTATGGACGTCTGGGGCCAAGGGACCACCGTCACCGTCTCCTCG (SEQ ID NO. 148)

FIG. 28

QVQLQESGPGLVEPSGTLSLTCTVSGGSISRSNWWSWVRQPPGEGLEWIGEIHHIGRSS
YNPSLKSRVTMSVDKSQNQFSLRLTSVTAADTAVYYCAKNGYYAMDVWGQGTTVTVSS (SEQ ID NO. 149)

FIG. 29

GAAATTGTGTTGACGCAGTCTCCAGGCACCCTGTCTTTGTCTCCAGGGGAAAGAGCCAC
CCTCTCCTGCAGGGCCAGTCAGAGTGTTAGCAGCGACTTCCTAGCCTGGTACCAGCAGA
AACCTGGCCAGGCTCCCAGGCTCCTCATCTACGCTACATCCTTCAGGCCACTGGCATC
TCAGACAGGTTCAGTGGCAGTGGGTCTGGGACAGACTTCTCTCTCACCATCAACAGACT
GGAACCTGAAGATTTTGCAGTGTATTACTGTCAGCACTATCGTAGTTCACCTCCGTGGT
ACACTTTTTGCCCAGGGGACCAAGCTGGACATGAGACGTACGGTGGCTGCACCATCTGTC
(SEQ ID NO. 150)

FIG. 30

EIVLTQSPGTLSLSPGERATLSCRASQSVSSDFLAWYQQKPGQAPRLLIYATSFRATGI
SDRFSGSGSGTDFSLTINRLEPEDFAVYYCQHYRSSPPWYTFAQGTKLDMRRTVAAPSV
(SEQ ID NO. 151)

FIG. 31

CAGGTGCAGCTGCAGGAGTCGGGCCCAGGACTGGTGAAGCCTTCGGGGACCCTGTCCCTC
ACCTGCGCTGTCTCTGGTGCCTCCATTACCAATGGTGCTGGAGTTGGGTCCGCCAG
CCCCCAGGGAAGGGGCTGGAGTGGATTGGAGAAATCTATCTTAATGGAACACCAACTCC
AACCCGTCCCTGAAGAGTCGAGTCATCATATCAGTGGACAAGTCCAAGAACCACTCTCG
CTGACCCTGAACTCTGTGACCGCCGCGGACACGGCCGTGTATTACTGTGCGAAGAACGCT
GCCTACAACCTTGAGTTCTGGGGCCAGGGAGCCCTGGTCACCGTCTCCTCA (SEQ ID NO: 167)

FIG. 32

QVQLQESGPGLVKPSGTLSLTCAVSGASITNGAWWSWVRQPPGKGLEWIGEIYLNGNTNS
NPSLKSRVIISVDKSKNHFSLTLNSVTAADTAVYYCAKNAAYNLEFWGQGALVTVSS (SEQ
ID NO: 168)

FIG. 33

GAAATTGTGTTGACGCAGTCTCCAGGCACCCTGTCTTTGTCTCCAGGGGAAAGAGCCACC
CTCTCCTGCAGGGCCAGTCAGACTGTTAGCCCCTAGCCTGGTACCAGCAGAAA
CGTGGCCAGGCTCCCAGGCTCCTCATCTATGGTGCATCCAGGGCCACCGGCATCCCAG
ACAGGTTCAGTGGCAGTGGGTCTGGGACAGACTTCACTCTCACCATCAGCAGACTGGAGC
CTGAAGATTTTGCAGTGTATTACTGTCAGCAGTATGATAGATCATATTACACTTT
GGCCAGGGGACCAAGCTGGAGATCAAA (SEQ ID NO: 169)

FIG. 34

EIVLTQSPGTLSLSPGERATLSCRASQTVSSPYVAWYQQKRGQAPRLLIYGASTRATGIPDR
FSGSGSGTDFTLTISRLEPEDFAVYYCQQYDRSYYTFGQGTKLEIK (SEQ ID NO: 170)

FIG. 35

CAGGTGCAGCTGCAGGAGTCGGGGGGCCCAGGACTGGTGAAGCCTTGGGAGAACCTGTCGCTC
ACCTGCACTGTCTCTGATGCCTCCATGAGTGATTATCACTGAGCTGGATCCGGCAGGCC
GCCGGGAAGGGACTGGAGTGGATTGGGGGTATGTACAGCACTGGAGTCCTACTACAA
ACCCTCCCTCAAAGGTCGGGTCACCATGTCAATAGACACGTCCAAGAACCAGTTCTCCCT
GAAGCTGGCCTCTGTGACCGCCGAGACACGGCCATCTATTATTGTGCGAGCGGACAACA
TATTGGTGGCTGGGTCCCCCCTGACTTCTGTGGGCCAGGGAACCCTGGTCACCGTCTCCTC
A (SEQ ID NO: 185)

FIG. 36

QVQLQESGPGLVKPSENLSLTCTVSDASMSDYHWSWIRQAAGKGLEWIGRMYSTGSPYY
KPSLKGRVTMSIDTSKNQFSLKLASVTAADTAIYYCASGQHIGGWVPPDFWGQGTLVTVS
S (SEQ ID NO: 186)

FIG. 37

GATATTGTGATGACCCAGACTCCACTCTCCTCACCTGTCACCCTTGGACAGCCGGCCTCCA
TCTCCTGCAGGTCTAGTGAAGGCCTCGTATATAGTGATGGAGACACTTAGTTGAGTTGGT
TTCACCAGAGGCCAGGCCAGCTCCAAGACTCCTGATTTATAAAATTTCTAACCGGTTCT
CTGGGGTCCCCGACAGATTCAGTGGCAGTGGGGCAGGCACAGATTTCACACTGAAAATCA
GCAGGGTGAGGGTGAGGATGTGTCGGGTTTATTACTGCATGCAAGCTACACATTTCCGT
GGACGTTCGGCCAGGGGACCAAAGTGGAAGTGAAACGT (SEQ ID NO: 187)

FIG. 38

DIVMTQTPLSSPVTLGQPASISCRSSEGLVYSDGDTYLSWFHQRPGQPPRLLIYKISNRFSG
VPDRFSGSGAGTDFTLKISRVEAEDVGVYYCMQATHFPWTFGQGTKVEVKR (SEQ ID NO: 188)

FIG. 39

GAGGTGCAGCTGTTGGAGTCTGGGGGAGGCTTGGTACAGCCTGGGGGGTCCCTGAGACTC
TCCTGTGCAGCCTCTGGATTCACCTTTAGTTCATATATGGCTTGACCTGGATACGCCAGGCT
CCGGGGAAGGGCCTGGAGTGGGTCTCAAGTATCAGTGGCAGTGGCAATAACACATACTA
CGCAGACTCTGTGAAGGGCCGGTTCACCATCTCCAGAGACAAAGTCAAGAAGACACTATA
TCTACAAATGGACAGCCTGACAGTCGGAGACACGGCCGTCTATTACTGCTTAGGAGTCGG
TCAGGGCCACGGAATTCCGGTCATGTCTCCTCA (SEQ ID NO. 203)

FIG. 40

EVQLLESGGGLVQPGGSLRLSCAASGFTFSSYGLTWIRQAPGKGLEWVSSISGSGNNTYYA
DSVKGRFTISRDKVKKTLYLQMDSLTVGDTAVYYCLGVGQGHGIPVIVSS (SEQ ID NO. 204)

FIG. 41

GATATTGTGATGACCCAGACTCCACTCTCCTCACTGTCACCCTTGGACAGCCGGCCTCCA
TCTCCTGCAGGTCTAGTCAGAGCCTCGTACACCGTGATGGAAACACCTACTTGAGTTGGT
TTCTGCAGAGGCCAGGCCAGGTCCAAGACTCCTAATTTATCGGATTCTAACCGGTTCT
CTGGGGTCCCAGACAGATTCAGTGGCAGTGGGGCAGGACGGATTTCACACTGAAAATC
AGCAGGGTGGAAGCTGAGGATGTCGGGGTTTACTACTGCATGCAAGCTACACAAATCCCC
AACACTTTTGGCCAGGGGACCAAGCTGGAGATCAAG (SEQ ID NO. 205)

FIG. 42

DIVMTQTPLSSPVTLGQPASISCRSSQSLVHRDGNTYLSWFLQRPGQAPRLLIYRISNRFSG
VPDRFSGSGAGTDFTLKISRVEAEDVGVYYCMQATQIPNTFGQGTKLEIK (SEQ ID NO.
206)

FIG. 43

GAGGTGCAGCTGGTGGAGTCTGGAGGAGGCTTAATCCAGCCGGGGGGTCCCTAAGACT
CTCCTGTGCAGCCTCGGCTTCCTCATCAGTAGTTATTTCATGAGCTGGTCCGCCAGG
CTCCAGGGAAGGGCCGGAGTGGGTCTCAGTTATTTATAGCGATGGTAGTACATATTAC
GTAGACTCCGTGAAGGGCCGATTCACCATCTCCACAGACAATTCCAAGAACACACTATA
TCTTCAGATGAACAGCCTGAGAGCCGAGGACACGGCCCGATATTACTGTGCGACACGGC
ATTTGAATTATGACGGTGACCACTGGGGCCAGGAACCCTGGTCACCGTCTCCTCAGCC
TCCACCAAG (SEQ ID NO: 221)

FIG. 44

EVQLVESGGGLIQPGGSLRLSCAASGFLISSYFMSWVRQAPGKGPEWVSVIYSDGSTYY
VDSVKGRFTISTDNSKNTLYLQMNSLRAEDTARYYCATRHLNYDGDHWGQGTLVTVSSA
STK (SEQ ID NO: 222)

FIG. 45

GATGTTGTGATGACTCAGTCTCCACTCTCCCTGCCCGTCACCCTTGGACAGCCGGCCTC
CATCTCCTGCAGGTCTAGTCAAAGCCTCGTACACAGTGACGGAAACACCTACTTGAATT
GGTTTCACCAGAGGCCAGGCCAATCTCCAAGGCGCCTAATTTATAAGGTTTCTAAGCGG
GACTCTGGGGTCCCAGACAGATTCAGCGGCAGTGGGTCAGTGAGTGATTTCACACTGAA
AATCAGCAGGTGGAGGCTGAGGATGTTGGAATTTATTACTGCATGCAAGGTACACATT
GGCCGACGTTCGGCGGCCAAGGGACCAAGGTGGAAATCAAACGAACTGTGGCTGCA (SEQ
ID NO: 223)

FIG. 46

DVVMTQSPLSLPVTLGQPASISCRSSQSLVHSDGNTYLNWFHQRPGQSPRRLIYKVSKR
DSGVPDRFSGSGSGSDFTLKISRVEAEDVGIYYCMQGTHWPTFGQGTKVEIKRTVAA
(SEQ ID NO: 224)

FIG. 47

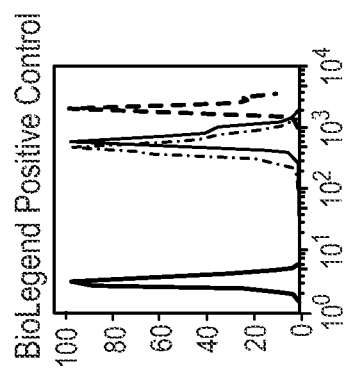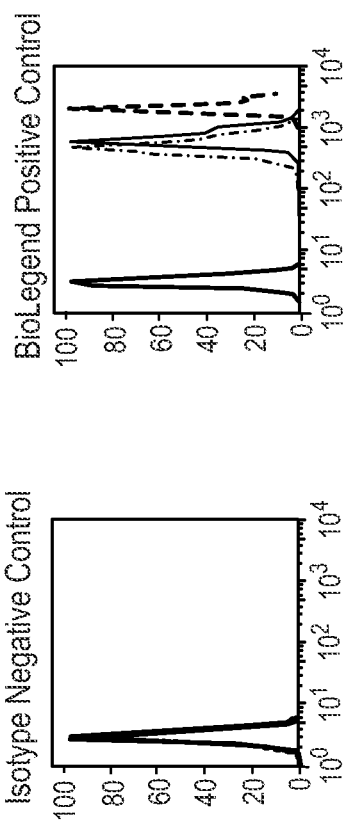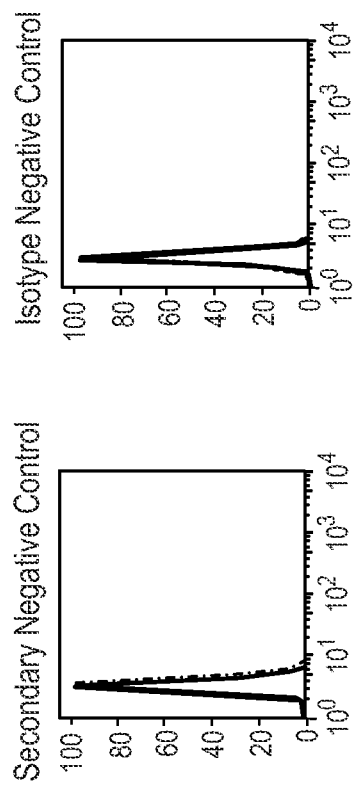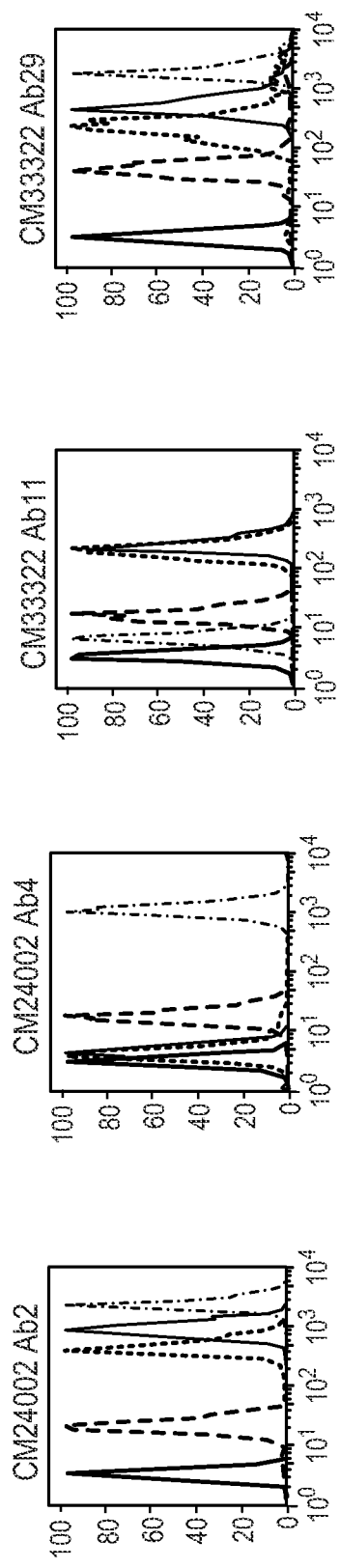

THERAPEUTIC PEPTIDES

CLAIM OF PRIORITY

This application is a continuation of U.S. patent application Ser. No. 14/025,573, filed Sep. 12, 2013, now U.S. Pat. No. 9,402,905, issued Aug. 2, 2016, which is a continuation of International Application No. PCT/US201.2/057839, filed Sep. 28, 2012, which claims the benefit of US Provisional Patent Application Ser. No. 61/541,921, filed on Sep. 30, 2011, the entire contents of which are hereby incorporated by reference.

GOVERNMENT SUPPORT

This invention was made with Government support under Grant No. PO1 AI045757, awarded by the National Institutes of Health. The Government has certain rights in the invention.

SEQUENCE LISTING

The instant application contains a Sequence Listing which has been submitted in ASCII format via EFS-Web and is hereby incorporated by reference in its entirety. Said ASCII copy, created on Jul. 15, 2016 is named 53293WO1.txt and is 90,535 bytes in size.

TECHNICAL FIELD

This invention relates to therapeutic compositions (e.g., peptides) related to human subjects.

BACKGROUND

Human subjects exposed to a condition or disease offer a source of antibodies with therapeutic potential and general methods for obtaining such antibodies are known in the art. However, methods for specifically obtaining antibodies with therapeutic potential are generally limited by the low frequency, slow proliferation rate, and low antibody secretion levels of B cells that express such antibodies. For example, memory B cells with defined specificity typically account for only one cell per million peripheral blood mononuclear cells or approximately one milliliter of blood (Lanzavecchia et al., Curr. Opin. Immunol., 21:298-304 (2009): Yoshida et al., Immunol. Rev., 237:117-139 (2010)). The frequency of antibodies with therapeutic potential is likely to be even lower in cancer patients, necessitating the development of novel approaches that enable isolation of such cells with high sensitivity and efficiency.

Conventional methods generally rely on conversion of memory B cells into antibody secreting cells by in vitro culture and/or use of immunized animal models (e.g., mice) (Crotty et al., J. Immunol., 171:4969-4973 (2003): Fecteau et al., Immunology, 128:e353-e365 (2009): Buisman et al., Vaccine, 28:179-186 (2009): Corti et al., PLoS One, 5:e8805 (2010)). For example, following in vitro culture for up to one week, antibodies can be measured in culture supernatants and frequencies of antibody secreting cells assessing using enzyme-linked immunosorbent spot (ELISPOT) assay. Limitations of such methods are reported (Henn et al., J. Immunol., 183:31777-3187 (2009): Cao et al., J. Immunol., Methods, 358:56-65 (2010)). For instances, in vitro culture of memory B cells alters the memory B cell phenotype to resemble plasma cells with distinct functional properties (Jiang et al., Eur. J. Immunol., 37:2205-2213 (2007): Huggins et al., Blood, 109:1611-1619 (2007): Jourdan et al., Blood, 114:5173-5181 (2009)). Limitations for fluorescent antigen-based methods are also reported (Hofer et al., Immunol. Rev., 211:295-302 (2006): Odendahl et al., Blood, 105:1614-1621 (2005); Kunkel et al., Nat. Rev. Immunol., 3:822-829 (2003): Scheid et al., Nature, 458:636-640 (2009): Wu et al., Science, 329:856-861 (2010)).

Improved methods for specifically obtaining or targeting antibodies with therapeutic potential are required.

MICA is a ligand for NKG2D, a C-type lectin-like, type II transmembrane receptor expressed on most human NK cells, γδ T cells, and CD8+ T cells. Upon ligation, NKG2D signals through the adaptor protein DAP10 to evoke perforin dependent cytolysis and to provide co-stimulation. In humans, the NKG2D ligands include MHC class I chain-related protein A (MICA), the closely related MICB, UL-16 binding proteins (ULBP) 1-4, and RAE-1G. While NKG2D ligands are not usually found on healthy tissues, various forms of cellular stress, including DNA damage, may upregulate ligand expression, resulting in their frequent detection in multiple solid and hematologic malignancies, including melanoma. NKG2D activation through ligand positive transformed cells contributes to extrinsic tumor suppression, since NKG2D deficient and wild type mice treated with anti-NKG2D blocking antibodies manifest enhanced tumor susceptibility. Immune escape may be achieved in patients, however, by the shedding of NKG2D ligands from tumor cells, which triggers internalization of surface NKG2D and impaired function of cytotoxic lymphocytes. Soluble NKG2D ligands may also stimulate the expansion of regulatory NKG2D+CD4+Foxp3-T cells that may antagonize anti-tumor cytotoxicity through Fas ligand, IL-10, and TGF-β. MICA is a NKG2D ligand shed from tumor cells, i.e., released from the cell surface into the surrounding medium, and sera from cancer patients typically contain elevated levels of the soluble form (sMICA). MICA shedding is accomplished in part through interactions with the protein disulfide isomerase ERp5, which forms a disulfide bond with a critical cysteine that results in unfolding of the α3 domain, rendering it susceptible to protcolysis by ADAM-10/17 and MMP14.

Angiogenesis is the process of forming new capillaries from preexisting blood vessels and has been implicated as a critical part of tumor growth and dissemination. Tumors stimulate angiogenesis to meet increasing oxygen and nutrient requirements that exceed those that can be met by diffusion alone. Consequently, tumors recruit, remodel and expand existing vascular to meet their metabolic demand. The dependence of growing tumors on new blood vessel formation has made angiogenesis an appealing target for anti-cancer therapies. Many cytokines have been are believed to play a role in the regulation of angiogenesis, including vascular endothelial growth factor (VEGF) family members and the angiopoietins. The angiopioetins were discovered as ligands for the Ties, a family of tyrosine kinases that is selectively expressed in the vascular endothelium. There are four know angiopoietins: angiopoietin-1 ("Ang-1") through angiopoietin-4 ("Ang-4"). Studies have suggested that angiopoietins (e.g., Ang-1 and Ang-2) may be involved and tumor angiogenesis. With this information, angiopoietins have been identified as potential targets of immune-based cancer therapy.

There is a need to identify new agents that specifically recognize and bind targets of immune-based cancer therapy, such as MICA and angiopoietins. Such agents would be useful for diagnostic screening and therapeutic intervention in disease states that are associated with tumor development.

SUMMARY

The present disclosure provides compositions and methods related to antibodies with therapeutic potential.

In some embodiments, the disclosure provides compositions comprising peptides that immunospecifically bind to MHC class I polypeptide-related sequence A (MICA), or an epitope thereon. In some aspects, peptides of the compositions include complementarity determining region (CDR) 3 of the $V_H$ of antibody ID 1, 6, 7, 8 or 9 shown in Table 1 having 5 or fewer conservative amino acid substitutions, and CDR3 of the $V_L$ of antibody ID 1, 6, 7, 8 or 9 shown in Table 1 having 5 or fewer conservative amino acid substitutions. In some aspects, such peptides include complementarity determining region (CDR) 3 of the $V_H$ of antibody ID 1, 6, 7, 8 or 9 shown in Table 1, and CDR3 of the $V_L$ of antibody ID 1, 6, 7, 8 or 9 shown in Table 1. In some aspects, peptides further include CDR2 of the $V_H$ of antibody ID 1, 6, 7, 8 or 9 shown in Table 1 having 5 or fewer conservative amino acid substitutions, or CDR2 of the $V_L$ of antibody ID 1, 6, 7, 8 or 9 shown in Table 1 having 5 or fewer conservative amino acid substitutions, or both. In some aspects, such peptides include complementarity determining region CDR2 of the $V_H$ of antibody ID 1, 6, 7, 8 or 9 shown in Table 1, or CDR2 of the $V_L$ of antibody ID 1, 6, 7, 8 or 9 shown in Table 1, or both. In some aspects, peptides further include CDR1 of the $V_H$ of antibody ID 1, 6, 7, 8 or 9 shown in Table 1 having 5 or fewer conservative amino acid substitutions, or CDR1 of the $V_L$ of antibody ID 1, 6, 7, 8 or 9 shown in Table 1 having 5 or fewer conservative amino acid substitutions, or both. In some aspects, such peptides include complementarity determining region CDR1 of the $V_H$ of antibody ID 1, 6, 7, 8 or 9 shown in Table 1, or CDR1 of the $V_L$ of antibody ID 1, 6, 7, 8 or 9 shown in Table 1, or both.

In some aspects, peptides are antibody or antibody fragment that include: a $V_H$ chain with identity to SEQ ID NO:2, wherein regions corresponding to CDR1, CDR2, and CDR3 comprise CDR1, CDR2, and CDR3 of the $V_H$ of antibody ID 1 shown in table 1 having 5 or fewer conservative amino acid substitutions, and regions within SEQ ID NO:2 corresponding to FR1, FR2, FR3, FR4, comprise amino acid sequences with at least 80%, 85%, 90%, 95%, 96%, 97%, 98, 99%, or 100% identity to FR1, FR2, FR3, FR4 of the $V_H$ of antibody ID 1 shown in table 1; and a $V_L$ chain with identity to SEQ ID NO: 11, wherein regions corresponding to CDR1, CDR2, and CDR3 comprise CDR1, CDR2, and CDR3 of the $V_L$ of antibody ID 1 shown in table 1 having 5 or fewer conservative amino acid substitutions, and regions within SEQ ID NO: 11 corresponding to FR1, FR2, FR3, FR4, comprise amino acid sequences with at least 80%, 85%, 90%, 95%, 96%, 97%, 98, 99%, or 100% identity to FR1, FR2, FR3, FR4 of the $V_L$ of antibody ID 1 shown in table 1. In some aspects, peptides include an antibody or antibody fragment comprising a $V_H$ chain comprising SEQ ID NO:2 and a $V_L$ chain comprising SEQ ID NO: 11. In some aspects, in addition the peptides, compositions further include one or more (e.g., 1 2, 3, 4, 5, 6, 7, 8, 9, 10, or less than 20) anti-cancer therapeutics. In some aspects, compositions are formulated as pharmaceutical compositions (e.g., for administration to a subject).

In some aspects, peptides are antibody or antibody fragment that include: a $V_H$ chain with identity to SEQ ID NO:149, wherein regions corresponding to CDR1, CDR2, and CDR3 comprise CDR1, CDR2, and CDR3 of the $V_H$ of antibody ID 6 shown in table 1 having 5 or fewer conservative amino acid substitutions within the CDR1, CDR2, and CDR3 regions, and regions within SEQ ID NO:149 corresponding to FR1, FR2, FR3, FR4, comprise amino acid sequences with at least 80%, 85%, 90%, 95%, 96%, 97%, 98, 99%, or 100% identity to FR1, FR2, FR3, FR4 of the $V_H$ of antibody ID 6 shown in table 1; and a $V_L$ chain with identity to SEQ ID NO: 151, wherein regions corresponding to CDR1, CDR2, and CDR3 comprise CDR1, CDR2, and CDR3 of the $V_L$ of antibody ID 6 shown in table 1 having 5 or fewer conservative amino acid substitutions within the CDR1, CDR2, and CDR3 regions, and regions within SEQ ID NO: 151 corresponding to FR1, FR2, FR3, FR4, comprise amino acid sequences with at least 80%, 85%, 90%, 95%, 96%, 97%, 98, 99%, or 100% identity to FR1, FR2, FR3, FR4 of the $V_L$ of antibody ID 6 shown in table 1. In some aspects, peptides include an antibody or antibody fragment comprising a $V_H$ chain comprising SEQ ID NO: 149 and a $V_L$ chain comprising SEQ ID NO:151. In some aspects, in addition the peptides, compositions further include one or more (e.g., 1 2, 3, 4, 5, 6, 7, 8, 9, 10, or less than 20) anti-cancer therapeutics. In some aspects, compositions are formulated as pharmaceutical compositions (e.g., for administration to a subject).

In some aspects, peptides are antibody or antibody fragment that include: a $V_H$ chain with identity to SEQ ID NO: 168, wherein regions corresponding to CDR1, CDR2, and CDR3 comprise CDR1, CDR2, and CDR3 of the $V_H$ of antibody ID 7 shown in table 1 having 5 or fewer conservative amino acid substitutions within the CDR1, CDR2, and CDR3 regions, and regions within SEQ ID NO: 168 corresponding to FR1, FR2, FR3, FR4, comprise amino acid sequences with at least 80%, 85%, 90%, 95%, 96%, 97%, 98, 99%, or 100% identity to FR1, FR2, FR3, FR4 of the $V_H$ of antibody ID 7 shown in table 1; and a $V_L$ chain with identity to SEQ ID NO:170, wherein regions corresponding to CDR1, CDR2, and CDR3 comprise CDR1, CDR2, and CDR3 of the $V_L$ of antibody ID 7 shown in table 1 having 5 or fewer conservative amino acid substitutions within the CDR1, CDR2, and CDR3 regions, and regions within SEQ ID NO: 170 corresponding to FR1, FR2, FR3, FR4, comprise amino acid sequences with at least 80%, 85%, 90%, 95%, 96%, 97%, 98, 99%, or 100% identity to FR1, FR2, FR3, FR4 of the $V_L$ of antibody ID 7 shown in table 1. In some aspects, peptides include an antibody or antibody fragment comprising a $V_H$ chain comprising SEQ ID NO:168 and a $V_L$ chain comprising SEQ ID NO: 170. In some aspects, in addition the peptides, compositions further include one or more (e.g., 1 2, 3, 4, 5, 6, 7, 8, 9, 10, or less than 20) anti-cancer therapeutics. In some aspects, compositions are formulated as pharmaceutical compositions (e.g., for administration to a subject).

In some aspects, peptides are antibody or antibody fragment that include: a $V_H$ chain with identity to SEQ ID NO:186, wherein regions corresponding to CDR1, CDR2, and CDR3 comprise CDR1, CDR2, and CDR3 of the $V_H$ of antibody ID 8 shown in table 1 having 5 or fewer conservative amino acid substitutions within the CDR1, CDR2, and CDR3 regions, and regions within SEQ ID NO: 186 corresponding to FR1, FR2, FR3, FR4, comprise amino acid sequences with at least 80%, 85%, 90%, 95%, 96%, 97%, 98, 99%, or 100% identity to FR1, FR2, FR3, FR4 of the $V_H$ of antibody ID 8 shown in table 1; and a $V_L$ chain with identity to SEQ ID NO: 188, wherein regions corresponding to CDR1, CDR2, and CDR3 comprise CDR1, CDR2, and CDR3 of the $V_L$ of antibody ID 8 shown in table 1 having 5 or fewer conservative amino acid substitutions within the CDR1, CDR2, and CDR3 regions, and regions within SEQ ID NO:188 corresponding to FR1, FR2, FR3, FR4, comprise amino acid sequences with at least 80%, 85%, 90%, 95%, 96%, 97%, 98, 99%, or 100% identity to FR1, FR2, FR3, FR4 of the $V_L$ of antibody ID 8 shown in table 1. In some aspects, peptides include an antibody or antibody fragment comprising a $V_H$ chain comprising SEQ ID NO: 186 and a $V_L$ chain comprising SEQ ID NO:188. In some aspects, in addition the peptides, compositions further include one or more (e.g., 1 2, 3, 4, 5, 6, 7, 8, 9, 10, or less than 20) anti-cancer therapeutics. In some aspects, compositions are formulated as pharmaceutical compositions (e.g., for administration to a subject).

In some aspects, peptides are antibody or antibody fragment that include: a $V_H$ chain with identity to SEQ ID NO:204, wherein regions corresponding to CDR1, CDR2, and CDR3 comprise CDR1, CDR2, and CDR3 of the $V_H$ of antibody ID 9 shown in table 1 having 5 or fewer conservative amino acid substitutions within the CDR1, CDR2, and CDR3 regions, and regions within SEQ ID NO:204 corresponding to FR1, FR2, FR3, FR4, comprise amino acid sequences with at least 80%, 85%, 90%, 95%, 96%, 97%, 98, 99%, or 100% identity to FR1, FR2, FR3, FR4 of the $V_L$ of antibody ID 9 shown in table 1; and a $V_L$ chain with identity to SEQ ID NO:206, wherein regions corresponding to CDR1, CDR2, and CDR3 comprise CDR1, CDR2, and CDR3 of the $V_L$ of antibody ID 9 shown in table 1 having 5 or fewer conservative amino acid substitutions within the CDR1, CDR2, and CDR3 regions, and regions within SEQ ID NO:206 corresponding to FR1, FR2, FR3, FR4, comprise amino acid sequences with at least 80%, 85%, 90%, 95%, 96%, 97%, 98, 99%, or 100% identity to FR1, FR2, FR3, FR4 of the $V_L$ of antibody ID 9 shown in table 1. In some aspects, peptides include an antibody or antibody fragment comprising a $V_H$ chain comprising SEQ ID NO:204 and a $V_L$ chain comprising SEQ ID NO:206. In some aspects, in addition the peptides, compositions further include one or more (e.g., 1 2, 3, 4, 5, 6, 7, 8, 9, 10, or less than 20) anti-cancer therapeutics. In some aspects, compositions are formulated as pharmaceutical compositions (e.g., for administration to a subject).

In some embodiments, the disclosure provides compositions that include one or more peptides that bind to angiopoietin or an epitope thereon. In some aspects, peptides of the compositions include complementarity determining region (CDR) 3 of the $V_H$ of antibody ID 2, 3, 4, 5 or 10 shown in Table 1 having 5 or fewer conservative amino acid substitutions, and CDR3 of the $V_L$ of antibody ID 2, 3, 4 5 or 10 shown in Table 1 having 5 or fewer conservative amino acid substitutions within the CDR1, CDR2, and CDR3 regions. In some aspects, peptides can include complementarity determining region (CDR) 3 of the $V_H$ of antibody ID 2, 3, 4 or 5 or 10 shown in Table 1, and CDR3 of the $V_L$ of antibody ID 2, 3, 4 or 5 or 10 shown in Table 1. In some aspects, peptides can further include CDR2 of the $V_H$ of antibody ID 2, 3, 4 or 5 or 10 shown in Table 1 having 5 or fewer conservative amino acid substitutions, or CDR2 of the $V_L$ of antibody ID 2, 3, 4 or 5 or 10 shown in Table 1 having 5 or fewer conservative amino acid substitutions, or both. In some aspects, such peptides can include complementarity determining region CDR2 of the $V_H$ of antibody ID 2, 3, 4 or 5 or 10 shown in Table 1, or CDR2 of the $V_L$ of antibody ID 2, 3, 4 or 5 or 10 shown in Table 1, or both. In some aspects, peptides can further include CDR1 of the $V_H$ of antibody ID 2, 3, 4 or 5 or 10 shown in Table 1 having 5 or fewer conservative amino acid substitutions, or CDR1 of the $V_L$ of antibody ID 2, 3, 4, or 5 shown in Table 1 having 5 or fewer conservative amino acid substitutions, or both. In some aspects, such peptides can include complementarity determining region CDR1 of the $V_H$ of antibody ID 2, 3, 4 or 5 or 10 shown in Table 1, or CDR1 of the $V_L$ of antibody ID 2, 3, 4 or 5 or 10 shown in Table 1, or both.

In some aspects, peptides include an antibody or antibody fragment comprising: a $V_H$ chain with identity to SEQ ID NO:20, wherein regions corresponding to CDR1, CDR2, and CDR3 comprise CDR1, CDR2, and CDR3 of the $V_H$ of antibody ID 2 shown in table 1 having 5 or fewer conservative amino acid substitutions within the CDR1, CDR2, and CDR3 regions, and regions within SEQ ID NO:20 corresponding to FR1, FR2, FR3, FR4, comprise amino acid sequences with at least 80%, 85%, 90%, 95%, 96%, 97%, 98, 99%, or 100% identity to FR1, FR2, FR3, FR4 of the $V_H$ of antibody ID 2 shown in table 1; and a $V_L$ chain with identity to SEQ ID NO:29, wherein regions corresponding to CDR1, CDR2, and CDR3 comprise CDR1, CDR2, and CDR3 of the $V_L$ of antibody ID 2 shown in table 1 having 5 or fewer conservative amino acid substitutions within the CDR1, CDR2, and CDR3 regions, and regions within SEQ ID NO:29 corresponding to FR1, FR2, FR3, FR4, comprise amino acid sequences with at least 80%, 85%, 90%, 95%, 96%, 97%, 98, 99%, or 100% identity to FR1, FR2, FR3, FR4 of the $V_L$ of antibody ID 2 shown in table 1. In some aspects, the peptides include an antibody or antibody fragment comprising a $V_H$ chain comprising SEQ ID NO:20 and a $V_L$ chain comprising SEQ ID NO:29.

In some aspects, the peptides an antibody or antibody fragment comprising: a $V_H$ chain with identity to SEQ ID NO:38, wherein regions corresponding to CDR1, CDR2, and CDR3 comprise CDR1, CDR2, and CDR3 of the $V_H$ of antibody ID 3 shown in table 1 having 5 or fewer conservative amino acid substitutions within the CDR1, CDR2, and CDR3 regions, and regions within SEQ ID NO:38 corresponding to FR1, FR2, FR3, FR4, comprise amino acid sequences with at least 80%, 85%, 90%, 95%, 96%, 97%, 98, 99%, or 100% identity to FR1, FR2, FR3, FR4 of the $V_H$ of antibody ID 3 shown in table 1; and a $V_L$ chain with identity to SEQ ID NO:47, wherein regions corresponding to CDR1, CDR2, and CDR3 comprise CDR1, CDR2, and CDR3 of the $V_L$ of antibody ID 3 shown in table 1 having 5 or fewer conservative amino acid substitutions within the CDR1, CDR2, and CDR3 regions, and regions within SEQ ID NO:47 corresponding to FR1, FR2, FR3, FR4, comprise amino acid sequences with at least 80%, 85%, 90%, 95%, 96%, 97%, 98, 99%, or 100% identity to FR1, FR2, FR3, FR4 of the $V_L$ of antibody ID 3 shown in table 1. In some aspects, peptides include an antibody or antibody fragment comprising a $V_H$ chain comprising SEQ ID NO:38 and a $V_L$ chain comprising SEQ ID NO:47.

In some aspects, peptides include an antibody or antibody fragment comprising: a $V_H$ chain with identity to SEQ ID NO:56, wherein regions corresponding to CDR1, CDR2, and CDR3 comprise CDR1, CDR2, and CDR3 of the $V_H$ of antibody ID 4 shown in table 1 having 5 or fewer conservative amino acid substitutions within the CDR1, CDR2, and CDR3 regions, and regions within SEQ ID NO:56 corresponding to FR1, FR2, FR3, FR4, comprise amino acid sequences with at least 80%, 85%, 90%, 95%, 96%, 97%, 98, 99%, or 100% identity to FR1, FR2, FR3, FR4 of the $V_H$ of antibody ID 4 shown in table 1; and a $V_L$ chain with identity to SEQ ID NO:65, wherein regions corresponding to CDR1, CDR2, and CDR3 comprise CDR1, CDR2, and CDR3 of the $V_L$ of antibody ID 4 shown in table 1 having 5 or fewer conservative amino acid substitutions within the CDR1, CDR2, and CDR3 regions, and regions within SEQ ID NO:65 corresponding to FR1, FR2, FR3, FR4, comprise amino acid sequences with at least 80%, 85%, 90%, 95%, 96%, 97%, 98, 99%, or 100% identity to FR1, FR2, FR3, FR4 of the $V_L$ of antibody ID 4 shown in table 1. In some aspects, peptides include an antibody or antibody fragment comprising a $V_H$ chain comprising SEQ ID NO:56 and a $V_L$ chain comprising SEQ ID NO:65.

In some aspects, peptides include an antibody or antibody fragment comprising: a $V_H$ chain with identity to SEQ ID NO:74, wherein regions corresponding to CDR1, CDR2, and CDR3 comprise CDR1, CDR2, and CDR3 of the $V_H$ of antibody ID 5 shown in table 1 having 5 or fewer conservative amino acid substitutions within the CDR1, CDR2, and CDR3 regions, and regions within SEQ ID NO:74 corresponding to FR1, FR2, FR3, FR4, comprise amino acid sequences with at least 80%, 85%, 90%, 95%, 96%, 97%, 98, 99%, or 100% identity to FR1, FR2, FR3, FR4 of the $V_H$ of antibody ID 5 shown in table 1; and a $V_L$ chain with identity to SEQ ID NO:83, wherein regions corresponding to CDR1, CDR2, and CDR3 comprise CDR1, CDR2, and CDR3 of the $V_L$ of antibody ID 5 shown in table 1 having 5 or fewer conservative amino acid substitutions within the CDR1, CDR2, and CDR3 regions, and regions within SEQ ID NO:83 corresponding to FR1, FR2, FR3, FR4, comprise amino acid sequences with at least 80%, 85%, 90%, 95%, 96%, 97%, 98, 99%, or 100% identity to FR1, FR2, FR3, FR4 of the $V_L$ of antibody ID 5 shown in table 1. In some aspects, the peptides include an antibody or antibody fragment comprising a $V_H$ chain comprising SEQ ID NO:74 and a $V_L$ chain comprising SEQ ID NO:83. In some aspects, the peptides immunospecifically bind to at least angiopoietin-2. In some aspects, the compositions further include one or more anti-cancer therapeutics. In some aspects, the compositions are formulated as a pharmaceutical composition.

In some aspects, peptides include an antibody or antibody fragment comprising: a $V_H$ chain with identity to SEQ ID NO:222, wherein regions corresponding to CDR1, CDR2, and CDR3 comprise CDR1, CDR2, and CDR3 of the $V_H$ of antibody ID 10 shown in table 1 having 5 or fewer conservative amino acid substitutions within the CDR1, CDR2, and CDR3 regions, and regions within SEQ ID NO:222 corresponding to FR1, FR2, FR3, FR4, comprise amino acid sequences with at least 80%, 85%, 90%, 95%, 96%, 97%, 98, 99%, or 100% identity to FR1, FR2, FR3, FR4 of the $V_H$ of antibody ID 10 shown in table 1; and a $V_L$ chain with identity to SEQ ID NO:224, wherein regions corresponding to CDR1, CDR2, and CDR3 comprise CDR1, CDR2, and CDR3 of the $V_L$ of antibody ID 10 shown in table 1 having 5 or fewer conservative amino acid substitutions within the CDR1, CDR2, and CDR3 regions, and regions within SEQ ID NO:224 corresponding to FR1, FR2, FR3, FR4, comprise amino acid sequences with at least 80%, 85%, 90%, 95%, 96%, 97%, 98, 99%, or 100% identity to FR1, FR2, FR3, FR4 of the $V_L$ of antibody ID 10 shown in table 1. In some aspects, the peptides include an antibody or antibody fragment comprising a $V_H$ chain comprising SEQ ID NO:222 and a $V_L$ chain comprising SEQ ID NO:224. In some aspects, the peptides immunospecifically bind to at least angiopoietin-2. In some aspects, the compositions further include one or more anti-cancer therapeutics. In some aspects, the compositions are formulated as a pharmaceutical composition.

In some embodiments, the disclosure includes methods of treating cancer in a subject. In some aspects, methods include administering to a subject a composition of any one of claims 1-27.

The present disclosure also provides methods of isolating human antibodies from cancer patients following immunotherapy.

In some embodiments, the disclosure includes method of obtaining immune cells directed against a self antigen from a subject, the method comprising identifying a subject exhibiting a positive immune response towards the self antigen, providing a multimeric form of the self antigen, contacting the multimeric form of the self antigen with a sample from the subject exhibiting a positive immune response towards the self antigen, and obtaining immune cells bound to the multimeric form of the self antigen.

In some embodiments, the disclosure includes method of obtaining immune cells from a cancer patient directed against a self antigen, the method comprising identifying a subject exhibiting a positive immune response towards the self antigen; providing a multimeric form of the self antigen; contacting the multimeric form of the self antigen with a sample from the subject exhibiting a positive immune response towards the self antigen; and obtaining immune cells bound to the multimeric form of the self antigen.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 1|Nucleic acid sequence of the variable heavy ($V_H$) chain of antibody ID 1 (anti-MHC class I polypeptide-related sequence A (MICA) antibody) (SEQ ID NO: 1).

FIG. 2|Amino acid sequence of $V_H$ chain of antibody ID 1 (anti-MICA antibody) (SEQ ID NO:2).

FIG. 3|Nucleic acid sequence of the variable light ($V_L$) chain of antibody ID 1 (anti-MICA antibody) (SEQ ID NO: 10).

FIG. 4|Amino acid sequence of $V_L$ chain of antibody ID 1 (anti-MICA antibody) (SEQ ID NO:11).

FIG. 5|Nucleic acid sequence of the $V_H$ chain of antibody ID 2 (anti-angiopoietin-2 antibody) (SEQ ID NO: 19).

FIG. 6|Amino acid sequence of $V_H$ chain of antibody ID 2 (anti-angiopoietin-2 antibody) (SEQ ID NO:20).

FIG. 7|Nucleic acid sequence of the $V_L$ chain of antibody ID 2 (anti-angiopoietin-2 antibody) (SEQ ID NO:28).

FIG. 8|Amino acid sequence of $V_L$ chain of antibody ID 2 (anti-angiopoietin-2 antibody) (SEQ ID NO:29).

FIG. 9|Nucleic acid sequence of the $V_H$ chain of antibody ID 3 (anti-angiopoietin-2 antibody) (SEQ ID NO:37).

FIG. 10|Amino acid sequence of $V_H$ chain of antibody ID 3 (anti-angiopoietin-2 antibody) (SEQ ID NO:38).

FIG. 11|Nucleic acid sequence of the $V_L$ chain of antibody ID 3 (anti-angiopoietin-2 antibody) (SEQ ID NO:46).

FIG. 12|Amino acid sequence of $V_L$ chain of antibody ID 3 (anti-angiopoietin-2 antibody) (SEQ ID NO:47).

FIG. 13|Nucleic acid sequence of the $V_H$ chain of antibody ID 4 (anti-angiopoietin-2 antibody) (SEQ ID NO:55).

FIG. 14|Amino acid sequence of $V_H$ chain of antibody ID 4 (anti-angiopoietin-2 antibody) (SEQ ID NO:56).

FIG. 15|Nucleic acid sequence of the $V_L$ chain of antibody ID 4 (anti-angiopoietin-2 antibody) (SEQ ID NO:64).

FIG. 16|Amino acid sequence of $V_L$ chain of antibody ID 4 (anti-angiopoietin-2 antibody) (SEQ ID NO:65).

FIG. 17|Nucleic acid sequence of the $V_H$ chain of antibody ID 5 (anti-angiopoietin-2 antibody) (SEQ ID NO:73).

FIG. 18|Amino acid sequence of $V_H$ chain of antibody ID 5 (anti-angiopoietin-2 antibody) (SEQ ID NO:74).

FIG. 19|Nucleic acid sequence of the $V_L$ chain of antibody ID 5 (anti-angiopoietin-2 antibody) (SEQ ID NO:82).

FIG. 20|Amino acid sequence of $V_L$ chain of antibody ID 5 (anti-angiopoietin-2 antibody) (SEQ ID NO:83).

FIG. 21A-21F|Illustrates exemplary methods for making antibodies from B-cells. (A) Antigen is expressed with a BirA tag for site-specific biotinylation and tetramerization with fluorescently-labeled streptavidin. (B) B cells are stained with tetramer and a panel of monoclonal antibodies. Tetramer+, class-switched memory B cells are single-cell sorted into PCR strips. (C) mRNA amplification is performed with T7 RNA polymerase. (D) Sequencing of PCR products is carried out using 300-400 bp PCR products. (E) Overlap PCR is used for construction of full-length IgG1 heavy chain and kappa/lambda light sequences which are cloned into separate vectors. Vectors are transiently transfected into CHO-S cells for expression of fully human recombinant antibodies. (F) Antibodies are tested for antigen binding and assessed for potential therapeutic properties.

FIGS. 22A-22B|Graphs showing comparison of monomeric and tetrameric antigen for identification of memory B cells. (A) Mono-biotinylated TTCF or CD80 antigens were directly labeled with Alexa-488 fluorophore; tetramers were generated with unlabeled streptavidin. Enriched B cells from each donor were split into three fractions and stained with control CD80 tetramer, TTCF monomer, or TTCF tetramer at the same total antigen concentration of 0.125 µg/mL. FACS plots depict CD19+ CD27+ IgM− class-switched memory B cells; numbers adjacent to the gate represent the percentage of the parental gate. (B) Frequencies of tetramer+ memory B cells detected in three different donors. Numbers are calculated as tetramer+ cells per 1×10$^6$ CD19+ memory B cells.

FIGS. 25A-25O|Line graphs showing binding of anti-MICA antibodies to MICA-coated beads.

FIGS. 26A-26D|Bar graphs showing binding of four human angiopoietin 2 specific antibodies as well as a control antibody to three human angiopoietins (angiopoietin-1, 2 and 4) and ang-like-3. Recombinant angiopoietins were immobilized in an ELISA plate and binding of human recombinant antibodies was detected with europium-labeled streptavidin.

FIG. 28|Nucleic acid sequence of the variable heavy ($V_H$) chain of antibody ID 6 (anti-MHC class I polypeptide-related sequence A (MICA) antibody) (SEQ ID NO: 148).

FIG. 29|Amino acid sequence of $V_H$ chain of antibody 6 (anti-MICA antibody) (SEQ ID NO:149).

FIG. 30|Nucleic acid sequence of the variable light ($V_L$) chain of antibody ID 6 (anti-MICA antibody) (SEQ ID NO: 150).

FIG. 31|Amino acid sequence of $V_L$ chain of antibody ID 6 (anti-MICA antibody) (SEQ ID NO: 151).

FIG. 32|Nucleic acid sequence of the variable heavy ($V_H$) chain of antibody ID 7 (anti-MHC class I polypeptide-related sequence A (MICA) antibody) (SEQ ID NO:167).

FIG. 33|Amino acid sequence of $V_H$ chain of antibody ID 7 (anti-MICA antibody) (SEQ ID NO: 168).

FIG. 34|Nucleic acid sequence of the variable light ($V_L$) chain of antibody ID 7 (anti-MICA antibody) (SEQ ID NO:169).

FIG. 35|Amino acid sequence of $V_L$ chain of antibody ID 7 (anti-MICA antibody) (SEQ ID NO: 170).

FIG. 36|Nucleic acid sequence of the variable heavy (VH) chain of antibody ID 8 (anti-MHC class I polypeptide-related sequence A (MICA) antibody) (SEQ ID NO:185).

FIG. 37|Amino acid sequence of VH chain of antibody ID 8 (anti-MICA antibody) (SEQ ID NO: 186).

FIG. 38|Nucleic acid sequence of the variable light (VL) chain of antibody ID 8 (anti-MICA antibody) (SEQ ID NO:187).

FIG. 39|Amino acid sequence of VL chain of antibody ID 8 (anti-MICA antibody) (SEQ ID NO: 188).

FIG. 40|Nucleic acid sequence of the variable heavy ($V_H$) chain of antibody ID 9 (anti-MHC class I polypeptide-related sequence A (MICA) antibody) (SEQ ID NO:203).

FIG. 41|Amino acid sequence of $V_H$ chain of antibody ID 9 (anti-MICA antibody) (SEQ ID NO:204).

FIG. 42|Nucleic acid sequence of the variable light ($V_L$) chain of antibody ID 9 (anti-MICA antibody) (SEQ ID NO:205).

FIG. 43|Amino acid sequence of $V_L$ chain of antibody ID 9 (anti-MICA antibody) (SEQ ID NO: 206).

FIG. 44|Nucleic acid sequence of the $V_H$ chain of antibody ID 10 (anti-angiopoietin-2 antibody) (SEQ ID NO:221).

FIG. 45|Amino acid sequence of $V_H$ chain of antibody ID 10 (anti-angiopoietin-2 antibody) (SEQ ID NO:222).

FIG. 46|Nucleic acid sequence of the $V_L$ chain of antibody ID 10 (anti-angiopoietin-2 antibody) (SEQ ID NO:223).

FIG. 47|Amino acid sequence of $V_L$ chain of antibody ID 10 (anti-angiopoietin-2 antibody) (SEQ ID NO:224).

FIGS. 48A-G|Line graphs showing assessment of MICA allele-specific binding by recombinant anti-MICA antibodies.

DETAILED DESCRIPTION

Figure 23A:
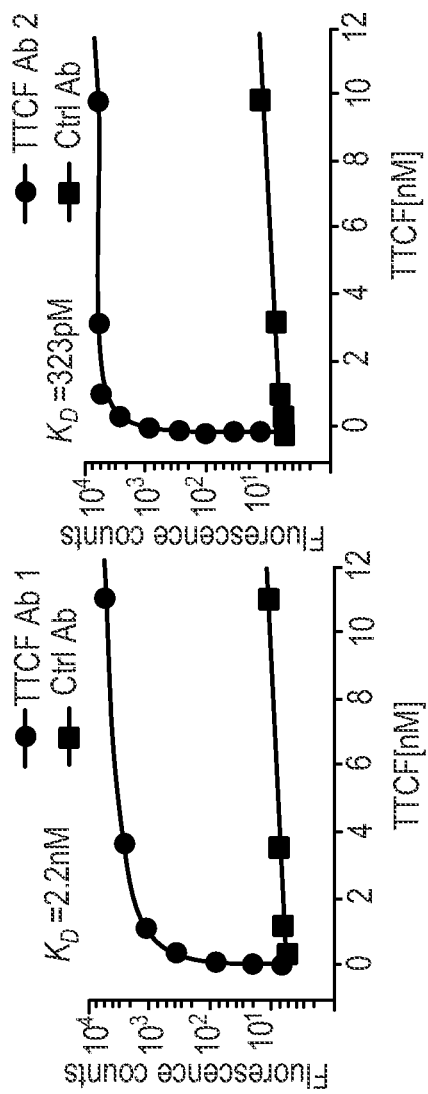
FIGS. 23A-23B|Line graphs showing high affinity binding of TTCF by antibodies generated from plasmablasts and memory B cells. Saturation binding experiments were carried out to determine the affinities of recombinant antibodies. TTCF antigen was labeled with europium, which emits a strong fluorescent signal at 615 nm upon incubation with a chelating reagent. Antibodies were immobilized in a 96-well plate and incubated with TTCF-europium (100 nM to 4 pM) for two hours at 37° C. Fluorescent counts at 615 nm were recorded and $K_D$ calculated using non-linear regression analysis. Control antibody (clone 8.18.C5) that was also produced in CHO-S cells was included in all experiments. (A) Recombinant TTCF Abs 1 and 2 were generated from TTCF tetramer+ plasmablasts (donor 1). (B) TTCF antibodies 3, 4, and 5 originated from TTCF tetramer+ memory B cells of three different donors.

The present disclosure is based, in part, on the observation that antibodies directed against therapeutic targets important in a disease can be obtained from human subjects exposed to the disease by labeling of B cells with a tetrameric form of the antigen of interest. As described in the background section above, prior methods are limited at least in that they are inefficient at identifying appropriate B cells in human subjects and/or because they induce any captured B cells to undergo phenotypic changes, thus reducing their value. In contrast, methods are described herein that allow capture of rare memory B cells directed against specific disease-related antigens. As described below, the methods require tetramerization of the disease-related antigen, which process, as demonstrated in the Examples below, enhances the identification of appropriate memory B cells. Specifically, methods herein permit more efficient capture of appropriate memory B cells for increased periods of time following initial exposure of a subject to the antigen. Methods herein also include antibodies (and peptides generated from the sequences of such antibodies) generated using genetic material obtained from memory B cells captured using the methods disclosed herein.

Described herein are human antibodies against MHC class I polypeptide-related sequence A (MICA) and human antibodies targeted against angiopoietin-2. Both types of human antibodies were identified from patients who had received a cell-based cancer vaccine (GM-CSF transduced autologous tumor cells) by methods that entail the use of tetrameric antigens.

In some instances, the disclosure provides methods for specifically obtaining or targeting antibodies with therapeutic potential from select human subjects and therapeutic compositions resulting therefrom. These methods can include: obtaining or targeting immune cells in a human subject, wherein immune cells include but are not limited to, for example, B cells and/or memory B cells, isolating or purifying genetic material (e.g., DNA and/or mRNA) from the obtained or targeted immune cells, and using the isolated or purified genetic material to produce therapeutic compositions, e.g., therapeutic compositions disclosed herein. Further description of the methods is provided under the section entitled "Methods," below.

In some instances, the disclosure provides therapeutic compositions (e.g., including therapeutic peptides, including antibodies, antibody fragments, antibody derivatives, and/or antibody conjugates) related to antibodies present in subjects that have or had a condition or disease and that exhibited a positive immune response towards the condition or disease.

Therapeutic Compositions

In some instances, therapeutic compositions herein can interact with (e.g., bind, bind specifically and/or bind immunospecifically) binding partners (e.g., an immunogen(s), antigen(s), and/or epitope(s)) related to a disease or condition, wherein interaction between the therapeutic composition and the binding partners results in a positive immune response towards the condition or disease (e.g., a decrease in the level of disease or symptoms thereof in a subject).

In some instances, therapeutic compositions can include peptides that include (e.g., comprise, consist essentially of, or consist of) at least one (e.g., one, two, three, four, five, and/or six) complementarity determining region (CDR) of the variable heavy chain ($V_H$) and/or variable light chain ($V_L$) of antibody ID 1, 2, 3, 4, or 5, 6, 7, 8, 9 or 10, shown in Table 1.

In some instances, therapeutic compositions can include peptides that include (e.g., comprise, consist essentially of, or consist of) at least one (e.g., one, two, three, four, five, and/or six) complementarity determining region (CDR) of the variable heavy chain ($V_H$) and/or variable light chain ($V_L$) of antibody ID 1, 2, 3, 4, 5, 6, 7, 8, 9 or 10, shown in Table 1, and that interact with (e.g., bind, bind specifically and/or bind immunospecifically) to MHC class I polypeptide-related sequence A (MICA (e.g., UniGene Hs.130838)) (e.g., soluble MICA (sMICA)) and/or angiopoietin-2 (e.g., UniGene Hs.583870), including epitopes thereof.

In some instances, therapeutic compositions can include peptides that include at least one CDR of the $V_H$ and/or $V_L$ of antibody ID 1, 6, 7, 8 and/or 9 shown in Table 1, wherein the peptide binds (e.g., binds specifically and/or binds immunospecifically) to MICA (e.g., human MICA (e.g., soluble MICA (sMICA))). In instances, peptides can include at least two CDRs, wherein the at least two CDRs are CDRs shown in Table 1 for different antibodies. In other words, CDRs (and FRs and/or AA sequences) shown in Table 1 for antibodies IDs 1, 6, 7, 8 and 9 are interchangeable and can be combined to generate peptides, so long as the peptides bind (e.g., bind specifically and/or bind immunospecifically) to MICA (e.g., human MICA (e.g., soluble MICA (sMICA))). In some instances, such peptides include CDR3 of the $V_H$ and/or $V_L$ of antibody ID 1, 6, 7, 8 and/or 9 shown in Table 1. In some instances, such peptides include CDR3 of the $V_H$ and $V_L$ of antibody ID 1, 6, 7, 8 and/or 9 and CDR1 and/or CDR2 of the $V_H$ and/or $V_L$ of antibody ID 1, 6, 7, 8 and/or 9 shown in Table 1. In some instances, such peptides include CDR1 CDR2, and CDR3 of the $V_H$ and/or $V_L$ of antibody ID 1, 6, 7, 8 and/or 9. In some instances, such peptides include CDR1, CDR2, and CDR3 of the $V_H$ and/or $V_L$ of antibody ID 1, 6, 7, 8 and/or 9 and at least one of FR1 FR2 FR3, and/or FR4 of the $V_H$ and/or $V_L$ of antibody ID 1, 6, 7, 8 and/or 9, shown in Table 1. In some instances, such peptides include one of SEQ ID NO:2, 149, 168, 186 or 204 and/or one of SEQ ID NO:11, 151, 170, 188, or 206. In each instance, the peptide can bind (e.g., bind specifically and/or bind immunospecifically) to MICA (e.g., human MICA (e.g., soluble MICA (sMICA))). In some instances, the affinity of binding between the peptides and MICA can be between about 0.1 nM to 1 µM, for example, about 10 nM.

In some instances, therapeutic compositions can include peptides that include at least one CDR of the $V_H$ and/or $V_L$ of antibody ID 6 shown in Table 1, wherein the peptide binds (e.g., binds specifically and/or binds immunospecifically) to MICA (e.g., human MICA (e.g., soluble MICA (sMICA))). In some instances, such peptides include CDR3 of the $V_H$ and/or $V_L$ of antibody ID 6 shown in Table 1. In some instances, such peptides include CDR3 of the $V_H$ and $V_1$, of antibody ID 6 and CDR1 and/or CDR2 of the $V_H$ and/or $V_L$ of antibody ID 6 shown in Table 1. In some instances, such peptides include CDR1 CDR2, and CDR3 of the $V_H$ and/or $V_L$ of antibody ID 6. In some instances, such peptides include CDR1, CDR2, and CDR3 of the $V_H$ and/or $V_L$ of antibody ID 6 and at least one of FR1 FR2 FR3, and/or FR4 of the $V_H$ and/or $V_1$, of antibody ID 6, shown in Table 1. In some instances, such peptides include SEQ ID NO: 149 and/or SEQ ID NO: 151. In each instance, the peptide can bind (e.g., bind specifically and/or bind immunospecifically) to MICA (e.g., human MICA (e.g., soluble MICA (sMICA))). In some instances, the affinity of binding between the peptides and MICA can be between about 0.1 nM to 1 µM, for example, about 10 nM.

In some instances, therapeutic compositions can include peptides that include at least one CDR of the $V_H$ and/or $V_L$ of antibody ID 7 shown in Table 1, wherein the peptide binds (e.g., binds specifically and/or binds immunospecifically) to MICA (e.g., human MICA (e.g., soluble MICA (sMICA))). In some instances, such peptides include CDR3 of the $V_H$ and/or $V_L$ of antibody ID 7 shown in Table 1. In some instances, such peptides include CDR3 of the $V_H$ and $V_L$ of antibody ID 7 and CDR1 and/or CDR2 of the $V_H$ and/or $V_L$ of antibody ID 7 shown in Table 1. In some instances, such peptides include CDR1 CDR2, and CDR3 of the $V_H$ and/or $V_L$ of antibody ID 7. In some instances, such peptides include CDR1, CDR2, and CDR3 of the $V_H$ and/or $V_L$ of antibody ID 7 and at least one of FR1 FR2 FR3, and/or FR4 of the $V_H$ and/or $V_L$ of antibody ID 7, shown in Table 1. In some instances, such peptides include SEQ ID NO: 168 and/or SEQ ID NO: 170. In each instance, the peptide can bind (e.g., bind specifically and/or bind immunospecifically) to MICA (e.g., human MICA (e.g., soluble MICA (sMICA))). In some instances, the affinity of binding between the peptides and MICA can be between about 0.1 nM to 1 M, for example, about 10 nM.

In some instances, therapeutic compositions can include peptides that include at least one CDR of the $V_H$ and/or $V_1$, of antibody ID 8 shown in Table 1, wherein the peptide binds (e.g., binds specifically and/or binds immunospecifically) to MICA (e.g., human MICA (e.g., soluble MICA (sMICA))). In some instances, such peptides include CDR3 of the $V_H$ and/or $V_L$ of antibody ID 8 shown in Table 1. In some instances, such peptides include CDR3 of the $V_H$ and $V_L$ of antibody ID 8 and CDR1 and/or CDR2 of the $V_H$ and/or $V_1$, of antibody ID 8 shown in Table 1. In some instances, such peptides include CDR1 CDR2, and CDR3 of the $V_H$ and/or $V_L$ of antibody ID 8. In some instances, such peptides include CDR1, CDR2, and CDR3 of the $V_H$ and/or $V_L$ of antibody ID 8 and at least one of FR1 FR2 FR3, and/or FR4 of the $V_H$ and/or $V_L$ of antibody ID 8, shown in Table 1. In some instances, such peptides include SEQ ID NO: 186 and/or SEQ ID NO: 188. In each instance, the peptide can bind (e.g., bind specifically and/or bind immunospecifically) to MICA (e.g., human MICA (e.g., soluble MICA (sMICA))). In some instances, the affinity of binding between the peptides and MICA can be between about 0.1 nM to 1 µM, for example, about 10 nM.

In some instances, therapeutic compositions can include peptides that include at least one CDR of the $V_H$ and/or $V_L$ of antibody ID 9 shown in Table 1, wherein the peptide binds (e.g., binds specifically and/or binds immunospecifically) to MICA (e.g., human MICA (e.g., soluble MICA (sMICA))). In some instances, such peptides include CDR3 of the $V_H$ and/or $V_L$ of antibody ID 9 shown in Table 1. In some instances, such peptides include CDR3 of the $V_H$ and $V_L$ of antibody ID 9 and CDR1 and/or CDR2 of the $V_H$ and/or $V_L$ of antibody ID 9 shown in Table 1. In some instances, such peptides include CDR1 CDR2, and CDR3 of the $V_H$ and/or $V_L$ of antibody ID 9. In some instances, such peptides include CDR1, CDR2, and CDR3 of the $V_H$ and/or $V_L$ of antibody ID 9 and at least one of FR1 FR2 FR3, and/or FR4 of the $V_H$ and/or $V_L$ of antibody ID 9, shown in Table 1. In some instances, such peptides include SEQ ID NO:204 and/or SEQ ID NO:206. In each instance, the peptide can bind (e.g., bind specifically and/or bind immunospecifically) to MICA (e.g., human MICA (e.g., soluble MICA (sMICA))). In some instances, the affinity of binding between the peptides and MICA can be between about 0.1 nM to 1 M, for example, about 10 nM.

In some instances, therapeutic compositions can include peptides that include at least one CDR of the $V_H$ and/or $V_L$ of antibody ID 2, 3, 4, 5, and/or 10 shown in Table 1, wherein the peptide binds (e.g., binds specifically and/or binds immunospecifically) to angiopoietin-2 (e.g., human angiopoietin-2). In some instances, peptides can include at least two CDRs, wherein the at least two CDRs are CDRs shown in Table 1 for different antibodies. In other words, CDRs (and FRs and/or AA sequences) shown in Table 1 for antibodies IDs 2, 3 4, 5, and 10 are interchangeable and can be combined to generate peptides, so long as the peptides bind (e.g., bind specifically and/or bind immunospecifically) to angiopoietin-2 (e.g., human angiopoietin-2). In some instances, such peptides include CDR3 of the $V_H$ and/or $V_L$ of antibody ID 2, 3, 4, 5, and/or 10 shown in Table 1. In some instances, such peptides include CDR3 of the $V_H$ and $V_L$ of antibody ID 2, 3, 4, 5, and/or 10 and CDR1 and/or CDR2 of the $V_H$ and/or $V_L$ of antibody ID 2, 3, 4, 5, and/or 10 shown in Table 1. In some instances, such peptides include CDR1, CDR2, and CDR3 of the $V_H$ and/or $V_L$ of antibody ID 2, 3, 4, 5, and/or 10. In some instances, such peptides include CDR1 CDR2, and CDR3 of the $V_H$ and/or $V_L$ of antibody ID 2, 3, 4, 5, and/or 10 and at least one of FR1 FR2 FR3, and/or FR4 of the $V_H$ and/or $V_L$ of antibody ID 2, 3, 4, 5, and/or 10 5, shown in Table 1. In some instances, such peptides include one of SEQ ID NO:20, 38, 56, 74, or 222 and/or one of SEQ ID NO:29, 47, 65, 83 or 224. In some instances, peptides include one of SEQ ID NO:20, 38, 56, 74, or 222 and one of SEQ ID NO:29, 47, 65, 83 or 224. In each instance, the peptide can bind (e.g., bind specifically and/or bind immunospecifically) to angiopoietin-2 (e.g., human angiopoietin-2 (e.g, UniGene Hs.583870)).

In some instances, therapeutic compositions can include peptides that include at least one CDR of the $V_H$ and/or $V_L$ of antibody ID 2 shown in Table 1, wherein the peptide binds (e.g., binds specifically and/or binds immunospecifically) to angiopoietin-2 (e.g., human angiopoietin-2). In some instances, such peptides include CDR3 of the $V_H$ and/or $V_L$ of antibody ID 2 shown in Table 1. In some instances, such peptides include CDR3 of the $V_H$ and $V_L$ of antibody ID 2 and CDR1 and/or CDR2 of the $V_H$ and/or $V_L$ of antibody ID 2 shown in Table 1. In some instances, such peptides include CDR1, CDR2, and CDR3 of the $V_H$ and/or $V_L$ of antibody ID 2. In some instances, such peptides include CDR1 CDR2, and CDR3 of the $V_H$ and/or $V_L$ of antibody ID 2 and at least one of FR1 FR2 FR3, and/or FR4 of the $V_H$ and/or $V_L$ of antibody ID 2, shown in Table 1. In some instances, such peptides include SEQ ID NO:20 and/or SEQ ID NO:29. In each instance, the peptide can bind (e.g., bind specifically and/or bind immunospecifically) to angiopoietin-2 (e.g., human angiopoietin-2). In some instances, the affinity of binding between the peptides and angiopoietin-2 can be between about 0.1 nM to 1 μM, for example, about 10 nM.

In some instances, therapeutic compositions can include peptides that include at least one CDR of the $V_H$ and/or $V_L$ of antibody ID 3 shown in Table 1, wherein the peptide binds (e.g., binds specifically and/or binds immunospecifically) to angiopoietin-2 (e.g., human angiopoietin-2). In some instances, such peptides include CDR3 of the $V_H$ and/or $V_L$ of antibody ID 3 shown in Table 1. In some instances, such peptides include CDR3 of the $V_H$ and $V_L$ of antibody ID 3 and CDR1 and/or CDR2 of the $V_H$ and/or $V_L$ of antibody ID 3 shown in Table 1. In some instances, such peptides include CDR1, CDR2, and CDR3 of the $V_{H1}$ and/or $V_L$ of antibody ID 3. In some instances, such peptides include CDR1 CDR2, and CDR3 of the $V_H$ and/or $V_L$ of antibody ID 3 and at least one of FR1 FR2 FR3, and/or FR4 of the $V_H$ and/or $V_L$ of antibody ID 3, shown in Table 1. In some instances, such peptides include SEQ ID NO:38 and/or SEQ ID NO:47. In each instance, the peptide can bind (e.g., bind specifically and/or bind immunospecifically) to angiopoietin-2 (e.g., human angiopoietin-2). In some instances, the affinity of binding between the peptides and angiopoietin-2 can be between about 0.1 nM to 1 μM, for example, about 10 nM.

In some instances, therapeutic compositions can include peptides that include at least one CDR of the $V_H$ and/or $V_L$ of antibody ID 4 shown in Table 1, wherein the peptide binds (e.g., binds specifically and/or binds immunospecifically) to angiopoietin-2 (e.g., human angiopoietin-2). In some instances, such peptides include CDR3 of the $V_H$ and/or $V_L$ of antibody ID 4 shown in Table 1. In some instances, such peptides include CDR3 of the $V_H$ and $V_L$ of antibody ID 4 and CDR1 and/or CDR2 of the $V_H$ and/or $V_L$ of antibody ID 4 shown in Table 1. In some instances, such peptides include CDR1, CDR2, and CDR3 of the $V_H$ and/or $V_L$ of antibody ID 4. In some instances, such peptides include CDR1 CDR2, and CDR3 of the $V_H$ and/or $V_L$ of antibody ID 4 and at least one of FR1 FR2 FR3, and/or FR4 of the $V_H$ and/or $V_L$ of antibody ID 4, shown in Table 1. In some instances, such peptides include SEQ ID NO:56 and/or SEQ ID NO:65. In each instance, the peptide can bind (e.g., bind specifically and/or bind immunospecifically) to angiopoietin-2 (e.g., human angiopoietin-2). In some instances, the affinity of binding between the peptide and angiopoietin-2 can be between X-Y, for example, X-Y, X-Y. In some instances, the affinity of binding between the peptides and angiopoietin-2 can be between about 0.1 nM to 1 μM, for example, about 10 nM.

In some instances, therapeutic compositions can include peptides that include at least one CDR of the $V_H$ and/or $V_L$ of antibody ID 5 shown in Table 1, wherein the peptide binds (e.g., binds specifically and/or binds immunospecifically) to angiopoietin-2 (e.g., human angiopoietin-2). In some instances, such peptides include CDR3 of the $V_H$ and/or $V_L$ of antibody ID 5 shown in Table 1. In some instances, such peptides include CDR3 of the $V_H$ and $V_L$ of antibody ID 5 and CDR1 and/or CDR2 of the $V_H$ and/or $V_L$ of antibody ID 5 shown in Table 1. In some instances, such peptides include CDR1, CDR2, and CDR3 of the $V_H$ and/or $V_L$ of antibody ID 5. In some instances, such peptides include CDR1 CDR2, and CDR3 of the $V_H$ and/or $V_L$ of antibody ID 5 and at least one of FR1 FR2 FR3, and/or FR4 of the $V_H$ and/or $V_L$ of antibody ID 5, shown in Table 1. In some instances, such peptides include SEQ ID NO:74 and/or SEQ ID NO:83. In each instance, the peptide can bind (e.g., bind specifically and/or bind immunospecifically) to angiopoietin-2 (e.g., human angiopoietin-2). In some instances, the affinity of binding between the peptides and angiopoietin-2 can be between about 0.1 nM to 1 μM, for example, about 10 nM.

In some instances, therapeutic compositions can include peptides that include at least one CDR of the $V_H$ and/or $V_L$ of antibody ID 10 shown in Table 1, wherein the peptide binds (e.g., binds specifically and/or binds immunospecifically) to angiopoietin-2 (e.g., human angiopoietin-2). In some instances, such peptides include CDR3 of the $V_H$ and/or $V_L$ of antibody ID 10 shown in Table 1. In some instances, such peptides include CDR3 of the $V_H$ and $V_L$ of antibody ID 10 and CDR1 and/or CDR2 of the $V_H$ and/or $V_L$ of antibody ID 10 shown in Table 1. In some instances, such peptides include CDR1, CDR2, and CDR3 of the $V_H$ and/or $V_L$ of antibody ID 10. In some instances, such peptides include CDR1 CDR2, and CDR3 of the $V_H$ and/or $V_L$ of antibody ID 10 and at least one of FR1 FR2 FR3, and/or FR4 of the $V_H$ and/or $V_L$ of antibody ID 10, shown in Table 1. In some instances, such peptides include SEQ ID NO:222 and/or SEQ ID NO:224. In each instance, the peptide can bind (e.g., bind specifically and/or bind immunospecifically) to angiopoietin-2 (e.g., human angiopoietin-2). In some instances, the affinity of binding between the peptides and angiopoietin-2 can be between about 0.1 nM to 1 μM, for example, about 10 nM.

In some instances, peptides that bind to angiopoietin-2 can also bind to angiopoietin-1 (e.g., Unigene Hs.369675) and/or angiopoietin-4 (e.g., Unigene Hs.278973). For example, in some instances, peptides that bind to angiopoietin-2 can also bind specifically and/or immunospecifically relative to other antigens (other than angiopoietin-1) to angiopoictin-1. In some instances, peptides that bind to angiopoietin-2 can also bind specifically and/or immunospecifically relative to other antigens (other than angiopoietin-4) to angiopoietin-4.

In some instances, therapeutic compositions can include peptides that include: SEQ ID NO: 2 and/or SEQ ID NO: 11; SEQ ID NO: 149 and/or SEQ ID NO:151; SEQ ID NO: 168 and/or SEQ ID NO:170; SEQ ID NO: 186 and/or SEQ ID NO:188; SEQ ID NO: 204 and/or SEQ ID NO:206; SEQ ID NO:20 and/or SEQ ID NO:29; SEQ ID NO:38 and/or SEQ ID NO:47; SEQ ID NO:56 and/or SEQ ID NO:65; SEQ ID NO:74 and/or SEQ ID NO:83; and SEQ ID NO: 222 and/or SEQ ID NO:224.

TABLE 1

| ID Target | $V_H$ / $V_L$ | FR1* | CDR1** | FR2* | CDR2** | FR3* | CDR3** | FR4* | A.A.# | Nuc. Acid## |
|---|---|---|---|---|---|---|---|---|---|---|
| 1 Human MICA | $V_H$ | QVQLQQW GAGLLKP SETLALT CAVS (SEQ ID NO: 3) | GGSFTDH Y (SEQ ID NO: 4) | WSWIRQA PGKGLEW IGE (SEQ ID NO: 5) | INHSGVT (SEQ ID NO: 6) | NYNPSLK SRLTISV DTSKSQF SLRLTSV TAADTAL YYC (SEQ ID NO: 7) | AKTGLYY DDVWGTF RPRGGFD S (SEQ ID NO: 8) | WGQGTLV TVSS (SEQ ID NO: 9) | SEQ ID NO: 2 (see FIG. 2) | SEQ ID NO: 1 (see FIG. 1) |
| | $V_L$ | DIVMTQS PDSLAVS LGERATI NCKSS (SEQ ID NO: 12) | QSILYSS DNKNY (SEQ ID NO: 13) | LAWYQHK PGQPPKL LFY (SEQ ID NO: 14) | WAS (SEQ. ID NO: 15) | IRESGVP DRESGGG SGTDFTL TISSLQA EDVAVYY C (SEQ ID NO: 16) | QQYYSPP CS (SEQ ID NO: 17) | FGQGTKL EIQ (SEQ ID NO: 18) | SEQ ID NO: 11 (see FIG. 4) | SEQ ID NO: 10 (see FIG. 3) |
| 6 Human MICA | $V_H$ | QVQLQES GPGLVEP SGTLSLT CTVS (SEQ ID NO: 152) | GGSISRS NW (SEQ ID NO: 153) | WSVVVRQ PPGEGLE WIGE (SEQ ID NO: 154) | IHHIGRS (SEQ ID NO: 156) | SYNPSLK SRVTMSV DKSQNQF SLRLTSV TAADTAV YY (SEQ ID NO: 157) | CAKNGYY AMDVW (SEQ ID NO: 158) | GQGTIVI VSS (SEQ ID NO: 155) | SEQ ID NO: 149 (see FIG. 28) | SEQ ID NO: 148 (see FIG. 29) |
| | $V_L$ | EIVLTQS PGTLSLS PGERATL SCRAS (SEQ ID NO: 159) | QSVSSDF (SEQ ID NO: 160) | LAWYQQK PGQAPRL LIY (SEQ ID NO: 161) | ATS (SEQ ID NO: 162) | FRATGIS DRIFSGS GSGTDFS LTINRLE PEDFAVY Y (SEQ ID NO: 163) | CQHYRSS PPWYTF (SEQ ID NO: 164) | AQGTKL DMRRTV AAPSV (SEQ ID NO: 165) | SEQ ID NO: 151 (see FIG. 31) | SEQ ID NO: 150 (see FIG. 30) |
| 7 Human MICA | $V_H$ | QVQLQES GPGLVKP SGTLSLT CAVS (SEQ ID NO: 171) | GASITNG AW (SEQ ID NO: 172) | WSWVRQ PPGKGLE WIGE (SEQ ID NO: 173) | IYLNGNI (SEQ ID NO: 174) | NSNPSLK SRVIISVD KSKNHFS LTLNSVT AADTAV YY (SEQ ID NO: 166) | CAKNAAY NLEFW (SEQ. ID NO: 176) | GQGALVT VSS (SEQ ID NO: 177) | SEQ ID NO: 168 (see FIG. 33) | SEQ ID NO: 167 (see FIG. 32) |
| | $V_L$ | EIVLTQS PGTLSLS PGERATL SCRAS (SEQ ID NO: 178) | QTVSSPY (SEQ ID NO: 179) | VAWYQQ KRGQAP RLLIY (SEQ ID NO: 180) | GAS (SEQ ID NO: 181) | TRATGIP DRFSGSG SGTDFTL TISRLEP EDFAVYY (SEQ ID NO: 182) | CQQYDRS YYYTF (SEQ ID NO: 183) | GQGTKLE IK (SEQ ID NO: 184) | SEQ ID NO: 170 (see FIG. 35) | SEQ ID NO: 169 (see FIG. 34) |
| 8 Human MICA | $V_H$ | QVQLQES GPGLVKP SENLSLT CTVS (SEQ ID NO: 189) | DASMSDY H (SEQ ID NO: 190) | WSWIRQA AGKGLEW IGR (SEQ ID NO: 191) | MYSTGSP (SEQ ID NO: 192) | YYKPSLK GRVTMSI DTSKNQF SLKLASV TAADTAI YY (SEQ ID NO: 193) | CASGQHI GGWVPPD FW (SEQ ID NO: 194) | GQGTLVT VSS (SEQ ID NO: 195) | SEQ ID NO: 186 (see FIG. 37) | SEQ ID NO: 185 (see FIG. 36) |
| | $V_L$ | DIVMTQT PLSSPVT LGQPASI SCRSS (SEQ ID NO: 196) | EGLVYSD GDTY (SEQ ID NO: 197) | LSWFHQR PGQPPRL LIY (SEQ ID NO: 198) | KIS (SEQ ID NO: 199) | NRFSGVP DRIFSGS GAGTDFT LKISRVE AEDVGVY Y (SEQ ID NO: 200) | CMQATHF PWIT (SEQ ID NO: 201) | GQGTKVE VKR (SEQ ID NO: 202) | SEQ ID NO: 188 (see FIG. 39) | SEQ ID NO: 187 (see FIG. 38) |
| 9 Human MICA | $V_H$ | EVQLLES GGGLVQP | GETTSSY G | LTWIRQA PGKGLEW | ISGSGNN T | YYADSVK GRFTISR | CLGVGQ (SEQ ID | GHGIPVI VSS | SEQ ID NO: 204 | SEQ ID NO: 203 |

TABLE 1-continued

| ID | Target | V_H / V_L | FR1* | CDR1** | FR2* | CDR2** | FR3* | CDR3** | FR4* | A.A.# | Nuc. Acid## |
|---|---|---|---|---|---|---|---|---|---|---|---|
| | | | GGSLRLS CAAS (SEQ ID NO: 207) | VSS (SEQ ID NO: 208) | (SEQ ID NO: 209) | (SEQ ID NO: 210) | DKVKKTL YLQMDSL TVGDTAV YY (SEQ ID NO: 211) | NO: 212) | (SEQ ID NO: 213) | (see FIG. 41) | (see FIG. 40) |
| | | V_L | DIVMTQT PLSSPVT LGQPASI SCRSS (SEQ ID NO: 214) | QSLVHRD GNTY (SEQ ID NO: 215) | LSWFLQR PGQAPRL LIY (SEQ ID NO: 216) | RIS (SEQ ID NO: 217) | NRFSGVP DRFSGSG AGTDFTL KISRVEA EDVGVYY (SEQ ID NO: 218) | CMQATQI PNTF (SEQ ID NO: 219) | GQGTKLE IK (SEQ ID NO: 220) | SEQ ID NO: 206 (see FIG. 43) | SEQ ID NO: 205 (see FIG. 42) |
| 2 | Angio-poietin-2 | V_H | EVQLVES GGGLVQP GGSLRLS CAAS (SEQ ID NO: 21) | GFTFSSY A (SEQ ID NO: 22) | MSWVRQA PGKGLEW VSG (SEQ ID NO: 23) | IYWSGGS T (SEQ ID NO: 24) | YYADSVK GRFTISR DISKNTL YLQMNSL RADDTAV YYC (SEQ ID NO: 25) | ARGDYYG SGAHFDY (SEQ ID NO: 26) | WGQGTLV TVSS (SEQ ID NO: 27) | SEQ ID NO: 20 (see FIG. 6) | SEQ ID NO: 19 (see FIG. 5) |
| | | V_L | DIVMTQT PLSSPVT LGQPASI SCRSS (SEQ ID NO: 30) | QSLVHSD GNTY (SEQ ID NO: 31) | LSVVLQQ RPGQPPR LLIY (SEQ ID NO: 32) | QIS (SEQ ID NO: 33) | NRFSGVP DRFSGSG AGTDFTL KISRVEA EDVGVYY C (SEQ ID NO: 34) | MQGTQFP RT (SEQ ID NO: 35) | FGQGTKV EIK (SEQ ID NO: 36) | SEQ ID NO: 29 (see FIG. 8) | SEQ ID NO: 28 (see FIG. 7) |
| 3 | Angio-poietin-2 | V_H | EVQLVES GGGLVQP GGSLRLS GAAS (SEQ ID NO: 39) | GETESNN W (SEQ ID NO: 40) | MHWVRQA PGKGLEW ISE (SEQ ID NO: 41) | IRSDGNF T (SEQ ID NO: 42) | RYADSM KGRFTI SRDNAK STLYLQ MNSLRV EDTGLY YC (SEQ ID NO: 43) | ARDYPYS IDY (SEQ ID NO: 44) | WGQGTLV TVSS (SEQ ID NO: 45) | SEQ ID NO: 38 (see FIG. 10) | SEQ ID NO: 37 (see FIG. 9) |
| | | V_L | DIVMTQT PLSSPVT LGQPASI SCTSS (SEQ ID NO: 48) | QSLVHSN GNTY (SEQ ID NO: 49) | LSWLQQR PGQPPRL LIY (SEQ ID NO: 50) | EIS (SEQ ID NO: 51) | KRVSGVP DRESGSG AGTDFTL KISRVEA EDVGVYY C (SEQ ID NO: 52) | MQGKQL RT (SEQ ID NO: 53) | FGQGTKL EIK (SEQ ID NO: 54) | SEQ ID NO: 47 (see FIG. 12) | SEQ ID NO: 46 (see FIG. 11) |
| 4 | Angio-poietin-2 | V_H | EVQLVES GGGLVQP GGSVRLS GAAS (SEQ ID NO: 57) | GFILSNF A (SEQ ID NO: 58) | MSWVRQA PGKGLDW VSG (SEQ ID NO: 59) | NFGGREN T (SEQ ID NO: 60) | YYADSVK GRFTISR DSSKSTL YLQMNNL RAEDTAV YYC (SEQ ID NO: 61) | ARGDYHG SGAHFDY (SEQ ID NO: 62) | WGQGILV TVSS (SEQ ID NO: 63) | SEQ ID NO: 56 (see FIG. 14) | SEQ ID NO: 55 (see FIG. 13) |
| | | V_L | DIVMTQS PLSSPVI LGQPASI SCRSS (SEQ ID NO: 66) | QSLLHSD GNTY (SEQ ID NO: 67) | LSWLHQR PGQPPRL LIY (SEQ ID NO: 68) | QIS (SEQ ID NO: 69) | NRFSGVP DRFSGSG TGTDFTL KISRVEA EDAGIYY C (SEQ ID NO: 70) | MQGTEFP RT (SEQ ID NO: 71) | FGQGTKV EIK (SEQ ID NO: 72) | SEQ ID NO: 65 (see FIG. 16) | SEQ ID NO: 64 (see FIG. 15) |
| 5 | Angio-poietin-2 | V_H | EVQLVES GGGLIQP GGSLRLS CATS (SEQ ID NO: 75) | GFTFRTS S (SEQ ID NO: 76) | MSWVRRA PGKGLEW VSA (SEQ ID NO: 77) | IGAESHD T (SEQ ID NO: 78) | HYTDSAE GRFTISK DYSKNTV YLQMNGL RVDDTAI YYC (SEQ ID NO: 79) | AHHYYYG SRQKPKD WGDAFDM (SEQ ID NO: 80) | WGQGTMV SVSS (SEQ ID NO: 81) | SEQ ID NO: 74 (see FIG. 18) | SEQ ID NO: 73 (see FIG. 17) |
| | | V_L | DIQMTQS PSSVSAS VGDRVTI (SEQ ID NO: 85) | QDISTW (SEQ ID NO: 85) | LTWYQQR AGKAPNL LIY (SEQ ID NO: 87) | GAS | TLEDGVP SRFSGSG SGTDFTL (SEQ ID | QQSHSFP YT (SEQ ID | FGQGTQL GIS | SEQ ID NO: 83 (see | SEQ ID NO: 82 (see |

TABLE 1-continued

| ID Target | V$_H$ / V$_L$ | FR1* | CDR1** | FR2* | CDR2** | FR3* | CDR3** | FR4* | A.A.# | Nuc. Acid## |
|---|---|---|---|---|---|---|---|---|---|---|
| | | TCRAS (SEQ ID NO: 84) | | (SEQ ID NO: 86) | | TIDSLQP DDFATYY C (SEQ ID NO: 88) | NO: 89) | NO: 90) | FIG. 20) | FIG. 19) |
| 10 Angio-poietin-2 | V$_H$ | EVQLVES GGGLIQP GGSLRLS CAAS (SEQ ID NO: 225) | GFLISSY F (SEQ ID NO: 226) | MSWVRQA PGKGPEW VSV (SEQ ID NO: 227) | IYSDGST (SEQ ID NO: 228) | YYVDSVK GRFTIST DNSKNTL YLQMNSL RAEDTAR YY (SEQ ID NO: 229) | CATRHLN YDGDHW (SEQ ID NO: 230) | GQGTLVT VSSASTK (SEQ ID NO: 175) | SEQ ID NO: 222 (see FIG. 45) | SEQ ID NO: 221 (see FIG. 44) |
| | V$_L$ | DVVMTQS PLSLPVT LGQPASI SCRSS (SEQ ID NO: 231) | QSLVHSD GNTY (SEQ ID NO: 232) | LNWFHQR PGQSPRR LIY (SEQ ID NO: 233) | KVS (SEQ ID NO: 234) | KRDSGVP DRFSGSG SGSDFTL KISRVEA EDVGIYY (SEQ ID NO: 235) | CMQGTHW PTF (SEQ ID NO: 236) | GQGTKVE IKRTVAA (SEQ ID NO: 237) | SEQ ID NO: 224 (see FIG. 47) | SEQ ID NO: 223 (see FIG. 46) |

*Sequences include sequences or variants with (e.g., with at least) 80%, 85%, 90%, 95%, 96%, 97%, 98, 99%, and/or 100% sequence identity to the sequences shown.
**Sequences can include one, two, three, four, five, less than five, or less than ten conservative amino acid modifications.
Sequences include sequences or variants with (e.g., with at least) 80%, 85%, 90%, 95%, 96%, 97%, 98, 99%, and/or 100% sequence identity to the sequences shown, e.g., within regions corresponding to FR1, FR2, FR3, and/or FR4, and/or one, two, three, four, five, less than 5, or less than ten conservative amino acid modifications within regions corresponding to CDRs 1, 2, and/or 3.
Sequences include sequences or variants with (e.g., with at least) 80%, 85%, 90%, 95%, 96%, 97%, 98, 99%, and/or 100% sequence identity to the sequences shown, wherein the sequences encode the corresponding AA.
A.A.# shows the V$_H$ or V$_L$ amino acid sequence.
Nuc. Acid## shows the V$_H$ or V$_L$ nucleic acid sequence.
While CDR and FR regions are shown above, such regions can also be defined according to Kabat (Sequences of Proteins of Immunological Interest(National Institutes of Health, Bethesda, Md., 1987 and 1991)). Amino acid numbering of antibodies or antigen binding fragments is also according to that of Kabat.

In some instances, therapeutic compositions can include peptides, including for example, antibodies, including full length and/or intact antibodies, or antibody fragments. An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody" encompasses not only intact polyclonal or monoclonal antibodies, but also any antigen binding fragment (i.e., "antigen-binding portion") or single chain thereof, fusion proteins comprising an antibody, and any other modified configuration of the immunoglobulin molecule that comprises an antigen recognition site including. An antibody includes an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant regions that correspond to the different classes of immunoglobulins are called alpha, delta, epsilon, gamma, and mu, respectively. The subunit structures and three-dimensional configurations of different classes of immunoglobulins are well known. Exemplary antibodies and antibody fragments include, but are not limited to, monoclonal antibodies (including full-length monoclonal antibodies), polyclonal antibodies, multispecific antibodies formed from at least two different epitope binding fragments (e.g., bispecific antibodies), camelised antibodies, chimeric antibodies, single-chain Fvs (scFv), single-chain antibodies, single domain antibodies, domain antibodies, Fab fragments, F(ab')2 fragments, antibody fragments that exhibit the desired biological activity (e.g. the antigen binding portion), disulfide-linked Fvs (dsFv), and anti-idiotypic (anti-Id) antibodies (including, e.g., anti-Id antibodies to antibodies of the invention), intrabodies, and epitope-binding fragments of any of the above. Antibodies or antibody fragments can be human or humanized.

Fragments of antibodies are suitable for use in the methods provided so long as they retain the desired affinity and specificity of the full-length antibody. Thus, a fragment of an anti-MICA antibody or the anti-Angiopoietin antibody will retain an ability to bind to MICA or angiopoietin, respectively, in the Fv portion and the ability to bind the Fc receptor on dendritic cells in the FC portion. Such fragments are characterized by properties similar to the corresponding full-length anti-MICA antibody or the anti-Angiopoietin antibody, that is, the fragments will specifically bind a human MICA antigen or the angiopoietin antigen, respectively, expressed on the surface of a human cell or the corresponding sMICA antigen that has been shed into the media.

An Fv fragment is an antibody fragment which contains a complete antigen recognition and binding site. This region consists of a dimer of one heavy and one light chain variable domain in tight association, which can be covalent in nature, for example in scFv. It is in this configuration that the three CDRs of each variable domain interact to define an antigen binding site on the surface of the VH-VL dimer. Collectively, the six CDRs or a subset thereof confer antigen binding specificity to the antibody. However, even a single variable domain (or half of an Fv comprising only three CDRs specific for an antigen) can have the ability to recognize and bind antigen, although usually at a lower affinity than the entire binding site.

Single-chain Fv or (scFv) antibody fragments comprise the $V_H$ and $V_L$ domains of antibody, wherein these domains are present in a single polypeptide chain. Generally the Fv polypeptide further comprises a polypeptide linker between the $V_H$ and $V_L$ domains, which enables the scFv to form the desired structure for antigen binding.

The Fab fragment contains a variable and constant domain of the light chain and a variable domain and the first constant domain (CH1) of the heavy chain. F(ab')2 antibody fragments comprise a pair of Fab fragments which are generally covalently linked near their carboxy termini by hinge cysteines between them. Other chemical couplings of antibody fragments are also known in the art.

Diabodies are small antibody fragments with two antigen-binding sites, which fragments comprise a $V_H$ connected to a $V_L$ in the same polypeptide chain ($V_H$ and $V_L$). By using a linker that is too short to allow pairing between the two domains on the same chain, the domains are forced to pair with the complementary domains of another chain and create two antigen-binding sites.

Linear antibodies comprise a pair of tandem Fd segments ($V_H$—CH1-$V_H$—CH1) which, together with complementary light chain polypeptides, form a pair of antigen binding regions. Linear antibodies can be bispecific or monospecific.

Antibodies and antibody fragments of the present disclosure can be modified in the Fc region to provide desired effector functions or serum half-life. In some instances, the Fc region can be conjugated to PEG or albumin to increase the serum half-life, or some other conjugation that results in the desired effect. Alternatively, where it is desirable to eliminate or reduce effector function, so as to minimize side effects or therapeutic complications, certain other Fc regions may be used.

Human and humanized antibodies include antibodies having variable and constant regions derived from (or having the same amino acid sequence as those derived from) human germline immunoglobulin sequences. Human antibodies may include amino acid residues not encoded by human germline immunoglobulin sequences (e.g., mutations introduced by random or site-specific mutagenesis in vitro or by somatic mutation in vivo), for example in the CDRs and in particular CDR3.

A "CDR" of a variable domain are amino acid residues within the hypervariable region that are identified in accordance with the definitions of the Kabat, Chothia, the cumulation of both Kabat and Chothia, AbM, contact, and/or conformational definitions or any method of CDR determination well known in the art. Antibody CDRs may be identified as the hypervariable regions originally defined by Kabat et al. See, e.g., Kabat et al., 1992, Sequences of Proteins of Immunological Interest, 5th ed., Public Health Service, NIH, Washington D.C. The positions of the CDRs may also be identified as the structural loop structures originally described by Chothia and others. See, e.g., Chothia et al., 1989, Nature 342:877-883. Other approaches to CDR identification include the "AbM definition," which is a compromise between Kabat and Chothia and is derived using Oxford Molecular's AbM antibody modeling software (now Accelrys®), or the "contact definition" of CDRs based on observed antigen contacts, set forth in MacCallum et al., 1996, J. Mol. Biol., 262:732-745. In another approach, referred to herein as the "conformational definition" of CDRs, the positions of the CDRs may be identified as the residues that make enthalpic contributions to antigen binding. See, e.g., Makabe et al., 2008, Journal of Biological Chemistry, 283:1156-1166. Still other CDR boundary definitions may not strictly follow one of the above approaches, but will nonetheless overlap with at least a portion of the Kabat CDRs, although they may be shortened or lengthened in light of prediction or experimental findings that particular residues or groups of residues or even entire CDRs do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs may be defined in accordance with any of Kabat, Chothia, extended, AbM, contact, and/or conformational definitions.

In some instances, amino acid sequences of the peptides disclosed herein can be modified and varied to create peptide variants (e.g., peptides with a defined sequence homology to the peptides disclosed herein), for example, so long as the antigen binding property of the peptide variant is maintained or improved relative to the unmodified peptide (antigen binding properties of any modified peptide can be assessed using the in vitro and/or in vivo assays described herein and/or techniques known in the art).

While peptide variants are generally observed and discussed at the amino acid level, the actual modifications are typically introduced or performed at the nucleic acid level. For example, variants with 80%, 85%, 90%, 95%, 96%, 97%, 98, or 99% amino acid sequence identity to the peptides shown in Table 1 can be generated by modifying the nucleic acids encoding SEQ ID NOs:1, 10, 19, 28, 37, 46, 55, 64, 73, and/or 82 or portions/fragments thereof, using techniques (e.g., cloning techniques) known in the art and/or that are disclosed herein.

Amino acid sequence modifications typically fall into one or more of three classes: substitutional, insertional, or deletional modifications. Insertions include amino and/or terminal fusions as well as intra-sequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. Typically, no more than about from 2 to 6 residues are deleted at any one site within the protein molecule. Amino acid substitutions are typically of single residues, but can occur at a number of different locations at once; insertions usually will be on the order of about from 1 to 10 amino acid residues; and deletions will range about from 1 to 30 residues. Deletions or insertions can be made in adjacent pairs, i.e., a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional modifications are those in which at least one residue has been removed and a different residue inserted in its place. In some instances, substitutions can be conservative amino acid substitutions. In some instances, peptides herein can include one or more conservative amino acid substitutions relative to a peptide shown in Table 1. For example, variants can include 1, 2, 3, 4, 5, 6, 7, 8, 9, 10, 11, 12, 13, 14, 15, 16, 17, 18, 19, 20, 20-30, 30-40, or 40-50 conservative amino acid substitutions relative to a peptide shown in Table 1. Alternatively, variants can include 50 or fewer, 40 or fewer, 30 or fewer, 20 or fewer, 10 or fewer, 9 or fewer, 8 or fewer, 7 or fewer, 6 or fewer, 5 or fewer, 4 or fewer, 3 or fewer, or 2 or fewer conservative amino acid substitutions relative to a peptide shown in Table 1. Such substitutions generally are made in accordance with the following Table 2 and are referred to as conservative substitutions. Methods for predicting tolerance to protein modification are known in the art (see, e.g., Guo et al., Proc. Natl. Acad. Sci., USA, 101(25):9205-9210 (2004)).

TABLE 2

Conservative Amino Acid Substitutions

| Amino Acid | Substitutions (others are known in the art) |
|---|---|
| Ala | Ser, Gly, Cys |
| Arg | Lys, Gln, His |
| Asn | Gln, His, Glu, Asp |
| Asp | Glu, Asn, Gln |
| Cys | Ser, Met, Thr |
| Gln | Asn, Lys, Glu, Asp, Arg |
| Glu | Asp, Asn, Gln |
| Gly | Pro, Ala, Ser |
| His | Asn, Gln, Lys |
| Ile | Leu, Val, Met, Ala |
| Leu | Ile, Val, Met, Ala |
| Lys | Arg, Gln, His |
| Met | Leu, Ile, Val, Ala, Phe |
| Phe | Met, Leu, Tyr, Trp, His |
| Ser | Thr, Cys, Ala |
| Thr | Ser, Val, Ala |
| Trp | Tyr, Phe |
| Tyr | Trp, Phe, His |
| Val | Ile, Leu, Met, Ala, Thr |

In some instances, substitutions are not conservative. For example, an amino acid in a peptide shown in Table 1 can be replaced with an amino acid that can alter some property or aspect of the peptide. In some instances, non-conservative amino acid substitutions can be made, e.g., to change the structure of a peptide, to change the binding properties of a peptide (e.g., to increase or decrease the affinity of binding of the peptide to an antigen and/or to alter increase or decrease the binding specificity of the peptide to the antigen).

In some instances, peptides and/or peptide variants can include or can be fragments of the peptides shown in Table 1. Such fragments can include, for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 37, 38, 39, 40, 41, 42, 43, 44, 45, 46, 47, 48, 49, 50, 50-100, 101-150, fewer amino acids than the CDRs, FRs, and/or AAs shown in Table 1, e.g., so long as the fragments retain at least at portion of the binding properties of the full-length peptide (e.g., at least 50%, 60%, 70%, 80%, 90%, or 100% of the binding properties of the full-length peptide). Truncations can be made at the amino-terminus, the carboxy-terminus, and/or within the peptides herein.

In some instances, the interacting face of a peptide variant can be the same (e.g., substantially the same) as an unmodified peptide, e.g., to alter (e.g., increase or decrease), preserve, or maintain the binding properties of the peptide variant relative to the unmodified peptide. Methods for identifying the interacting face of a peptide are known in the art (Gong et al., BMC: Bioinformatics, 6:1471-2105 (2007); Andrade and Wei et al., Pure and Appl. Chem., 64(11):1777-1781 (1992); Choi et al., Proteins: Structure, Function, and Bioinformatics, 77(1):14-25 (2009); Park et al., BMC: and Bioinformatics, 10: 1471-2105 (2009).

Those of skill in the art readily understand how to determine the identity of two polypeptides (e.g., an unmodified peptide and a peptide variant). For example, identity can be calculated after aligning the two sequences so that the identity is at its highest level. Another way of calculating identity can be performed by published algorithms.

Optimal alignment of sequences for comparison may be conducted by the local identity algorithm of Smith and Waterman, Adv. Appl. Math, 2:482 (1981), by the identity alignment algorithm of Needleman and Wunsch, J. Mol. Biol. 48:443 (1970), by the search for similarity method of Pearson and Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of identity can be obtained for nucleic acids by, for example, the algorithms disclosed in Zuker, Science 244:48-52 (1989); Jaeger et al., Proc. Natl. Acad. Sci. USA 86:7706-10 (1989); Jaeger et al., Methods Enzymol. 183:281-306 (1989), which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity and to be disclosed herein.

In some instances, as described in more detail under the methods section below, therapeutic compositions disclosed herein can be produced using genetic material (e.g., DNA and/or mRNA) isolated and/or purified from immune cells (e.g., B cells, including memory B cells) obtained using the methods disclosed herein. Once such genetic material has been obtained, methods for using it to produce the therapeutic compositions disclosed herein are known in the art and/or are summarized below.

In some instances, peptides can include a detectable label. As used herein, a "label" refers to a moiety that has at least one element, isotope, or functional group incorporated into the moiety which enables detection of the peptide to which the label is attached. Labels can be directly attached (ie, via a bond) or can be attached by a linker (e.g., such as, for example, a cyclic or acyclic, branched or unbranched, substituted or unsubstituted alkylene; cyclic or acyclic, branched or unbranched, substituted or unsubstituted alkenylene; cyclic or acyclic, branched or unbranched, substituted or unsubstituted alkynylene; cyclic or acyclic, branched or unbranched, substituted or unsubstituted heteroalkylene; cyclic or acyclic, branched or unbranched, substituted or unsubstituted heteroalkenylene; cyclic or acyclic, branched or unbranched, substituted or unsubstituted heteroalkynylene; substituted or unsubstituted arylene; substituted or unsubstituted heteroarylene; or substituted or unsubstituted acylene, or any combination thereof, which can make up a linker). Labels can be attached to a peptide at any position that does not interfere with the biological activity or characteristic of the inventive polypeptide that is being detected.

Labels can include: labels that contain isotopic moieties, which may be radioactive or heavy isotopes, including, but not limited to, $^2$H, $^3$H, $^{13}$C, $^{14}$C, $^{15}$N, $^{31}$P, $^{32}$P, $^{35}$S, $^{67}$Ga, $^{99m}$Tc (Tc-99m), $^{111}$In, $^{123}$I, $^{125}$I, $^{169}$Yb, and $^{186}$Re; labels that include immune or immunoreactive moieties, which may be antibodies or antigens, which may be bound to enzymes (e.g., such as horseradish peroxidase); labels that are colored, luminescent, phosphorescent, or include fluorescent moieties (e.g., such as the fluorescent label FITC); labels that have one or more photoaffinity moieties; labels that have ligand moieties with one or more known binding partners (such as biotin-streptavidin, FK506-FKBP, etc.).

In some instances, labels can include one or more photoaffinity moieties for the direct elucidation of intermolecular interactions in biological systems. A variety of known photophores can be employed, most relying on photoconversion of diazo compounds, azides, or diazirines to nitrenes or carbenes (see, e.g., Bayley, H., Photogenerated Reagents in Biochemistry and Molecular Biology (1983), Elsevier, Amsterdam, the entire contents of which are incorporated herein by reference). In certain embodiments of the invention, the photoaffinity labels employed are o-, m- and p-azidobenzoyls, substituted with one or more halogen moieties, including, but not limited to 4-azido-2,3,5,6-tetrafluorobenzoic acid.

Labels can also be or can serve as imaging agents. Exemplary imaging agents include, but are not limited to, those used in positron emissions tomography (PET), computer assisted tomography (CAT), single photon emission computerized tomography, x-ray, fluoroscopy, and magnetic resonance imaging (MRI); anti-emetics; and contrast agents. Exemplary diagnostic agents include but are not limited to, fluorescent moieties, luminescent moieties, magnetic moieties; gadolinium chelates (e.g., gadolinium chelates with DTPA, DTPA-BMA, DOTA and HP-DO3A), iron chelates, magnesium chelates, manganese chelates, copper chelates, chromium chelates, iodine-based materials useful for CAT and x-ray imaging, and radionuclides. Suitable radionuclides include, but are not limited to, $^{123}$I, $^{125}$I, $^{130}$I, $^{131}$I, $^{133}$I, $^{135}$I, $^{47}$Sc, $^{72}$As, $^{72}$Se, $^{90}$Y, $^{88}$Y, $^{97}$Ru, $^{100}$Pd, $^{101}$mRh, $^{119}$Sb, $^{128}$Ba, $^{197}$Hg, $^{211}$At, $^{212}$Bi, $^{212}$Pb, $^{109}$Pd, $^{111}$In, $^{67}$Ga, $^{68}$Ga, $^{67}$Cu, $^{75}$Br, $^{77}$Br, $^{99}$mTc, $^{14}$C, $^{13}$N, $^{15}$O, $^{32}$P, $^{33}$P, and $^{18}$F.

Fluorescent and luminescent moieties include, but are not limited to, a variety of different organic or inorganic small molecules commonly referred to as "dyes," "labels," or "indicators." Examples include, but are not limited to, fluorescein, rhodamine, acridine dyes, Alexa dyes, cyanine dyes, etc. Fluorescent and luminescent moieties may include a variety of naturally occurring proteins and derivatives thereof, e.g., genetically engineered variants. For example, fluorescent proteins include green fluorescent protein (GFP), enhanced GFP, red, blue, yellow, cyan, and sapphire fluorescent proteins, reef coral fluorescent protein, etc. Luminescent proteins include luciferase, aequorin and derivatives thereof. Numerous fluorescent and luminescent dyes and proteins are known in the art (see, e.g., U.S. Patent Publication 2004/0067503; Valeur, B., "Molecular Fluorescence: Principles and Applications," John Wiley and Sons, 2002; and Handbook of Fluorescent Probes and Research Products, Molecular Probes, 9th edition, 2002).

The term "purified" as used herein, refers to other molecules, e.g. polypeptide, nucleic acid molecule that have been identified and separated and/or recovered from a component of its natural environment. Thus, in one embodiment the antibodies of the invention are purified antibodies wherein they have been separated from one or more components of their natural environment.

The term "epitope" as used herein refers to a protein determinant capable of binding to an antibody. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

In some instances, the disclosure provides nucleotide sequences corresponding to (e.g., encoding) the disclosed peptides (e.g., disclosed in Table 1). These sequences include all degenerate sequences related to the disclosed peptides, i.e., all nucleic acids having a sequence that encodes one particular peptide and variants and derivatives thereof. Thus, while each particular nucleic acid sequence may not be written out herein, it is understood that each and every sequence is in fact disclosed and described herein through the disclosed polypeptide sequences.

In some instances, nucleic acids of the disclosed can include expression vectors. Examples of suitable vectors include, but are not limited to, plasmids, artificial chromosomes, such as BACs, YACs, or PACs, and viral vectors.

The provided vectors also can include, for example, origins of replication and/or markers. A marker gene can confer a selectable phenotype, e.g., antibiotic resistance, on a cell. The marker product is used to determine if the vector has been delivered to the cell and once delivered is being expressed. Examples of selectable markers for mammalian cells are dihydrofolate reductase (DHFR), thymidine kinase, neomycin, neomycin analog G418, hygromycin, puromycin, and blasticidin. When such selectable markers are successfully transferred into a mammalian host cell, the transformed mammalian host cell can survive if placed under selective pressure. Examples of other markers include, for example, the *E. coli* lacZ gene, green fluorescent protein (GFP), and luciferase. In addition, an expression vector can include a tag sequence designed to facilitate manipulation or detection (e.g., purification or localization) of the expressed polypeptide. Tag sequences, such as GFP, glutathione S-transferase (GST), polyhistidine, c-myc, hemagglutinin, or FLAG™ tag (Kodak; New Haven, Conn.) sequences typically are expressed as a fusion with the encoded polypeptide. Such tags can be inserted anywhere within the polypeptide including at either the carboxyl or amino terminus.

In some instances, the disclosure includes cells comprising the nucleic acids (e.g., vectors) and/or peptides disclosed herein. Cells can include, for example, eukaryotic and/or prokaryotic cells. In general, cells that can be used herein are commercially available from, for example, the American Type Culture Collection (ATCC), P.O. Box 1549, Manassas, Va. 20108. See also F. Ausubel et al., Current Protocols in Molecular Biology, John Wiley & Sons, New York, N.Y., (1998). Transformation and transfection methods useful in the generation of the cells disclosed herein are described, e.g., in F. Ausubel et al., Current Protocols in Molecular Biology, John Wiley & Sons, New York, N.Y., (1998).

Pharmaceutical Formulations

In some instances, therapeutic compositions disclosed herein can include other compounds, drugs, and/or agents used for the treatment of cancer. Such compounds, drugs, and/or agents can include, for example, chemotherapy drugs, small molecule drugs or antibodies that stimulate the immune response to a given cancer. In some instances, therapeutic compositions can include, for example, one or more peptides disclosed herein and one or more of an anti-CTLA-4 antibody or peptide, an anti-PD-1 antibody or peptide, and/or an anti-PDL-1 antibody or peptide. For example, in some instances, therapeutic compositions disclosed herein can be combined with one or more (e.g., one, two, three, four, five, or less than ten) compounds.

In some instances, therapeutic compositions disclosed herein can include other compounds including histone deacetylase inhibitors ("HDAC") inhibitors. Examples of HDAC inhibitors include, for example, hydroxamic acid, Vorinostat (Zolinza); suberoylanilide hydroxamic acid (SAHA)(Merck), Trichostatin A (TSA), LAQ824 (Novartis), Panobinostat (LBH589) (Novartis), Belinostat (PXD101)(XCuraGen), ITF2357 Italfarmaco SpA (Cinisello), Cyclic tetrapeptide; Depsipeptide (romidepsin, FK228)

(Gloucester Pharmaceuticals), Benzamide; Entinostat (SNDX-275/MS-275)(Syndax Pharmaceuticals), MGCD0103 (Celgene), Short-chain aliphatic acids, Valproic acid, Phenyl butyrate, AN-9, pivanex (Titan Pharmaceutical), CHR-3996 (Chroma Therapeutics), and CHR-2845 (Chroma Therapeutics).

In some instances, therapeutic compositions disclosed herein can include other compounds including proteasome inhibitors, including, for example, Bortezomib, (Millennium Pharmaceuticals), NPI-0052 (Nereus Pharmaceuticals), Carfilzomib (PR-171)(Onyx Pharmaceuticals), CEP 18770, and MLN9708

In some instances, the therapeutic compositions disclosed herein can include alkylating agents such as mephalan and topoisomerase inhibitors such as Adriamycin (doxorubicin) have been shown to increase MICA expression, which could enhance efficacy of an anti-MICA monoclonal antibody.

In some instances, therapeutic compositions disclosed herein can be formulated for use as or in pharmaceutical compositions. Such compositions can be formulated or adapted for administration to a subject via any route, e.g., any route approved by the Food and Drug Administration (FDA). Exemplary methods are described in the FDA's CDER Data Standards Manual, version number 004 (which is available at fda.give/cder/dsm/DRG/drg00301.htm).

In some instances, pharmaceutical compositions can include an effective amount of one or more peptides. The terms "effective amount" and "effective to treat," as used herein, refer to an amount or a concentration of one or more peptides for a period of time (including acute or chronic administration and periodic or continuous administration) that is effective within the context of its administration for causing an intended effect or physiological outcome.

In some instances, pharmaceutical compositions can include one or more peptides and any pharmaceutically acceptable carrier, adjuvant and/or vehicle. In some instances, pharmaceuticals can further include one or more additional therapeutic agents in amounts effective for achieving a modulation of disease or disease symptoms.

The term "pharmaceutically acceptable carrier or adjuvant" refers to a carrier or adjuvant that may be administered to a patient, together with a peptide of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-l-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as I-, ∂-, and K-cyclodextrin, may also be advantageously used to enhance delivery of compounds of the formulae described herein.

The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intra-articular, intraarterial, intrasynovial, intrasternal, intrathecal, intralesional and intracranial injection or infusion techniques.

Pharmaceutical compositions can be in the form of a solution or powder for inhalation and/or nasal administration. Such compositions may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

Pharmaceutical compositions can be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

Alternatively or in addition, pharmaceutical compositions can be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

In some embodiments, the present disclosure provides methods for using any one or more of the peptides or pharmaceutical compositions (indicated below as 'X') disclosed herein in the following methods: Substance X for use as a medicament in the treatment of one or more diseases or conditions disclosed herein (e.g., cancer, referred to in the following examples as 'Y').

Use of substance X for the manufacture of a medicament for the treatment of Y; and substance X for use in the treatment of Y.

In some instances, therapeutic compositions disclosed herein can be formulated for sale in the US, import into the US, and/or export from the US.

Methods

In some instances, methods can include selection of a human subject who has or had a condition or disease and who exhibits or exhibited a positive immune response towards the condition or disease. In some instances, suitable subjects include, for example, subjects who have or had a condition or disease but that resolved the disease or an aspect thereof, present reduced symptoms of disease (e.g., relative to other subjects (e.g., the majority of subjects) with the same condition or disease), and/or that survive for extended periods of time with the condition or disease (e.g., relative to other subjects (e.g., the majority of subjects) with the same condition or disease), e.g., in an asymptomatic state (e.g., relative to other subjects (e.g., the majority of subjects) with the same condition or disease). In some instances, subjects can be selected if they have been vaccinated (e.g., previously vaccinated and/or vaccinated and re-vaccinated (e.g., received a booster vaccine)) against a condition or disease.

The term "subject," as used herein, refers to any animal. In some instances, the subject is a mammal. In some instances, the term "subject", as used herein, refers to a human (e.g., a man, a woman, or a child). Samples for use in the methods can include serum samples, e.g., obtained from the selected subject.

In some instances, subject selection can include obtaining a sample from a subject (e.g., a candidate subject) and testing the sample for an indication that the subject is suitable for selection. In some instances, the subject can be confirmed or identified, e.g. by a health care professional, as having had or having a condition or disease. In some instances, exhibition of a positive immune response towards a condition or disease can be made from patient records, family history, and/or detecting an indication of a positive immune response. In some instances multiple parties can be included in subject selection. For example, a first party can obtain a sample from a candidate subject and a second party can test the sample. In some instances, subjects can be selected and/or referred by a medical practitioner (e.g., a general practitioner). In some instances, subject selection can include obtaining a sample from a selected subject and storing the sample and/or using the in the methods disclosed herein. Samples can include, for example, cells or populations of cells.

In some instances, obtaining or targeting immune cells can include one or more and/or combinations of, for example: obtaining or providing a tetrameric immunogen that can bind (e.g., bind specifically) to a target immune cell; contacting the tetrameric immunogen with a sample; detecting the tetrameric immunogen; determining whether the tetrameric immunogen is bound to a target immune cell; and, if the tetrameric immunogen is bound to a target immune cell, then obtaining the target immune cell.

Tetrameric immunogens can include immunogens related to a condition or disease and/or that bind (e.g., bind specifically) to a target immune cell, e.g., wherein the target immune cell is related to a selected condition or disease. Immunogens and target immune cells related to a condition or disease include, for example, immunogens or immune cells present in subjects with a certain condition or disease, but not subjects without the condition or disease; and/or immunogens or immune cells present at altered levels (e.g., increased) in subjects with a certain condition or disease relative to subjects without the condition or disease. In some instances, immunogens or immune cells can be cancer specific. Immunogens can be soluble. Tetrameric immunogen can include tetrameric (including, e.g., tetramerized monomeric, dimeric, and/or trimeric antigen immunogen (e.g., antigen and/or epitope). In some instances, a tetrameric immunogen has increased binding to a cell relative to the level of binding between a non-tetrameric form of the immunogen to the cell under similar conditions. In some instances, a tetrameric antigen includes a detectable moiety, e.g., a streptavidin moiety. Tetramerization methods are known in the art and are disclosed herein.

Detecting tetrameric immunogen and/or determining whether tetrameric immunogen is bound to a target cell can be performed using methods known in the art and/or disclosed herein. For example, methods can include flow cytometry. Optimization methods for flow cytometry, including sorting and gating methods, are known in the art and/or are disclosed herein. In some instances, methods can include analysis of the level of binding, binding affinity, and/or binding specificity between a tetrameric immunogen bound to a target immune cell. For example, a target immune cell can be obtained if (e.g., only if) a pre-determined level of binding between a tetrameric immunogen and a target immune cell is determined. Pre-determined levels of binding can be specific levels and/or can be relative levels. Obtaining target immune cells can include obtaining, providing, identifying, selecting, purifying, and/or isolating the target immune cells. Such methods can include, for example, cell sorting methods, cell enrichment, and/or background reduction.

In some instances, obtaining immune cells directed against a self antigen can include one or more and/or combinations of, for example, identifying a subject exhibiting a positive immune response towards the self antigen; obtaining or providing a multimeric form of the self antigen; contacting the multimeric form of the self antigen with a sample from the subject exhibiting a positive immune response towards the self antigen; obtaining immune cells bound to the multimeric form of the self antigen.

In some instances, methods can include obtaining immune cells directed against a self antigen from a cancer patient, can include one or more and/or combinations of, for example, identifying a subject exhibiting a positive immune response towards the self antigen; providing a multimeric form of the self antigen; contacting the multimeric form of the self antigen with a sample from the subject exhibiting a positive immune response towards the self antigen; and obtaining immune cells bound to the multimeric form of the self antigen.

Multimeric forms of a self antigen can include self antigens related to a condition or disease and/or that bind (e.g., bind specifically) to a target immune cell, e.g., wherein the target immune cell is related to a selected condition or disease. Self antigens and target immune cells related to a condition or disease include, for example, antigens or immune cells present in subjects with a certain condition or disease, but not subjects without the condition or disease; and/or immunogens or immune cells present at altered levels (e.g., increased) in subjects with a certain condition or disease relative to subjects without the condition or disease. In some instances, the condition or disease can be a cancer. In some embodiments, the cancer is melanoma, lung, breast, kidney, ovarian, prostate, pancreatic, gastric, and colon carcinoma, lymphoma or leukemia. In some instances, the self antigens or immune cells can be cancer specific. The self antigens can be soluble. Multimeric form of the self antigen can include a tetrameric form (including, e.g., tetramerized monomeric, dimeric, and/or trimeric antigen) of the self-antigen (e.g., antigen and/or epitope). In some instances, a multimeric form of the self antigen includes a detectable moiety, e.g., a streptavidin moiety. Multimerization methods are known in the art and are disclosed herein.

Methods for isolating or purifying genetic material (e.g., DNA and/or mRNA) from the obtained target immune cell are known in the art and are exemplified herein. Once such genetic material has been obtained, methods for using it to produce the therapeutic compositions disclosed herein are known in the art and/or are summarized below. As discussed above, genetic material can be varied, using techniques known in the art to create peptide variants disclosed herein.

Generating peptides from nucleic acids (e.g., cDNA) contained within or obtained from the target cell can include, for example, analysis, e.g., sequencing of heavy and light chain variable domains from target immune cells (e.g., single or isolated identified target immune cells). In some instances, methods can include generating fully human antibodies, or fragments thereof (e.g., as disclosed above), and humanization of non-human antibodies. DNA can be readily isolated and/or sequenced from the obtained immune cells using conventional procedures (e.g., by using oligonucleotide probes that are capable of binding specifically to genes encoding the heavy and light chains of murine antibodies).

Once isolated, DNA can be placed into expression vectors, which are then transfected into host cells such as *Escherichia coli* cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., Curr. Opinion in Immunol., 5:256-262 (1993) and Pluckthun, Immunol. Revs., 130:151-188 (1992).

Recombinant expression of an antibody or variant thereof generally requires construction of an expression vector containing a polynucleotide that encodes the antibody. The invention, thus, provides replicable vectors comprising a nucleotide sequence encoding an antibody molecule, a heavy or light chain of an antibody, a heavy or light chain variable domain of an antibody or a portion thereof, or a heavy or light chain CDR, operably linked to a promoter. Such vectors may include the nucleotide sequence encoding the constant region of the antibody molecule (see, e.g., U.S. Pat. Nos. 5,981,216; 5,591,639; 5,658,759 and 5,122,464) and the variable domain of the antibody may be cloned into such a vector for expression of the entire heavy, the entire light chain, or both the entire heavy and light chains.

Once the expression vector is transferred to a host cell by conventional techniques, the transfected cells are then cultured by conventional techniques to produce an antibody. Thus, the invention includes host cells containing a polynucleotide encoding an antibody of the invention or fragments thereof, or a heavy or light chain thereof, or portion thereof, or a single-chain antibody of the invention, operably linked to a heterologous promoter. In certain embodiments for the expression of double-chained antibodies, vectors encoding both the heavy and light chains may be co-expressed in the host cell for expression of the entire immunoglobulin molecule, as detailed below.

Mammalian cell lines available as hosts for expression of recombinant antibodies are well known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), human epithelial kidney 293 cells, and a number of other cell lines. Different host cells have characteristic and specific mechanisms for the post-translational processing and modification of proteins and gene products. Appropriate cell lines or host systems can be chosen to ensure the correct modification and processing of the antibody or portion thereof expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, W138, BT483, Hs578T, HTB2, BT2O and T47D, NSO (a murine myeloma cell line that does not endogenously produce any functional immunoglobulin chains), SP20, CRL7O3O and HsS78Bst cells. In one embodiment, human cell lines developed by immortalizing human lymphocytes can be used to recombinantly produce monoclonal antibodies. In one embodiment, the human cell line PER.C6. (Crucell, Netherlands) can be used to recombinantly produce monoclonal antibodies.

In some instances, peptides disclosed herein can be generated synthetically. Synthetic chemistry transformations and protecting group methodologies (protection and deprotection) useful in synthesizing peptides described herein are known in the art and include, for example, those such as described in R. Larock, Comprehensive Organic Transformations, VCH Publishers (1989); T. W. Greene and P. G. M. Wuts, Protective Groups in Organic Synthesis, 3d. Ed., John Wiley and Sons (1999); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

Peptides can also be made by chemical synthesis methods, which are well known to the ordinarily skilled artisan. See, for example, Fields et al., Chapter 3 in Synthetic Peptides: A User's Guide, ed. Grant, W. H. Freeman & Co., New York, N.Y., 1992, p. 77. Hence, peptides can be synthesized using the automated Merrifield techniques of solid phase synthesis with the α-$NH_2$ protected by either t-Boc or Fmoc chemistry using side chain protected amino acids on, for example, an Applied Biosystems Peptide Synthesizer Model 430A or 431.

One manner of making of the peptides described herein is using solid phase peptide synthesis (SPPS). The C-terminal amino acid is attached to a cross-linked polystyrene resin via an acid labile bond with a linker molecule. This resin is insoluble in the solvents used for synthesis, making it relatively simple and fast to wash away excess reagents and by-products. The N-terminus is protected with the Fmoc group, which is stable in acid, but removable by base. Any side chain functional groups are protected with base stable, acid labile groups.

Longer peptides could be made by conjoining individual synthetic peptides using native chemical ligation. Alternatively, the longer synthetic peptides can be synthesized by well-known recombinant DNA techniques. Such techniques are provided in well-known standard manuals with detailed protocols. To construct a gene encoding a peptide of this invention, the amino acid sequence is reverse translated to obtain a nucleic acid sequence encoding the amino acid sequence, preferably with codons that are optimum for the organism in which the gene is to be expressed. Next, a synthetic gene is made, typically by synthesizing oligonucleotides which encode the peptide and any regulatory elements, if necessary. The synthetic gene is inserted in a suitable cloning vector and transfected into a host cell. The peptide is then expressed under suitable conditions appropriate for the selected expression system and host. The peptide is purified and characterized by standard methods.

The peptides can be made in a high-throughput, combinatorial fashion, e.g., using a high-throughput multiple channel combinatorial synthesizer available from Advanced Chemtech.

Peptide bonds can be replaced, e.g., to increase physiological stability of the peptide, by: a retro-inverso bonds (C(O)—NH); a reduced amide bond (NH—CH$_2$); a thiomethylene bond (S—CH$_2$ or CH$_2$—S); an oxomethylene bond (O—CH$_2$ or CH$_2$—O); an ethylene bond (CH$_2$—CH$_2$); a thioamide bond (C(S)—NH); a trans-olefin bond (CH═CH); a fluoro substituted trans-olefin bond (CF═CH); a ketomethylene bond (C(O)—CHR) or CHR—C(O) wherein R is H or CH$_3$; and a fluoro-ketomethylene bond (C(O)—CFR or CFR—C(O) wherein R is H or F or CH$_3$.

Peptides can be further modified by: acetylation, amidation, biotinylation, cinnamoylation, farnesylation, fluoresceination, formylation, myristoylation, palmitoylation, phosphorylation (Ser, Tyr or Thr), stearoylation, succinylation and sulfurylation. As indicated above, peptides can be conjugated to, for example, polyethylene glycol (PEG): alkyl groups (e.g., C1-C20 straight or branched alkyl groups); fatty acid radicals; and combinations thereof.

In some instances, peptides can be purified by any method known in the art for purification of an immunoglobulin molecule, for example, by chromatography (e.g., ion exchange, affinity, particularly by affinity for the specific antigens Protein A or Protein G, and sizing column chromatography), centrifugation, differential solubility, or by any other standard technique for the purification of proteins. Further, the antibodies of the present invention or fragments thereof may be fused to heterologous polypeptide sequences (referred to herein as "tags") described above or otherwise known in the art to facilitate purification.

An exemplary, non-limiting, overview of the methods is shown in FIG. 21. Ordering is not implied.

Methods of Use

In some instances, the disclosure provides methods of treatment that include administering to a subject a composition disclosed herein.

Provided herein are methods for treating and/or preventing cancer or symptoms of cancer in a subject comprising administering to the subject a therapeutically effective amount of a composition comprising a peptide that immunospecifically binds to MHC class I polypeptide-related sequence A (MICA), wherein the peptide comprises complementarity determining region (CDR) 3 of the V$_H$ of antibody ID 1, 6, 7, 8 or 9 shown in Table 1 having 5 or fewer conservative amino acid substitutions, and CDR3 of the V$_L$ of antibody ID 1, 6, 7, 8 or 9 shown in Table 1 having 5 or fewer conservative amino acid substitutions. In some embodiments the cancer is a cancer associated with overexpression of MICA. In some embodiments, the cancer is melanoma, lung, breast, kidney, ovarian, prostate, pancreatic, gastric, and colon carcinoma, lymphoma or leukemia. In some embodiments, the cancer is melanoma. In some embodiments, the cancer is a plasma cell malignancy, for example, multiple myeloma (MM) or pre-malignant condition of plasma cells. In some embodiments the subject has been diagnosed as having a cancer or as being predisposed to cancer.

In some instances, the disclosure provides methods for treating and/or preventing cancer or symptoms of cancer in a subject comprising administering to the subject a therapeutically effective amount of a composition comprising an isolated antibody which specifically binds to MHC class I polypeptide-related sequence A (MICA), wherein the antibody comprises a heavy chain variable region (VH) comprising the VH CDR1, VH CDR2, and VH CDR3 as shown in the VH sequence of SEQ ID NO: 11, 149, 168, 186, or 204 and a light chain variable region (VL) sequence of SEQ ID No: 4, 151, 170, 189, or 206.

Also provided herein are methods for treating and/or preventing cancer or symptoms of cancer in a subject comprising administering to the subject a therapeutically effective amount of a peptide that immunospecifically binds to angiopoietin, wherein the peptide comprises complementarity determining region (CDR) 3 of the VH of antibody ID 2, 3, 4 or 5 or 10 shown in Table 1 having 5 or fewer conservative amino acid substitutions, and CDR3 of the VL of antibody ID 2, 3, 4 or 5 shown in Table 1 having 5 or fewer conservative amino acid substitutions. In some embodiments the cancer is a cancer associated with overexpression of MICA. In some embodiments, the cancer is melanoma, lung, breast, kidney, ovarian, prostate, pancreatic, gastric, and colon carcinoma, lymphoma or leukemia. In some embodiments, the cancer is melanoma. In some embodiments, the cancer is a plasma cell malignancy, for example, multiple myeloma (MM) or pre-malignant condition of plasma cells. In some embodiments the subject has been diagnosed as having a cancer or as being predisposed to cancer.

In some instances, the disclosure provides methods for treating and/or preventing cancer or symptoms of cancer in a subject comprising administering to the subject a therapeutically effective amount of a composition comprising an isolated antibody which specifically binds to angiopoietin (e.g., angiopoietin-2), wherein the antibody comprises a heavy chain variable region (VH) comprising the VH CDR1, VH CDR2, and VH CDR3 as shown in the VH sequence of SEQ ID NO: 20, 38, 56, 74, 222 and a light chain variable region (VL) sequence of SEQ ID No: 29, 47, 65, 83, or 224.

Symptoms of cancer are well-known to those of skill in the art and include, without limitation, unusual mole features, a change in the appearance of a mole, including asymmetry, border, color and/or diameter, a newly pigmented skin area, an abnormal mole, darkened area under nail, breast lumps, nipple changes, breast cysts, breast pain, death, weight loss, weakness, excessive fatigue, difficulty eating, loss of appetite, chronic cough, worsening breathlessness, coughing up blood, blood in the urine, blood in stool, nausea, vomiting, liver metastases, lung metastases, bone metastases, abdominal fullness, bloating, fluid in peritoneal cavity, vaginal bleeding, constipation, abdominal distension, perforation of colon, acute peritonitis (infection, fever, pain), pain, vomiting blood, heavy sweating, fever, high blood pressure, anemia, diarrhea, jaundice, dizziness, chills, muscle spasms, colon metastases, lung metastases, bladder metastases, liver metastases, bone metastases, kidney metastases, and pancreatic metastases, difficulty swallowing, and the like.

The methods disclosed herein can be applied to a wide range of species, e.g., humans, non-human primates (e.g., monkeys), horses, cattle, pigs, sheep, deer, elk, goats, dogs, cats, mustelids, rabbits, guinea pigs, hamsters, rats, and mice.

The terms "treat" or "treating," as used herein, refers to partially or completely alleviating, inhibiting, ameliorating, and/or relieving the disease or condition from which the subject is suffering. In some instances, treatment can result in the continued absence of the disease or condition from which the subject is suffering.

In general, methods include selecting a subject at risk for or with a condition or disease. In some instances, the subject's condition or disease can be treated with a pharmaceutical composition disclosed herein. For example, in some instances, methods include selecting a subject with cancer, e.g., wherein the subject's cancer can be treated by targeting one or both of MICA and/or angiopoetin-2.

In some instances, treatments methods can include a single administration, multiple administrations, and repeating administration as required for the prophylaxis or treatment of the disease or condition from which the subject is suffering. In some instances treatment methods can include assessing a level of disease in the subject prior to treatment, during treatment, and/or after treatment. In some instances, treatment can continue until a decrease in the level of disease in the subject is detected.

The terms "administer," "administering," or "administration," as used herein refers to implanting, absorbing, ingesting, injecting, or inhaling, the inventive peptide, regardless of form. In some instances, one or more of the peptides disclosed herein can be administered to a subject topically (e.g., nasally) and/or orally. For example, the methods herein include administration of an effective amount of compound or compound composition to achieve the desired or stated effect. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Following administration, the subject can be evaluated to detect, assess, or determine their level of disease. In some instances, treatment can continue until a change (e.g., reduction) in the level of disease in the subject is detected.

Upon improvement of a patient's condition (e.g., a change (e.g., decrease) in the level of disease in the subject), a maintenance dose of a compound, composition or combination of this invention may be administered, if necessary. Subsequently, the dosage or frequency of administration, or both, may be reduced, as a function of the symptoms, to a level at which the improved condition is retained. Patients may, however, require intermittent treatment on a long-term basis upon any recurrence of disease symptoms.

In some instances, the disclosure provides methods for detecting immune cells e.g., B cells and/or memory B cells, from a human subject. Such methods can be used, for example, to monitor the levels of immune cells e.g., B cells and/or memory B cells, in a human subject, e.g., following an event. Exemplary events can include, but are not limited to, detection of diseases, infection; administration of a therapeutic composition disclosed herein, administration of a therapeutic agent or treatment regimen, administration of a vaccine, induction of an immune response. Such methods can be used clinically and/or for research.

EXAMPLES

The invention is further described in the following examples, which do not limit the scope of the invention described in the claims.

Methods are described herein that allow sensitive, specific, and reliable detection of rare memory B cells, with defined antigen specificity, from limited quantities of peripheral blood. Methods allowed visualization and isolation of memory B cells months to years after antigen had been cleared.

Proof of principle for the methods disclosed herein was established using tetramers of tetanus toxin C-fragment (TTCF), as reported in detail in Franz et al. (Blood, 118(2): 348-357 (2011)), which reference is hereby incorporated by reference in its entirety.

TTCF (i.e., the 52 kDa, non-toxic, C-terminal fragment of TTCF) was selected as a model antigen because the majority of individuals have been vaccinated with tetanus toxoid and persistent IgG antibody titers are induced by the vaccine (Amanna et al., N. Engl. J. Med., 357:1903-1915, 2007). Accordingly, use of TTCF afforded a large pool of subjects in which the methods disclosed herein could be verified. One of skill in the art will appreciate, however, that the present methods can be adapted to include any disease-related antigen using routine skill. As demonstrated in the examples below, such adaption has been shown through the acquisition of antibodies directed against MICA and angiopoietin-2, which are cancer-related antigens.

Example 1

Antigen Expression and Tetramer Formation

As described in further detail below, TTCF was expressed in *Escherichia coli* and a BirA site was attached to the N-terminus for site-specific mono-biotinylation by BirA enzyme. A flexible linker was placed between the protein and the biotinylation site to prevent steric hindrance of antibody binding. TTCF was purified by anion-exchange chromatography, biotinylated with BirA, and separated from free biotin and BirA by gel filtration chromatography. TTCF tetramers were generated by incubating fluorescently tagged streptavidin with biotinylated TTCF antigen at a molar ratio of 1:4. These tetramers were then used along with a panel of mAbs for the identification of tetanus toxoid specific memory B cells.

TTCF was cloned in pET-15b (Novagen). Protein expression was induced in BL21(DE3) *Escherichia coli* with 1 mM isopropyl β-D-1-thiogalactopyranoside (IPTG) for 4 hours at 28° C. Cells were washed, lysed, and resulting supernatant was collected. TTCF was purified using a HIS-Select affinity column (Sigma). The His-tag was removed proteolytically. Murine CD80 membrane proximal domain was produced using similar methods. Proteins were mono-biotinylated. For certain experiments, Alexa-488 dye molecules (Molecular probes) were linked to primary amines on biotinylated TTCF or CD80.

Antigen tetramers were prepared by incubating biotinyated antigen with premium grade PE labeled streptavidin (Molecular Probes) for at least 20 minutes on ice at a molar ratio of 4:1. Prior to use, tetramer preparations were centrifuged to remove aggregates. In some experiments, tetramers were formed with Alexa-fluor-488 tagged antigens and non-fluorescent streptavidin at a 4:1 ratio.

Example 2

Identification Methods

Methods were performed as described in Franz et al., Blood, 118(2):348-357 (2011).

Cells were sorted on a BD FACS Aria II cell sorter. Cells were single-cell sorted. Samples were first gated on CD19+ cells that were negative for a panel of exclusion markers (CD3, CD14, CD16, 7AAD) then gated on plasmablasts, identified by high levels of CD27 and an immediate level of CD19 expression, and finally on tetramer+ CD19+ cells.

Due to the low frequency of memory B cells, it was necessary to carefully reduce background as much as possible. B cells were first enriched by negative selection (cocktail of antibodies to CD2, CD3, CD14, CD16, CD56 and glycophorin A) to remove most cells that could non-specifically bind the tetramer. Enriched cells were split evenly and stained with TTCF or a control tetramer followed by labeling with CD19, CD27 and IgM to specifically select class-switched memory B cells. The gating strategy considered expression of CD19, lack of labeling with a panel of exclusion markers (CD3, CD14, CD16, 7AAD), expression of the memory marker CD27 and lack of IgM expression as evidence of class switching. Tetramer staining was plotted versus CD27 staining for visualization of memory B cells with the antigen specificity of interest. Tetramer-positive B cells were directly sorted into PCR strips containing 3 µl mRNA extraction buffer.

Tubes were kept cold during sorting and sorted cells were frozen and stored at −80° C. CD19+ CD27+ IgM-B cells were used as positive controls.

A previously reported nest PCR protocol was used to amplify heavy and light chain variable segments (Wang et al., J. Immunol. Methods., 244:217-225, 2000). mRNA amplification was carried out under conditions suitable to minimize contamination. Primers used included:

(SEQ ID NO: 91)
TAATACGACTCACTATAGGTTCGGGGAAGTAGTCCTTGACCAGG;

(SEQ ID NO: 92)
TAATACGACTCACTATAGGGATAGAAGTTATTCAGCAGGCACAC;

(SEQ ID NO: 93)
TAATACGACTCACTATAGGCGTCAGGCTCAGRTAGCTGCTGGCCGC.

Nested RT-PCR was performed as described in Franz et al., Blood, 118(2):348-357 (2011).

Negative controls were included to monitor and guard against contamination. From a total of 35 single cells labeled with the TTCF tetramer, 32 heavy and 30 light chain segments were amplified and directly sequence from gel-purified PCR products, corresponding to an overall PCR efficiency of 89%. Sequence analysis revealed that TTCF tetramer+ cells employed a variety of different $V_H D\text{-}J_H$ gene segments, without dominance of one particular gene segment. Sequences observed supported that clones represented cells diversified by somatic hypermutation.

Antibody production and purification included cloning heavy and light variable domain DNA into separate pcDNA3.3 expression vectors containing the bovine prolactin signal peptide sequence as well as full length IgG1 heavy or kappa light chain constant domains. Antibodies were expressed in CHO-S media (Invitrogen) supplemented with 8 mM Glutamax (Gibco) in 100 ml sinner flasks at 37° C. with 8% $CO_2$. One day prior to transfection, cells were split to $6\times10^5$ cells/ml. On the day of transfection, cells were adjusted, were necessary, to $1\times10^6$ cells/ml. 25 µg of heavy and light chain plasmid DNA were co-transfected using MAX transfection reagent (Invitrogen) and transfected cells were cultured for 6-8 days. Protein was obtained using Protein G sepharose beads and antibody was eluted using 100 mM glycine pH2.5 and separated from beads using Spin-X centrifuge tubes. Purified antibody was exchanged into phosphate buffered saline (PBS) using Micro Bio-Spin columns (BioRad). Protein concentration was assessed by absorbance at 280 nm.

For saturation binding assay, non-biotinylated, MonoQ purified TTCF was labeled with europium and free europium was removed. 96-well flat bottom plates were coated overnight with 20 ng of antibody per well in 100 mM $NaHCO_3$ buffer at pH 9.6. Blocking was performed with assay buffer supplemented with bovine serum albumin (BSA) and bovine gamma globulins. TTCF-europium was diluted in assay buffer (100 nM to 4 pM) and 200 µl was added per well in triplicate. Plates were incubated for 2 hours at 37° C. and washed three times with 200 µl wash buffer (50 mM Tris pH 8, 150 mM NaCl, 20 µM EDTA, 0.05% Tween). 100 µl enhancement solution was added to each well and fluorescence counts measured using a Victor$^3$ plate reader at 615 nm.

Heavy and light chain variable domain sequences were analyzed using IMGTN-Quest and JIONSOLVER software. Flow cytometry data were evaluated using FlowJo analysis software. Statistical analyses were carried out using Graph-Pad Prism 5 software using unpaired t-test. To determine antibody $K_D$ values, saturation binding data were fitted using GraphPad Prism 5 software using non-linear regression analysis.

Example 3

Multimerization Enhances Identification of Memory B Cells

Tetrameric and monomeric TTCF were compared. TTCF was fluorescently labeled with Alexa-488 and then used in monomeric form or was converted to a tetramer using unlabeled streptavidin (see above). Enriched B cells were then incubated with tetrameric or monomeric TTCF-Alexa-488 at the same concentration. Control protein (CD80 membrane proximal domain) was labeled in the same way and also used as a tetramer.

As shown in FIGS. 22A and 22B, TTCF labeled some memory B cells, but frequencies identified with tetramer were substantially larger (1.6-7.3 fold) using cells from three donors. In one of the three donors TTCF specific memory B cells could be detected with the tetramer but not with the monomer.

These results demonstrate that antigen tetramers enable sensitive detection of memory B cells based on the antigen specificity of their BCR, despite such cells being very rare in peripheral blood. Class-switched memory B cells specific for TTCF were brightly labeled by the appropriate tetrameric TTCF antigen, while background labeling with control tetramer was consistently low.

Example 4

Method/Antibody Validation

Fully human antibodies were generated by joining constant regions of IgG heavy and kappa chains to isolated variable segments via overlap PCR. Antibodies were expressed in a transient, serum free mammalian expression system using CHO-S cells for a period of 6-8 days. Antibodies were purified using protein G and gel filtration chromatography.

Figure 23B:
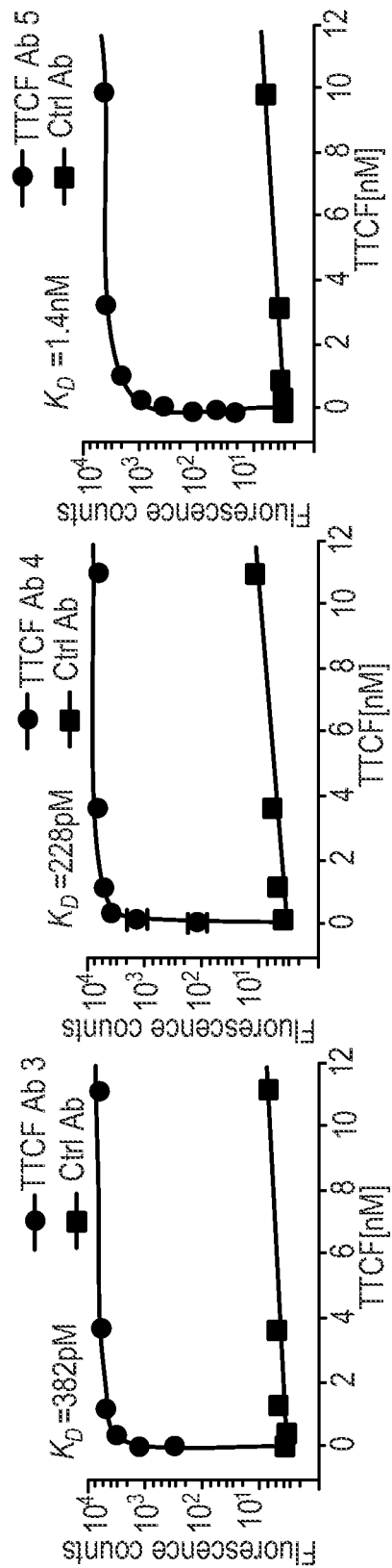

As shown in FIG. 23, antibodies isolated from TTCF-specific plasmablasts showed high binding affinities to TTCF antigen, with a $K_D$ of 2.2 nM (TTCF Ab 1) and 323 pM (TTCF Ab 2)(FIG. 23B. Antibodies isolated from memory B cells also exhibited high binding affinities, with $K_D$ of 382 pM, 228 pM, and 1.4 nM, for other antibodies (TTCF Abs 3, 4, and 5)(FIG. 23B).

These data support the specificity of the methods disclosed herein. Moreover, the specificity of the methods herein was demonstrated by the construction of five anti-TTCF antibodies from three different donors, all of which bound to TTCF with high affinities.

Data herein also demonstrate that antigen tetramers enable sensitive detection of memory B cells long after clearance of the antigen from the host.

Example 5

Obtaining Anti-MICA Antibodies

Antibodies that immunospecifically bind to MICA were developed using the methods herein.

Briefly, MICA antigen (UniGene Hs.130838) was expressed with a C-terminal BirA tag (GLNDIFEAQKIEWHE (SEQ ID NO: 238)), which enables mono-biotinylation of the antigen. Antigen was tetramerized with streptavidin (SA) labeled with R-Phycoerythrin (PE) at a molar ration of 4 MICA: 1 SA. Peripheral blood mononuclear cells were obtained from advanced stage melanoma patients who had been vaccinated with autologous tumor cells transduced with a GM-CSF expression vector (GVAX) (PNAS 103: 9190, 2006), and subsequently treated with the anti-CTLA-4 monoclonal antibody ipilimumab (YERVOY™ (available from Bristol Myers Squib)) Peripheral blood mononuclear cells were quickly thawed, washed and resuspended at $5 \times 10^6$ in phosphate buffered saline (pH 7.2) supplemented with 2% fetal calf serum and stained with approximately 0.1 ug/ml tetramer for 30 minutes on ice. Antibodies were added to identify class-switched, memory B-cells (CD19+, CD27+, and IgM−). A panel of exclusion antibodies labeling T-cells, natural killer-cells, marcrophages, and dead cells were included to reduce background tetramer staining (CD3, CD14, CD16, 7-AAD). Single B-cells that bound to the MICA tetramer were sorted into 8-tube-PCR strips using the BD FACS Aria II. The B-cell receptor (BCR) mRNA was amplified using a commercial kit from Epicentre Biotechnologies (catalog number: MBCL90310) using gene specific primers shown below:

mRNA Amplification
IgG-T7:
(SEQ ID NO: 94)
AATACGACTCACTATAGGTTCGGGGAAGTAGTCCTTGACCAGG Kappa-T7:
(SEQ ID NO: 95)
TAATACGACTCACTATAGGGATAGAAGTTATTCAGCAGGCACAC Lambda-T7:
(SEQ ID NO: 96)
TAATACGACTCACTATAGGCGTCAGGCTCAGRTAGCTGCTGGCCGC PCR One
VHL-1:
(SEQ ID NO: 97)
TCACCATGGACTG(C/G)ACCTGGA

VHL-2:
(SEQ ID NO: 98)
CCATGGACACACTTTG(C/T)TCCAC

VHL-3:
(SEQ ID NO: 99)
TCACCATGGAGTTTGGGCTGAGC

VHL-4:
(SEQ ID NO: 100)
AGAACATGAAACA(C/T)CTGTGGTTCTT

VHL-5:
(SEQ ID NO: 101)
ATGGGGTCAACCGCCATCCT

VHL-6:
(SEQ ID NO: 102)
ACAATGTCTGTCTCCTTCCTCAT

VkL-1:
(SEQ ID NO: 103)
GCTCAGCTCCTGGGGCTCCTG

VkL-2:
(SEQ ID NO: 104)
CTGGGGCTGCTAATGCTCTGG

VkL-3:
(SEQ ID NO: 105)
TTCCTCCTGCTACTCTGGCTC

VkL-4:
(SEQ ID NO: 106)
CAGACCCAGGTCTTCATTTCT

VlL-1:
(SEQ ID NO: 107)
CCTCTCCTCCTCACCCTCCT

VlL-2:
(SEQ ID NO: 108)
CTCCTCACTCAGGGCACA

VlL-3:
(SEQ ID NO: 109)
ATGGCCTGGA(T/C)C(C/G)CTCTCC

CgII:
(SEQ ID NO: 110)
GCCAGGGGGAAGAC(C/G)GATG

CkII:
(SEQ ID NO: 111)
TTTCAACTGCTCATCAGATGGCGG

ClII:
(SEQ ID NO: 112)
AGCTCCTCAGAGGAGGG(C/T)GG

PCR Two
VH-1:
(SEQ ID NO: 113)
CAGGT(G/C)CAGCTGGT(G/A)CAGTC

VH-2:
(SEQ ID NO: 114)
CAG(A/G)TCACCTTGAAGGAGTC

VH-3:
(SEQ ID NO: 115)
(G/C)AGGTGCAGCTGGTGGAGTC

VH-4:
(SEQ ID NO: 116)
CAGGTGCAGCTGCAGGAGTC

-continued

VH-5:
(SEQ ID NO: 117)
GA(G/A)GTGCAGCTGGTGCAGTC

VH-6:
(SEQ ID NO: 118)
CAGGTACAGCTGCAGCAGTC

Vk-1:
(SEQ ID NO: 119)
CG(A/C)CATCC(A/G)G(A/T)TGACCCAGT

Vk-2:
(SEQ ID NO: 120)
CGAT(A/G)TTGTGATGAC(C/T)CAG

Vk-3:
(SEQ ID NO: 121)
CGAAAT(T/A)GTG(T/A)TGAC(G/A)CAGTCT

Vk-4:
(SEQ ID NO: 122)
CGACATCGTGATGACCCAGT

Vl-1:
(SEQ ID NO: 123)
CCAGTCTGTGCTGACTCAGC

Vl-2:
(SEQ ID NO: 124)
CCAGTCTGCCCTGACTCAGC

Vl-3:
(SEQ ID NO: 125)
CTCCTATGAGCTGAC(T/A)CAGC

CgIII:
(SEQ ID NO: 126)
GAC(C/G)GATGGGCCCTTGGTGGA

CkIII:
(SEQ ID NO: 127)
AAGATGAAGACAGATGGTGC

ClIII:
(SEQ ID NO: 128)
GGGAACAGAGTGACCG

The primers and PCR cycling conditions used in PCR one and PCR two are adapted from Wang and Stollar et al. (journal of immunological methods 2000).

An alternate heavy chain variable region forward primer set was developed to cover heavy chain variable region sequences potentially not adequately covered by the above primer set. The following alternate primers were generated:

PCR One
VHL1-58:
(SEQ ID NO: 129)
TCACTATGGACTGGATTTGGA

VHL2-5:
(SEQ ID NO: 130)
CCATGGACA(C/T)ACTTTG(C/T)TCCAC

VHL3-7:
(SEQ ID NO: 131)
GTAGGAGACATGCAAATAGGGCC

VHL3-11:
(SEQ ID NO: 132)
AACAAAGCTATGACATATAGATC

VHL3-13.1:
(SEQ ID NO: 133)
ATGGAGTTGGGGCTGAGCTGGGTT

VHL3-13.2:
(SEQ ID NO: 134)
AGTTGTTAAATGTTTATCGCAGA

VHL3-23:
(SEQ ID NO: 135)
AGGTAATTCATGGAGAAATAGAA

VHL4-39:
(SEQ ID NO: 136)
AGAACATGAAGCA(C/T)CTGTGGTTCTT

VHL4-61:
(SEQ ID NO: 137)
ATGGACTGGACCTGGAGCATC

VHL-9:
(SEQ ID NO: 138)
CCTCTGCTGATGAAAACCAGCCC

PCR Two
VH1-3/18:
(SEQ ID NO: 139)
CAGGT(C/T)CAGCT(T/G)GTGCAGTC

VH1-45/58:
(SEQ ID NO: 140)
CA(A/G)ATGCAGCTGGTGCAGTC

VH2-5:
(SEQ ID NO: 141)
CAG(A/G)TCACCTTGA(A/G)GGAGTCTGGT

VH3-9/23/43:
(SEQ ID NO: 142)
GA(A/G)GTGCAGCTG(T/G)TGGAGTC

VH3-16:
(SEQ ID NO: 143)
GAGGTACAACTGGTGGAGTC

VH3-47:
(SEQ ID NO: 144)
GAGGATCAGCTGGTGGAGTC

V4-34:
(SEQ ID NO: 145)
CAGGTGCAGCTACAGCAGTG

V4-30-2/39:
(SEQ ID NO: 146)
CAGCTGCAGCTGCAGGAGTC

VH7-4-1:
(SEQ ID NO: 147)
CAGGTGCAGCTGGTGCAATC

Briefly, 2 ul cDNA generated via mRNA amplification was used as a template for first-round PCR, with the following cycling conditions: 3 cycles of preamplification (94° C./45 seconds, 45° C./45 seconds, 72° C./105 seconds); 30 cycles of amplification (94° C./45 seconds, 50° C./45 seconds, 72° C./105 seconds); 10 minutes of final extension at 72° C.

3 ul of first-round PCR product served as a template for the second round of nested PCR. The same cycling conditions were used for the first round of PCR, but the 3 cycles of preamplification were omitted. Both PCR steps were performed by the use of cloned Pfu polymerase AD (Agilent Technologies). PCR products were separated on 1% agarose gels and products of 300-400 nucleotides in size isolated with the use of Zymoclean DNA gel recovery kit (Zymo Research). Sequencing was performed by the use of forward and reverse primers used for the second-round nested PCR. A two-step nested PCR amplifies the BCR variable domains of heavy and light chains (see above). Peripheral blood mononuclear cells were obtained from advanced stage melanoma patients who had been vaccinated with autologous tumor cells transduced with a GM-CSF expression vector (GVAX) (PNAS 103: 9190, 2006). The antibodies were expressed as full-length IgG1 antibodies in a transient CHO-S expression system.

Validation of anti-MICA antibody binding to MICA was performed using two independent bead-based assays. The first assay used a commercially available solution-based bead assay kit designed for detection of anti-MICA antibodies reactive to a variety of MICA alleles (One Lambda, catalog number LSMICA001). Varying concentrations of the MICA antibody were incubated with beads, then washed, and incubated with an anti-human IgG antibody conjugated with phycoerythrin. Following a second wash step, beads were analyzed on a Luminex machine. A negative control consisted of incubation of beads with anti-human IgG antibody conjugated with phycoerythrin alone (no anti-MICA antibody). A positive control consisted of incubation of beads with a commercially available anti-MICA/MICB monoclonal antibody (clone 6D4) directly conjugated to phycoerythrin (BioLegend catalog #320906). The second assay was developed internally using polystyrene beads conjugated with streptavidin. Beads were coated with mono-biotinylated MICA protein, and incubated with varying concentrations of anti-MICA antibody, anti-TTCF antibody (isotype negative control), or BioLegend anti-MICA/MICB antibody directly conjugated to phycoerythrin (positive control). Beads incubated with anti-MICA antibody or anti-TTCF antibody were washed and then incubated with anti-human IgG antibody conjugated with Alexa488. To determine background binding to the beads, the same incubation was performed using streptavidin-conjugated beads not coated with MICA protein for comparison. Beads were analyzed for binding to antibodies on a FACS Caliber flow cytometer.

Figure 24:
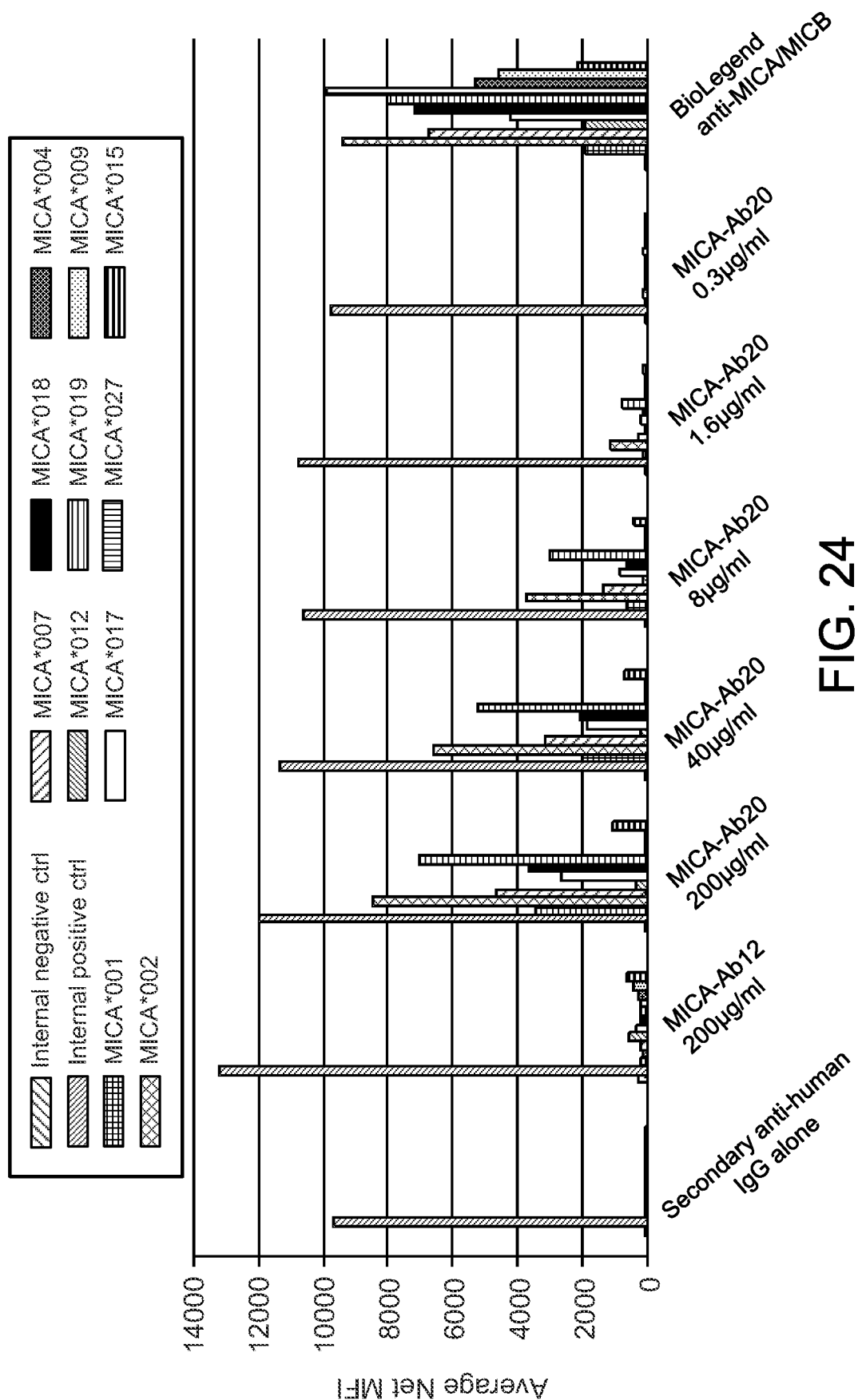
FIG. 24|Bar chart showing binding of anti-MICA antibodies to MICA-coated luminex beads.
Figures 25K, 25L, 25M, 25N, 25O:
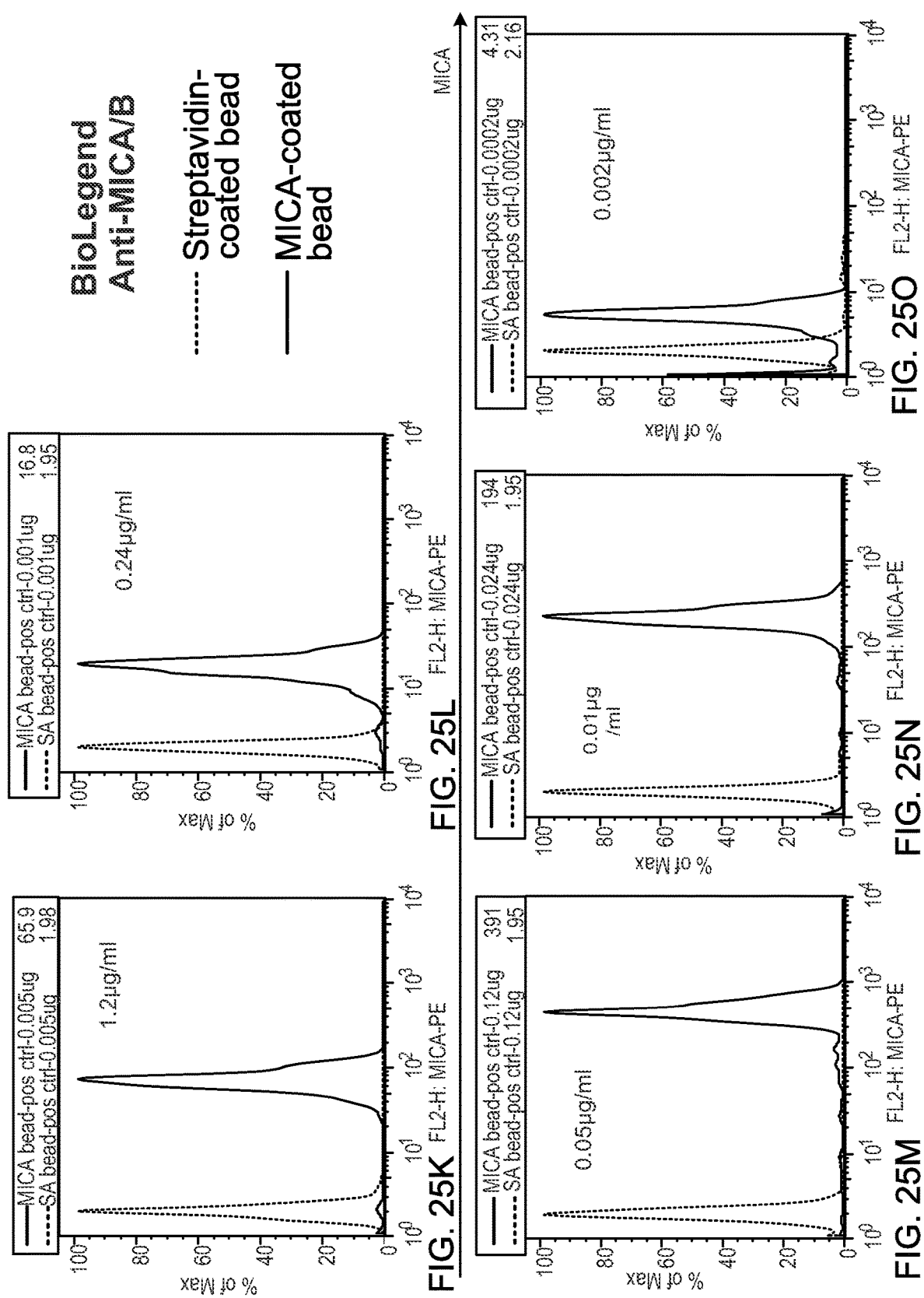

As shown in FIGS. 24 and 25, anti-MICA antibodies (MICA-Ab12 and MICA-Ab20) bind with high affinity to MICA. MICA-Ab20 corresponds to the anti-MICA antibody ID-1 described in Table 1.

Example 6

Anti-MICA Antibodies

Additional anti-MICA antibodies with clinically relevant biological properties were developed using the methods herein. MICA-specific antibodies reactive to common alleles were identified in patients who had received a cellular cancer vaccine (GM-CSF transduced cancer cells, referred to as GVAX) and an antibody that blocks the inhibitory CTLA-4 receptor on T cells ipilimumab (YERVOY™ (available from Bristol Myers Squib)). MICA tetramers were then used to isolate B cells from peripheral blood mononuclear cells of patients with the highest serum MICA reactivity. Heavy and light chain sequences were determined from these B cells by single cell PCR, as outlined in the in Example 5. This effort led to the identification of antibodies that recognize alleles common in the North American population.

CM24002 Ab2 (anti-MICA antibody ID-6 described in Table 1) is an antibody isolated from a patient with acute myeloid leukemia (AML) who demonstrated a significant clinical response to the GVAX+Ipilimumab combination therapy and whose plasma reacted strongly with MICA. The CM24002 Ab2 light chain (FIGS. 30 and 31) and heavy chain (FIGS. 28 and 29) nucleotide and amino acid sequences are shown, with CDR1, CDR2 and CDR3 sequences underlined. An additional antibody with strong binding was obtained from the same patient and is labeled as CM24002 Ab4 (anti-MICA antibody ID-7 described in Table 1) The CM24002 Ab4 light chain (FIGS. 34 and 35) and heavy chain (FIGS. 23 and 32) nucleotide and amino acid sequences are shown, with CDR1, CDR2 and CDR3 sequences underlined.

CM33322 Ab11 (anti-MICA antibody ID-8 described in Table 1) and CM33322 Ab29 (anti-MICA antibody ID-9 described in Table 1) are antibodies isolated from a patient with metastatic melanoma who is a long-term responder (>15 years) to the GVAX+Ipilimumab combination therapy. The CM33322 Ab11 light chain ((FIGS. 38 and 39) and heavy chain (FIGS. 36 and 37) nucleotide and amino acid sequences are shown, with CDR1, CDR2 and CDR3 sequences underlined. The CM33322 Ab29 light chain ((FIGS. 42 and 43) and heavy chain (FIGS. 40 and 41) nucleotide and amino acid sequences are shown, with CDR1, CDR2 and CDR3 sequences underlined. Due to the long-term clinical response of this patient, these antibodies are of particular interest.

After initial identification, cloning, and expression of the antibodies of interest, the specificity of these antibodies for different MICA alleles was determined with a cytometric bead assay. Briefly, soluble, recombinant MICA alleles 002, 008, 009 and MICB with a single BirA biotinylation site were expressed, purified, and captured on streptavidin beads. Indicated anti-MICA antibodies were then incubated with the beads coated with recombinant MICA at different concentrations for one hour, then washed, and incubated with a FITC-labeled anti-human IgG secondary antibody. Following a second wash step, quantification of bead-bound FITC fluorescence was completed by flow cytometry. MICA alleles 002, 008, 009 as well as the related MICB protein were chosen based on their prevalence in the North American population (FIG. 48). MICA alleles 002, 008, 009 as well as the related MICB protein were also chosen based on their generally high prevalence worldwide. Importantly, CM24002 Ab2 and CM33322 Ab29 bound strongly to all MICA alleles as well as to MICB. The other two antibodies bound to a subset of alleles: CM24002 Ab4 bound highly to MICA*009 and MICB, and CM33322 Ab11 bound highly to MICA*002, MICA*008, and MICB. (FIGS. 48A-F) Specificity was documented by use of a negative human control antibody generated with the same technology (specific for tetanus toxoid C-terminal fragment, TTCF) and a positive control antibody to MICA (a commercial murine antibody from BioLegend directed against MICA). These studies identified CM24002 Ab2 and CM33322 Ab29 as potential candidates for clinical application.

Example 7

Binding of Anti-MICA Antibody to Autologous Tumor Cells

Figure 49:
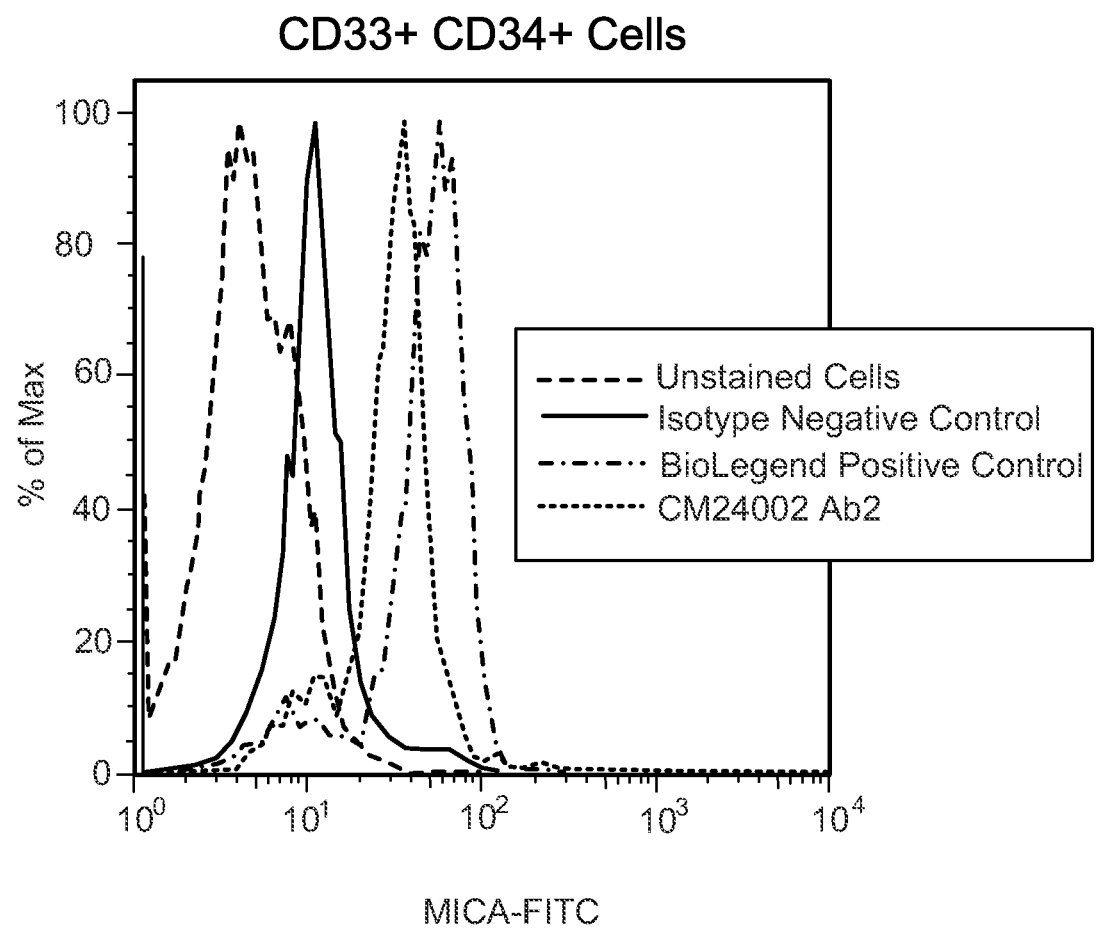
FIG. 49|Line graph showing labeling of autologous tumor cells by anti-MICA antibody CM24002 Ab2.

The ability of isolated anti-MICA antibody CM24002 Ab2 to bind to autologous tumor cells was examined by flow cytometry (FIG. 49). Bone marrow obtained from patient CM24002 and tested binding to tumor cells by CM24002 Ab2. Tumor cells were then identified from the bone marrow sample as CD33+CD34+ cells. The tumor cells were then stained with 10 μg/ml with anti-MICA antibody CM24002 Ab2, positive control commercial MICA antibody (BioLegend) or a negative control antibody (TTCF specific). As shown in FIG. 49, CM24002 Ab2 strongly bound to these cells. CM24002 Ab2 did not display binding to non-tumor cells (CD16+ and CD3+ cells) and only background binding to CD14+ cells, demonstrating anti-tumor specificity (data not shown).

Example 8

Anti-MICA Antibody Inhibition of NKG2D Receptor on NK Cells

Figure 50:
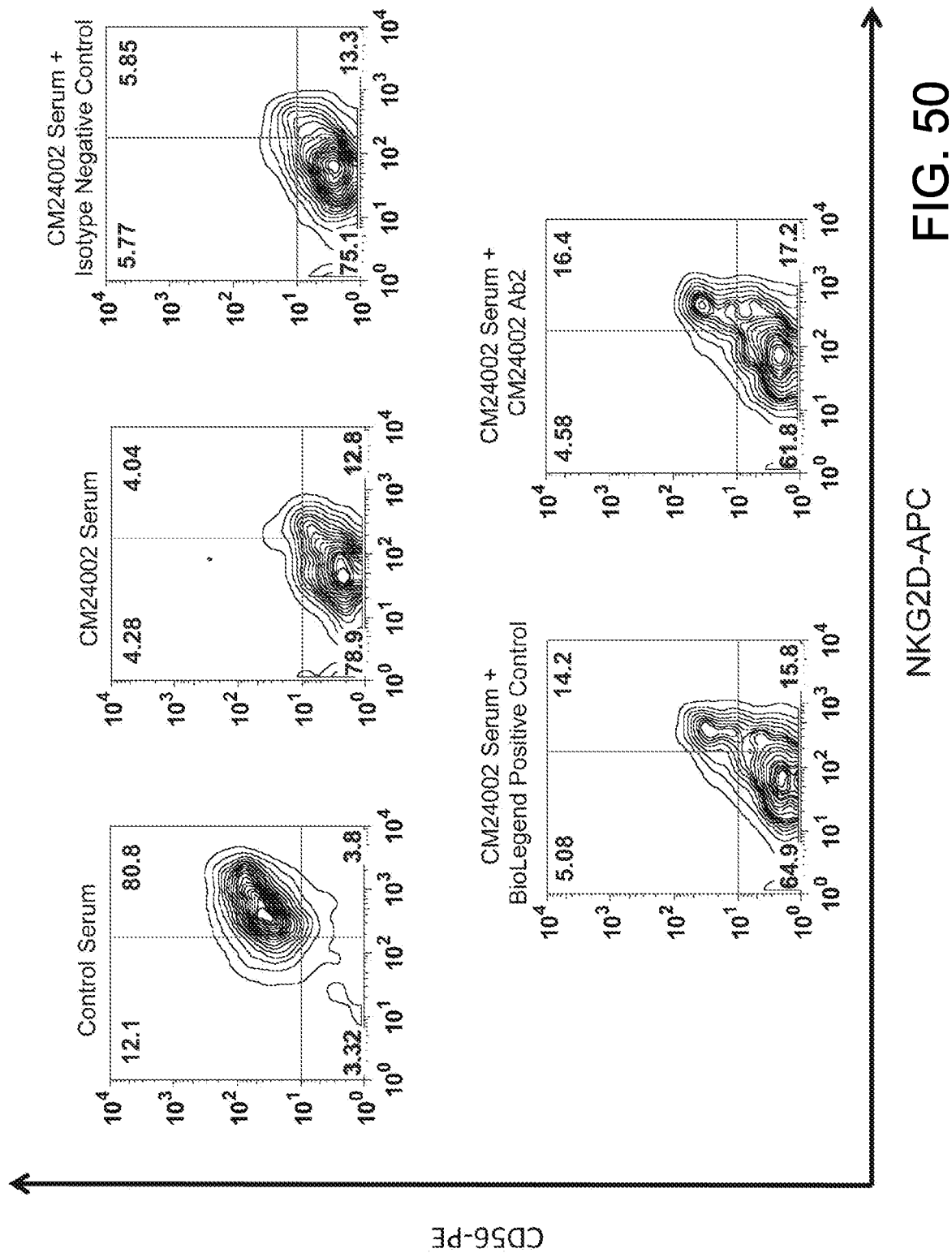
FIG. 50|A series of FACS plot showing regulation of NKG2D by serum MICA. Human NK cells were incubated with control serum from patient CM24002 and a 1:10 dilution for 48 hours. Indicated antibodies were added at the start of the incubation at a concentration of 10 µg/ml. NKG2D expression was assessed on CD56+ NK cells by flow cytometry.
Figure 51:
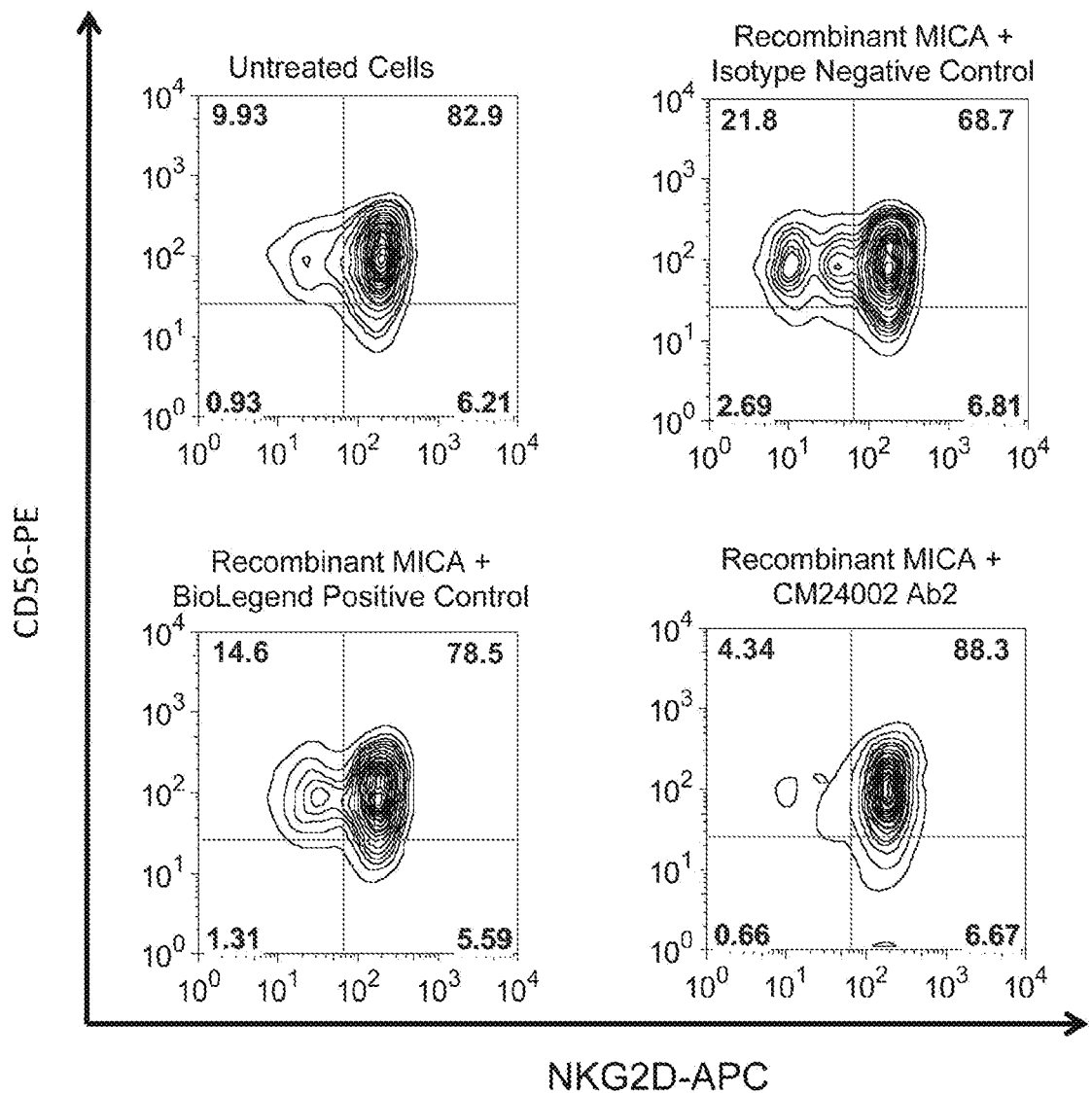
FIG. 51|A series of FACS plot showing regulation of NKG2D by recombinant MICA. Human NK cells were incubated with recombinant MICA at a concentration of 2 ng/ml for 48 hours. Indicated antibodies were added at the start of the incubation at a concentration of 10 µg/ml. After 48 hours, NKG2D expression was assessed on CD56+ NK cells by flow cytometry.

The ability of isolated anti-MICA antibody CM24002 Ab2 to prevent soluble MICA-mediated down-regulation of is cognate receptor, NKG2D was examined. Serum from patient CM24002 was used at a 1:10 dilution and incubated with human NK cells for a period of 48 hours. CM24002 Ab2 (concentration of 10 µg/ml), positive control commercial MICA antibody (BioLegend) or a negative control antibody (TTCF specific) were added to these cultures. NKG2D expression was assessed by flow cytometry at 48 hr (FIG. 50). Serum from patient CM24002 strongly down-regulated expression of NKG2D (thus disabling the function of this receptor). CM24002 Ab2 and the positive control MICA antibody partially restored NKG2D surface expression by NK cells. To demonstrate specificity, we repeated the above experiment by incubating cells with recombinant MICA at 2 ng/ml instead of patient serum (FIG. 51). CM24002 Ab2 completely prevented MICA-mediated down-regulation of NKG2D expression, while the negative control antibody (specific for TTCF) had no effect (FIG. 51). These data demonstrate that human MICA antibodies can prevent inhibition of the critical NKG2D receptor on human NK cells.

Example 9

Anti-MICA Antibody Cell-Mediated Cytotoxicity

Figure 52:
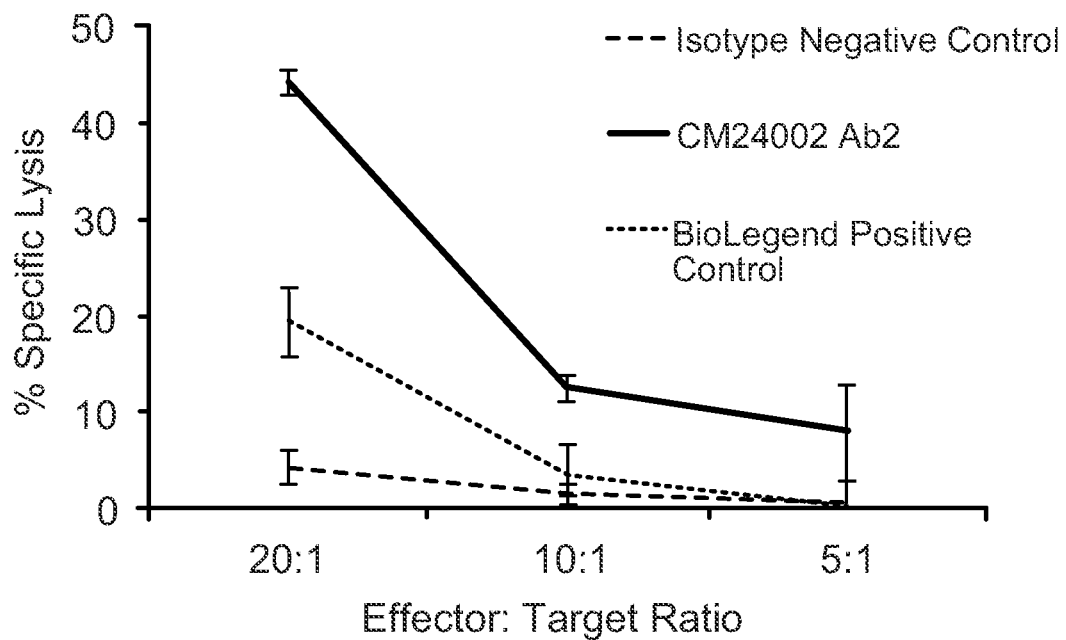
FIG. 52|Line graph demonstrating enhancement of cell-mediated toxicity by anti-MICA antibody CM24002 Ab2. Human NK cells were incubated with recombinant MICA (2 ng/ml) for 48 hours in the presence of indicated antibodies at 10 µg/ml. The ability of NK cells (effectors) to kill K562 target cells was assessed by measuring LDH release following 4 hour incubation at the indicated ratios.
Figure 53:
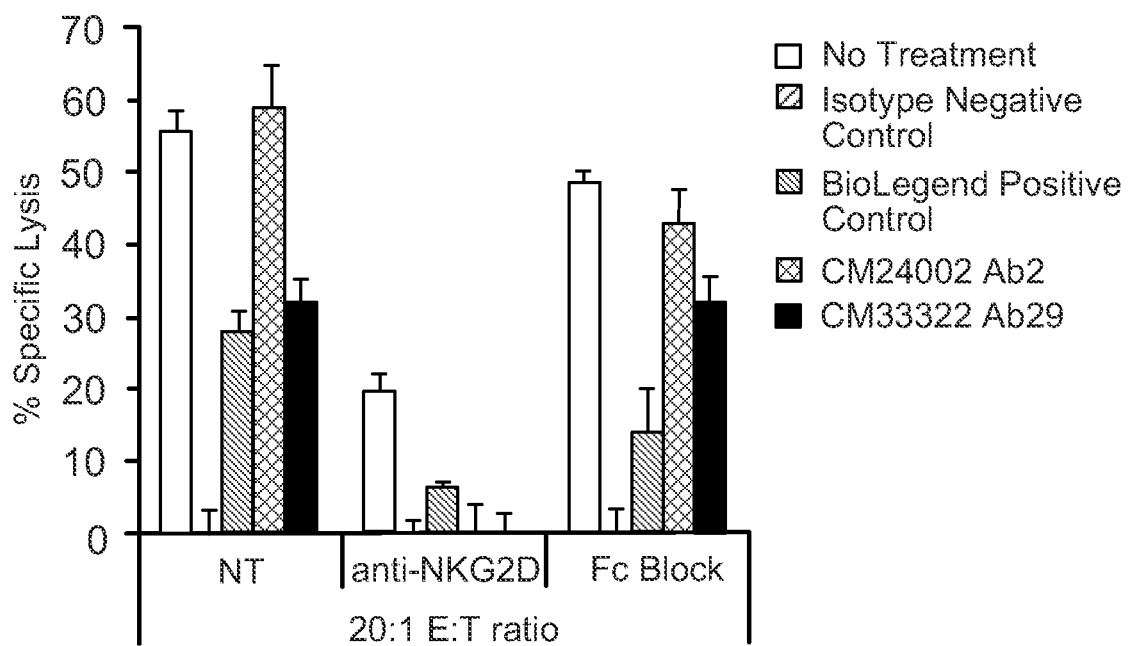
FIG. 53|Bar graph demonstration cell-mediated toxicity by anti-MICA antibodies CM24002 Ab2 and CM33322 Ab29. Human NK cells were incubated with recombinant MICA (2 ng/ml) for 48 hours in the presence of indicated antibodies at 10 µg/ml. The ability of NK cells (effectors) to kill K562 target cells was assessed by measuring LDH release following 4 hour incubation. NKG2D blocking antibody or Fc blocking antibody was added during the 4 hr incubation of effector and target cells to assess the contribution of Fc receptor and NKG2D to cell-mediated toxicity.

To determine if CM24002 Ab2 enables cell-mediated cytotoxicity, human NK cells (effector cells) were incubated for 48 hours with recombinant MICA (2 ng/ml) in the presence of CM24002 Ab2, a negative control antibody (TTCF specific) or a positive control antibody (BioLegend), all at 10 µg/ml. After 48 hours, cells were washed and incubated with K562 tumor cells at 20:1, 10:1, and 5:1 effector:target ratios for 4 hours. Specific lysis of target cells by NK cells was determined by release of a cytosolic protein (LDH) from K562 tumor cells. In the absence of MICA antibodies, there was no killing of K562 tumor cells by NK cells. However, CM24002 Ab2 greatly enhanced NK cell mediated lysis of K562 tumor cells and was more effective than the positive control murine MICA antibody at all effector:target ratios (FIG. 52). It was further demonstrated that killing of K562 tumor cells was indeed mediated by the NKG2D pathway (rather than Fc receptors). The above experiment was repeated, with the addition two experimental groups: a blocking antibody for NKG2D and human Fc block. In addition, CM33322 Ab29 was also tested. The data show that addition of CM24002 Ab2 and CM33322 Ab29 enabled NK cell mediated cytotoxicity. Killing of K562 cells did not occur when a blocking NKG2D antibody was added, while the Fc blocking reagent had little effect (FIG. 53). These data show that CM24002 Ab2 and CM33322 Ab29 restore the anti-tumor function of the NKG2D pathway.

Example 10

Binding of Anti-MICA Antibody to Alpha 3 MICA Domain

Figure 54:
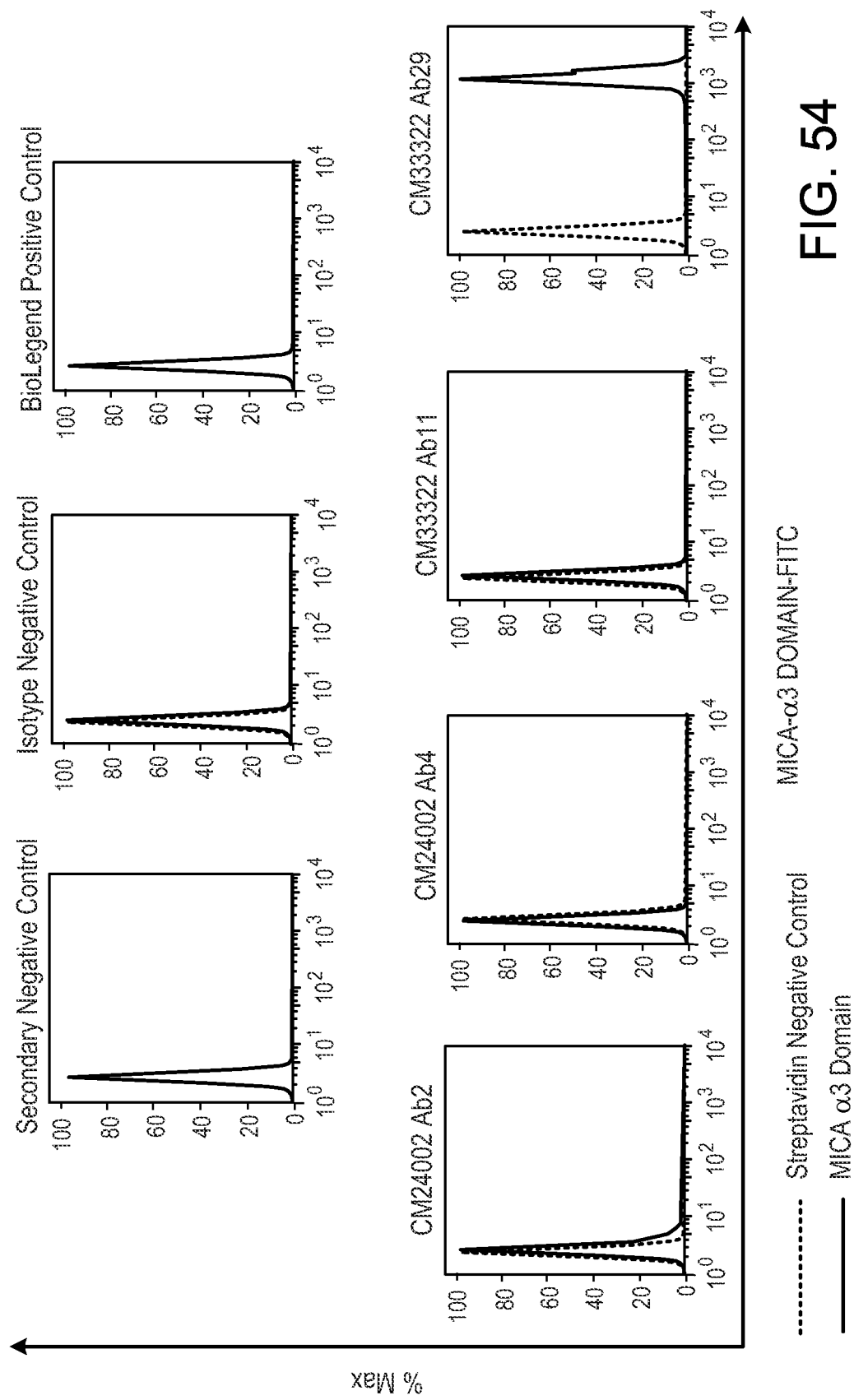
FIG. 54|A series of line graphs showing binding of MICA alpha 3 domain by recombinant anti-MICA antibodies. Recombinant MICA alpha 3 domains were biotinylated and captured on the surface of streptavidin-coated beads. Indicated antibodies were incubated at 10 µg/ml with the beads coated with the individual recombinant protein for 1 hr. Beads were subsequently washed and incubated with FITC-conjugated anti-human IgG secondary antibody. FITC fluorescence was quantified by flow cytometry.

The NKG2D receptor binds to the top alpha 1 and alpha 2 domains of MICA, and antibodies that bind to the same site may compete with the NKG2D receptor and thereby block killing of tumor cells by NK cells. Antibodies that bind to the alpha 3 domain are of particular interest because they cannot block NKG2D receptor binding. At the same time, such antibodies can interfere with proteolytic cleavage of MICA from the tumor cell surface. The ability of anti-MICA antibodies to the MICA alpha 3 domain was assessed using the previously described cytometric bead assay. The biotinylated recombinant protein was captured on streptavidin beads. Beads were then incubated with antibodies CM24002 Ab2, CM24002 Ab4, CM33322 Ab11, CM33322 AB29, a negative control antibody (TTCF specific) or a positive control antibody (BioLegend), at 10 µg/ml followed by a FITC-labeled anti-human IgG secondary antibody and quantification of bead-bound FITC fluorescence by flow cytometry (FIG. 54). As shown in FIG. 54, CM33322 Ab29 bound to the MICA alpha 3 domain and is therefore of great interest for therapeutic applications.

Example 11

Binding of Anti-MICA Antibody to Tumor Cells

Figure 55:
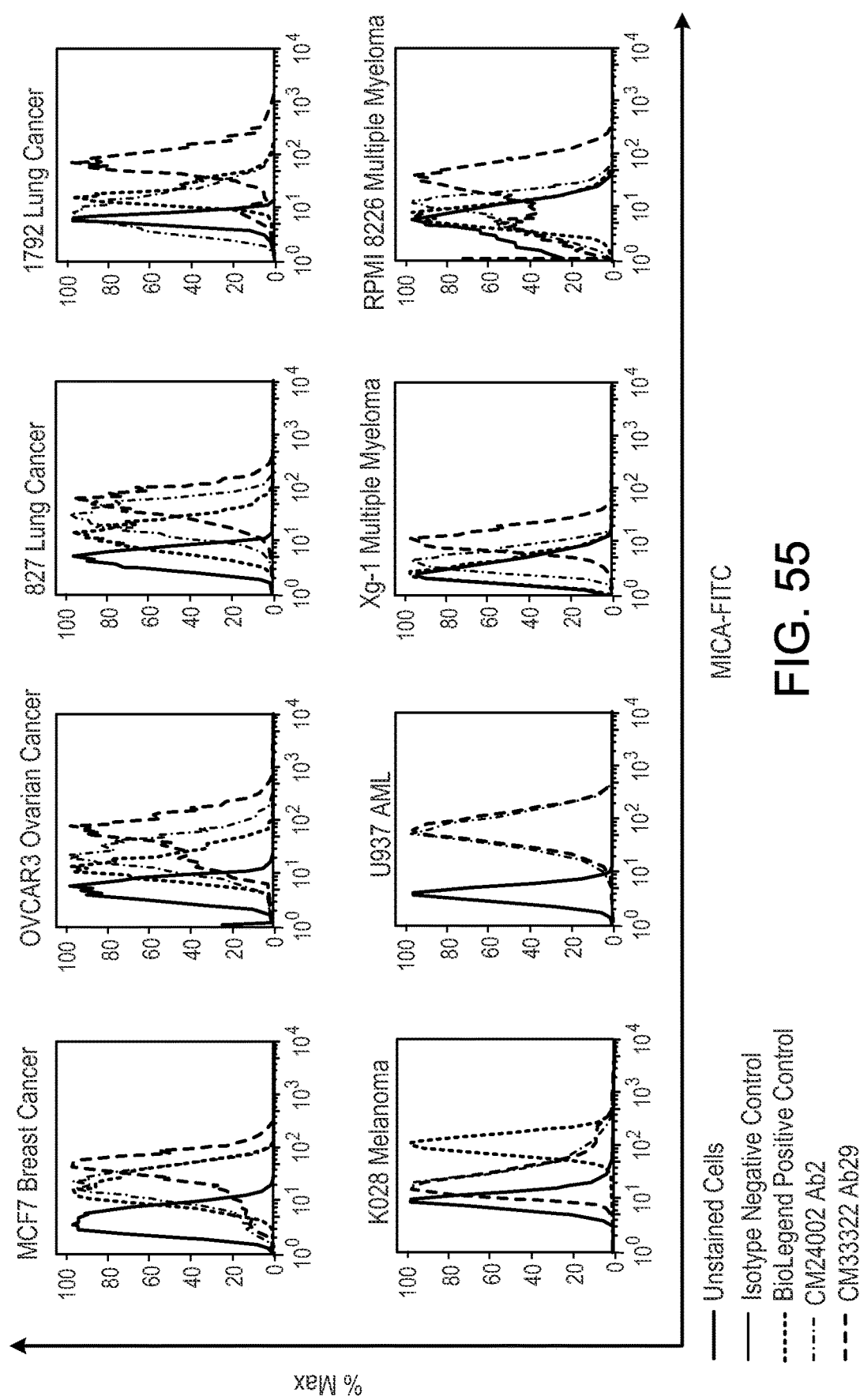
FIG. 55|Line graphs demonstrating labeling of tumor cells by anti-MICA antibodies CM24002 Ab2 and CM33322 Ab29. Fluorescence was determined by flow cytometry.

The potential of CM24002 Ab2 and CM33322 Ab29 to be used to target a broad range of cancers was assessed. A panel of multiple myeloma (RPMI 8226 and Xg-1), ovarian cancer (OVCAR3), acute myeloid leukemia (U937), melanoma (K028), lung cancer (1792 and 827), and breast cancer (MCF7) cells were tested for labeling by CM24002 Ab2 and CM33322 Ab29. The tumor cells were resuspended at a concentration of $1 \times 10^6$ cells/ml in PBS with 1% BSA and stained with the CM24002 Ab2 and CM33322 Ab29, as well as positive and negative controls (murine MICA antibody and TTCF-specific antibody, respectively)(directly conjugated) at a concentration of 10 g/ml for 1 hour at 4° C. Labeling was assessed by flow cytometry (FIG. 55). CM24002 Ab2 and CM33322 Ab29 both bound every tumor cell type tested, with labeling being greater than the commercial positive control for the majority of tested cell lines.

Example 12

MICA Allele Specificity of Anti-MICA Antibody

Figure 56:
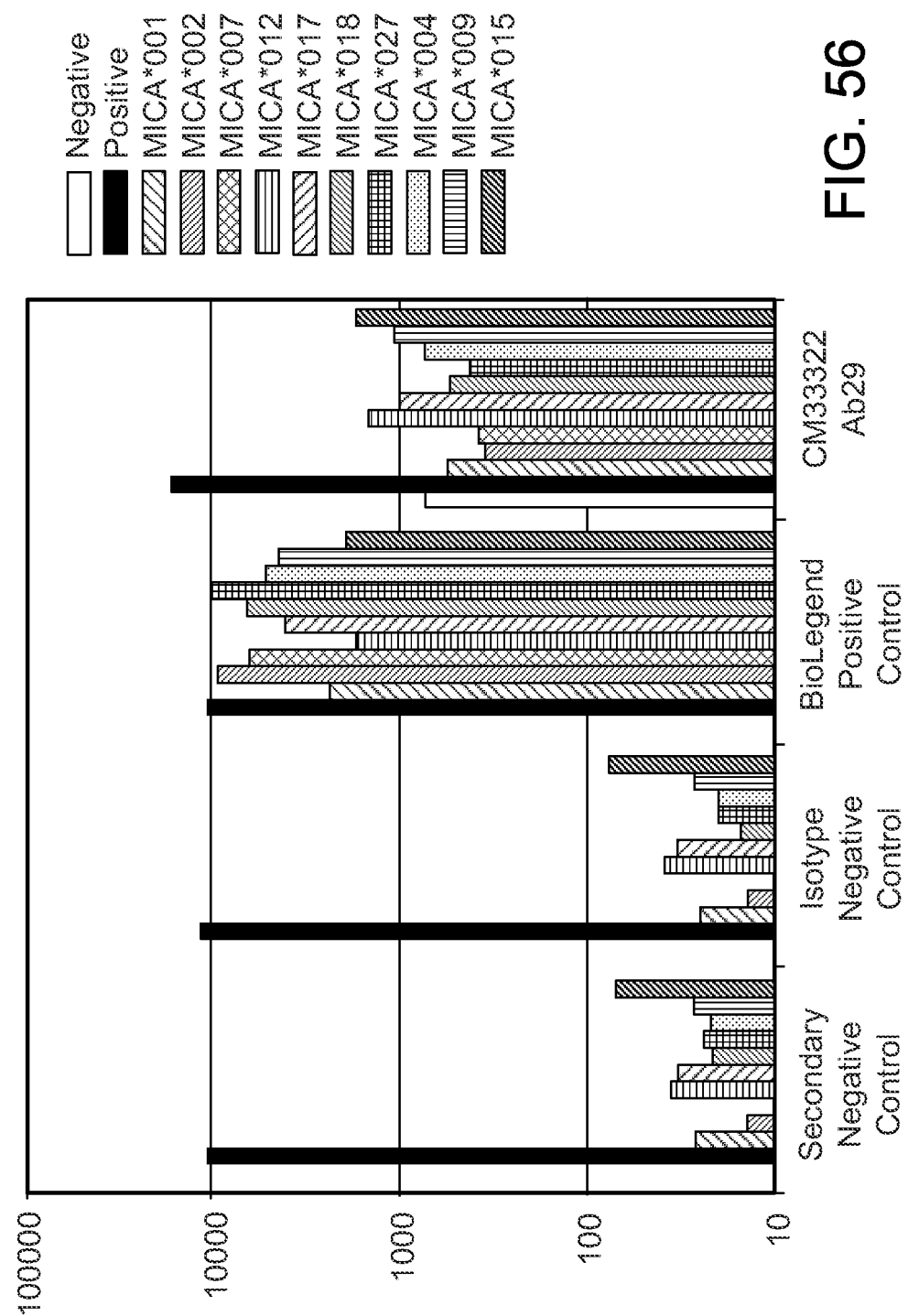
FIG. 56|Bar graph demonstrating MICA allelic specificity of anti-MICA antibodies CM33322 Ab29 as determined by Luminex assay.

The allelic specificity of CM33322 Ab29 was assessed using a commercially available Luminex assay. The commercial test kit contains recombinant MICA alleles (MICA*001, *002, *007, *012, *017, *018, *027, *004, *009, and*015) directly conjugated to Luminex beads, each with intrinsic fluorescent properties enabling binding to be assessed in a single sample. Luminex beads coated with the indicated MICA alleles were incubated with CM33322 Ab29, BioLegend positive control, and the negative control (TTCF), at 10 µg/ml for 1 hr, with subsequent incubation with PE-conjugated anti-human IgG secondary antibody. Fluorescence was determined following incubation for 60 minutes with the indicated antibodies and subsequent incubation with anti-human PE-conjugated secondary antibody using a Luminex 200 instrument (FIG. 56). CM33322 Ab29 was able to bind to all alleles present in the commercial assay, indicating that it may be used in patients regardless of MICA genotype.

These data demonstrate the high biological activity of CM24002 Ab2 and CM33322 Ab29 and their ability to restore NK cell mediated lysis of tumor cells. These data demonstrate that cancer patients who responded to immunotherapies produced MICA antibodies that restored the anti-tumor activity of NK cells. Together, these results highlight the therapeutic potential of anti-MICA antibodies to overcome immune suppression and promote tumor destruction in cancer patients.

Example 13

Obtaining Anti-Angiopoietin-2 Antibodies

Antibodies that bind to angiopoietin-2 were developed using the methods herein. Briefly, biotinylated angiopoietin-2 (UniGene Hs.583870) was purchased from R&D Systems. Peripheral blood mononuclear cells were quickly thawed, washed and resuspended at $5 \times 10^6$ in phosphate buffered saline (pH 7.2) supplemented with 2% fetal calf serum and stained with approximately 0.5 ug/ml angiopoietin-2 for 30 minutes on ice. Cells were washed twice with 4 ml PBS/2% FCS. Then antibodies were added to identify class-switched, memory B-cells (CD19+, CD27+, and IgM−) as well as SA-PE to label B-cells with biotinylated angiopoietin on the surface. A panel of exclusion antibodies labeling T-cells, natural killer-cells, marcrophages, and dead cells were included to reduce background tetramer staining (CD3, CD14, CD16, 7-AAD). Single B-cells that bound to angiopoietin-2 were sorted into 8-tube-PCR strips using the BD FACS Aria II. The B-cell receptor (BCR) mRNA was amplified using a commercial kit from Epicentre Biotechnologies (catalog number: MBCL90310) using gene specific primers (see above). A two-step nested PCR amplifies the BCR variable domains of heavy and light chains (see above). Peripheral blood mononuclear cells were obtained from a patient with malignant non-small cell lung carcinomnoma who had been vaccinated with autologous tumor cells transduced with a GM-CSF expression vector (GVAX) (Cancer Res. 70: 10150, 2010). The antibodies were expressed as full-length IgG1 antibodies in a transient CHO-S expression system.

Validation of anti-angiopoietin-2 antibodies binding to angiopoietin-2 was performed using ELISA assays. Briefly, angiopoietin-2 was coated overnight at 4 µg/ml in 100 mM sodium bicarbonate buffer pH 9.6 in 96-well flat bottom plates (PerkinElmer) at 4° C. Plates were blocked with assay buffer containing bovine serum albumin and bovine gamma globulins (PerkinElmer) at room temperature for three hours. Antibodies were diluted in assay buffer at 20 ug/ml-0.16 ug/ml and incubated for 1 hour at 4° C. Plates were washed three times with 200 µl wash buffer (50 mM Tris pH8, 150 mM NaCl, 20 mM EDTA, 0.05% Tween). 100 µl enhancement solution (PerkinElmer) was added to each well and fluorescence counts measured using a Victor3 plate reader (PerkinElmer) at a wavelength of 615 nm. Human angiopoietin-1 and -4 was also tested for binding and showed similar reactivity.

Figure 27A:
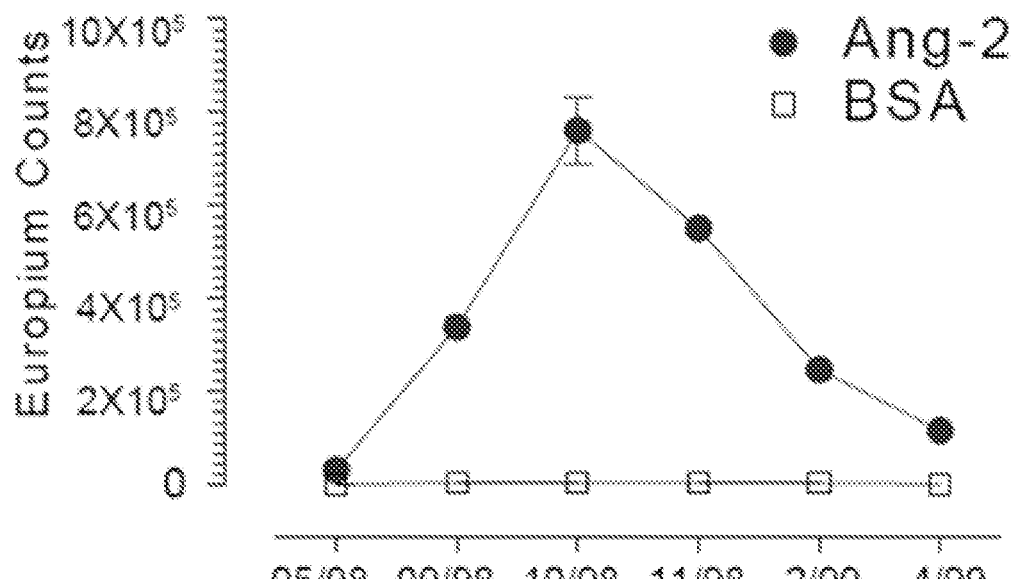
FIGS. 27A-27C|Show graphs and a gel relating to isolation of angiopoietin-specific antibodies from a lung cancer patient. (A) Angiopoietin-2 reactivity of lung cancer patient (L19) serum (diluted 1:1000) determined by ELISA. (B) FACS plot showing PBMC sample (timepoint—10/98) gated on CD19+, CD27+ IgM-B cells with CD19 on the X-axis and fluorescently-tagged angiopoietin-2 on the Y-axis. (C) Heavy, light chain, and hinge region PCR products from 10 angiopoietin-2 reactive memory B-cells isolated from patient L19. The 500 base pair marker is indicated on the left.
Figure 27B:
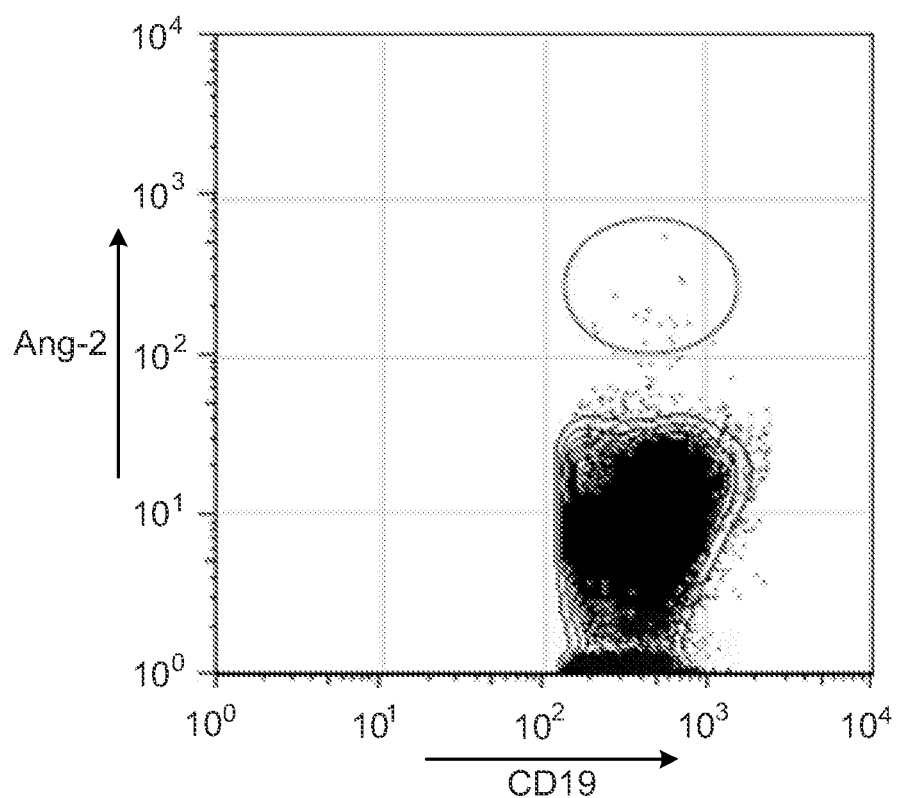
Figure 27C:
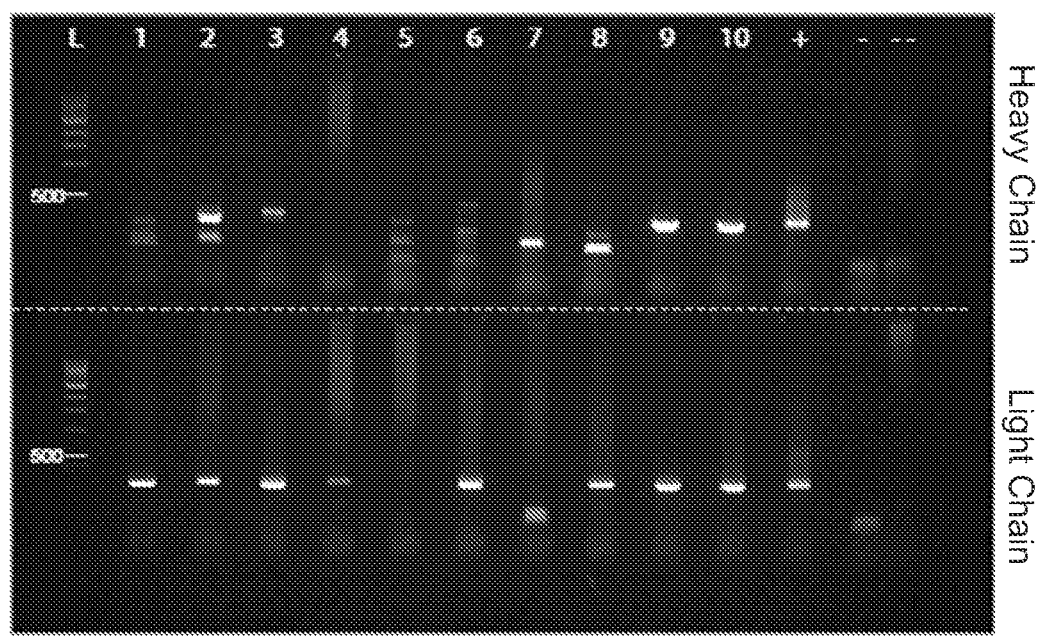

Relevant data is shown in FIGS. 27A-27C, that provide graphs and a gel relating to isolation of angiopoietin-specific antibodies from a lung cancer patient. (A) Angiopoietin-2 reactivity of lung cancer patient (L19) serum (diluted 1:1000) determined by ELISA. Dates of serum collection are shown on the X-axis. The control protein bovine serum albumin (BSA) was included as a negative control. (B) FACS plot showing PBMC sample (timepoint—10/98) gated on CD19+, CD27+ IgM-B cells with CD19 on the X-axis and fluorescently-tagged angiopoietin-2 on the Y-axis. The gate indicates approximately where the sorting cut-off was made. Ten B-cells were sorted from this sample. (C) Heavy, light chain, and hinge region PCR products from 10 angiopoietin-2 reactive memory B-cells isolated from patient L19. Heavy (top) and light (bottom) chain PCR products after two rounds of nested PCR of approximately 350 base pairs.

Example 14

Binding of Anti-Angiopoietin-2 Antibodies Against Human Recombinant Angiopoietin Family Members 96 well plates were coated overnight with 4 µg/mL recombinant angiopoietin-1, -2, and -4 (R&D Systems) in sodium bicarbonate buffer at pH9.6. Plates were subsequently blocked for 3 hours at room temperature with assay buffer (Perkin Elmer) containing bovine serum albumin (BSA) and bovine gamma-globulins. Antibodies ID 2, 3, 4, and 5 (see Table 1), diluted between 20 µg/mL-0.16 µg/mL, were incubated on plates for 1 hour at 4° C. with rotation. Plates were subsequently washed before being incubated with anti-human IgG-Europium antibody (Perkin Elmer). Fluorescent counts at 615 nm were obtained via plate reader. A negative control antibody (clone 8.18.C5) was used to determine specificity. Data was determined in duplicate.

Figure 26A:
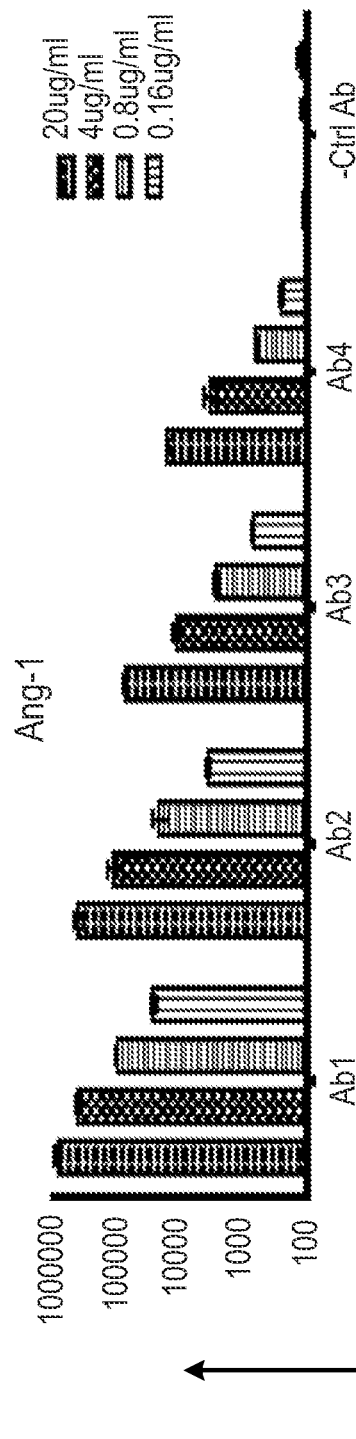
Figure 26B:
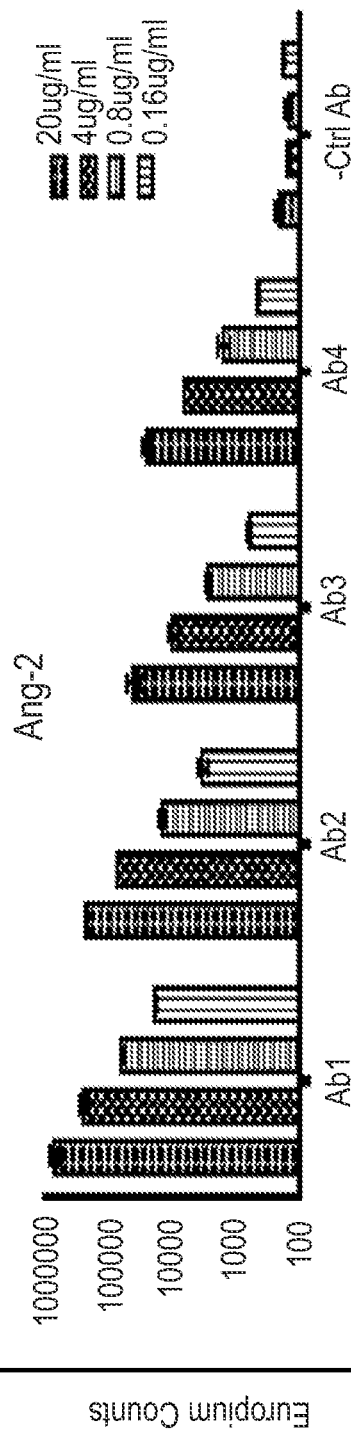
Figure 26C:
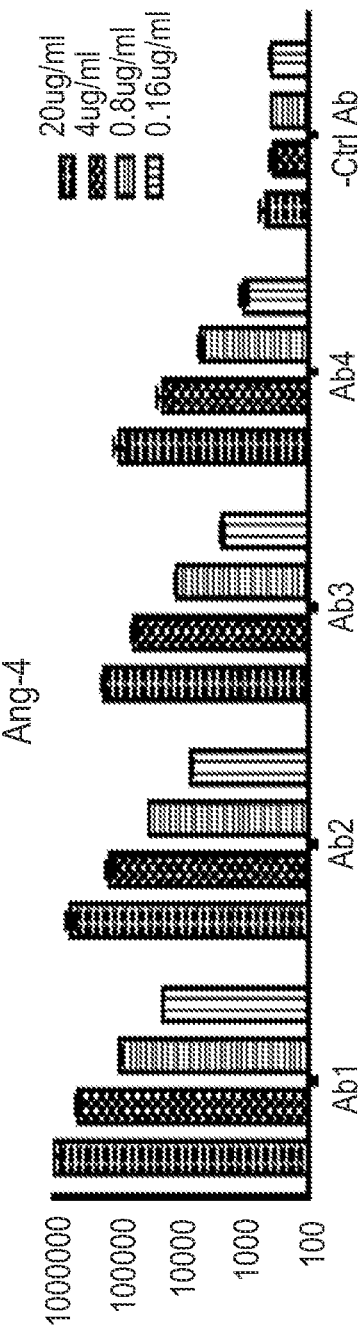

As shown in FIGS. 26A-26C, antibodies ID 2, 3, 4, and 5 (see Table 1) bind with high specificity to angiopoietin-1-2, and -4. Antibodies do not bind to Ang-like-3, a structurally-related protein (see FIG. 26D).

Figure 57:
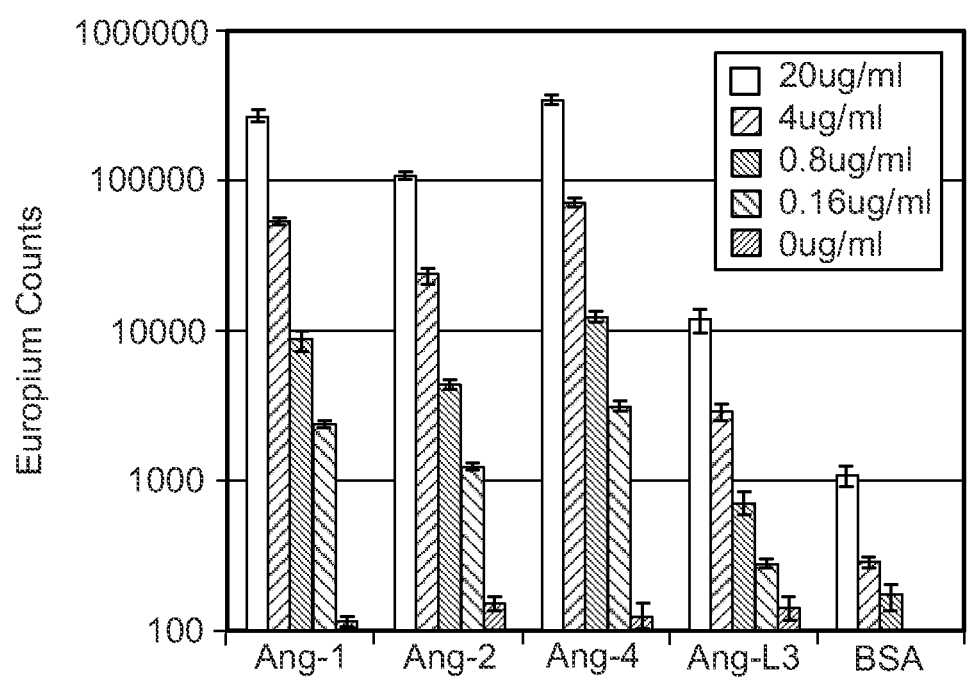
FIG. 57|Bar graphs showing binding of anti-angiopoietin 2 specific antibody anti-Ang6 Ab2 as well as a control antibody to three human angiopoietins (angiopoietin-1, 2 and 4) and ang-like-3. Recombinant angiopoietins were immobilized in an ELISA plate and binding of human recombinant antibodies was detected with europium-labeled streptavidin.

An additional anti-angiopoietin antibody, designated anti-Ang2 Ab6 (anti-MICA antibody ID-10 described in Table 1) with clinically relevant biological properties were developed using the methods herein. Binding of anti-Ang2 Ab6 to human recombinant angiopoietin family members was analyzed as described above. Briefly, ELISA plates were coated with 4 µg/ml of angiopoietins Ang-1, Ang-2, Ang4, and Ang-like-3 binding, and detection by anti-Ang2 Ab6 was tested at 20 µg/ml. 4 µg/ml, 0.8 µg/ml, and 0.16 µg/ml. Europium conjugated anti-human IgG secondary was used, with europium counts measured after 45 minutes. As shown in FIG. 57, anti-Ang2 Ab6 binds to all angiopoietins in a dose dependent manner.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating cancer in a subject, the method comprising administering a pharmaceutical composition comprising an antibody or antigen binding fragment thereof that binds to MHC class I polypeptide-related sequence A (MICA), wherein the antibody or antigen binding fragment thereof comprises a heavy chain variable region ($V_H$) and a light chain variable region ($V_L$) and wherein, (a) the $V_H$ complementarity determining region 1 (CDR1) consists of the amino acid sequence of SEQ ID NO: 153,
the VH CDR2 consists of the amino acid sequence of SEQ ID NO: 156,
the VH CDR3 consists of the amino acid sequence set forth in SEQ ID NO: 158;
the VL CDR1 consists of the amino acid sequence of SEQ ID NO:160,
the VL CDR2 consists of the amino acid sequence of SEQ ID NO: 162, and
the VL CDR3 consists of the amino acid sequence of SEQ ID NO: 164; or (b) the VH CDR 1 consists of the amino acid sequence of SEQ ID NO:208,
the VH CDR2 consists of the amino acid sequence of SEQ ID NO:210,
the VH CDR3 consists of the amino acid sequence set forth in SEQ ID NO: 212,
the VL CDR1 consists of the amino acid sequence of SEQ ID NO:215,
the VL CDR2 consists of the amino acid sequence of SEQ ID NO:217, and
the VL CDR3 consists of the amino acid sequence of SEQ ID NO:219.

2. The method of claim 1, wherein the serum of the subject has elevated levels of the soluble MICA (sMICA) prior to administration of the pharmaceutical composition.

3. The method of claim 1, wherein the cancer is melanoma, lung cancer, breast cancer, kidney cancer, ovarian cancer, prostate cancer, pancreatic cancer, gastric cancer, colon carcinoma, lymphoma or leukemia.

* * * * *

SEQUENCE LISTING

<160> NUMBER OF SEQ ID NOS: 238

<210> SEQ ID NO 1
<211> LENGTH: 384

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
caggtgcagc tacagcagtg gggcgcagga ctgttgaagc cttcggagac cctggccctc    60
acctgcgctg tctctggtgg gtccttcact gatcattact ggagttggat ccgtcaggcc   120
ccagggaagg ggctggagtg gattggagaa atcaatcata gtggagtcac caactacaac   180
ccgtccctca agagtcgact caccatatca gtagacacgt ccaagagcca gttctccctg   240
aggctgacct ctgtgaccgc cgcggacacg gctctgtact actgtgcgaa aactggcctg   300
tattatgatg acgtttgggg gacttttcgt ccacggggcg ggttcgactc ctggggccag   360
ggaaccctgg tcaccgtctc ctca                                          384

<210> SEQ ID NO 2
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gln Val Gln Leu Gln Gln Trp Gly Ala Gly Leu Leu Lys Pro Ser Glu
1               5                   10                  15

Thr Leu Ala Leu Thr Cys Ala Val Ser Gly Gly Ser Phe Thr Asp His
            20                  25                  30

Tyr Trp Ser Trp Ile Arg Gln Ala Pro Gly Lys Gly Leu Glu Trp Ile
        35                  40                  45

Gly Glu Ile Asn His Ser Gly Val Thr Asn Tyr Asn Pro Ser Leu Lys
    50                  55                  60

Ser Arg Leu Thr Ile Ser Val Asp Thr Ser Lys Ser Gln Phe Ser Leu
65                  70                  75                  80

Arg Leu Thr Ser Val Thr Ala Ala Asp Thr Ala Leu Tyr Tyr Cys Ala
                85                  90                  95

Lys Thr Gly Leu Tyr Tyr Asp Asp Val Trp Gly Thr Phe Arg Pro Arg
            100                 105                 110

Gly Gly Phe Asp Ser Trp Gly Gln Gly Thr Leu Val Thr Val Ser Ser
        115                 120                 125

<210> SEQ ID NO 3
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Val Gln Leu Gln Gln Trp Gly Ala Gly Leu Leu Lys Pro Ser Glu
1               5                   10                  15

Thr Leu Ala Leu Thr Cys Ala Val Ser
            20                  25

<210> SEQ ID NO 4
<211> LENGTH: 8
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 4

Gly Gly Ser Phe Thr Asp His Tyr
1               5

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Trp Ser Trp Ile Arg Gln Ala Pro Gly Lys Gly Leu Glu Trp Ile Gly
1               5                   10                  15

Glu

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ile Asn His Ser Gly Val Thr
1               5

<210> SEQ ID NO 7
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Asn Tyr Asn Pro Ser Leu Lys Ser Arg Leu Thr Ile Ser Val Asp Thr
1               5                   10                  15

Ser Lys Ser Gln Phe Ser Leu Arg Leu Thr Ser Val Thr Ala Ala Asp
                20                  25                  30

Thr Ala Leu Tyr Tyr Cys
        35

<210> SEQ ID NO 8
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Lys Thr Gly Leu Tyr Tyr Asp Asp Val Trp Gly Thr Phe Arg Pro
1               5                   10                  15

Arg Gly Gly Phe Asp Ser
                20

<210> SEQ ID NO 9
<211> LENGTH: 11
```

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Trp Gly Gln Gly Thr Leu Val Thr Val Ser Ser
1               5                   10

<210> SEQ ID NO 10
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
gacatcgtga tgacccagtc tccggactcc ctggctgtgt ctctgggcga gagggccacc      60
atcaactgca gtccagcca gagtatttta tatagctccg acaataagaa ttacttagct     120
tggtaccagc acaagccagg acagcctcct aagctcctct tttactgggc atctatccgg    180
gaatccgggg tccctgaccg attcagtggc ggcgggtctg ggacagattt cactctcacc    240
atcagcagtc tgcaggctga agatgtggca gtttattact gtcagcaata ttatagtcct    300
ccttgcagtt ttggccaggg gaccaagctg gagatccaa                           339

<210> SEQ ID NO 11
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Ile Leu Tyr Ser
            20                  25                  30

Ser Asp Asn Lys Asn Tyr Leu Ala Trp Tyr Gln His Lys Pro Gly Gln
        35                  40                  45

Pro Pro Lys Leu Leu Phe Tyr Trp Ala Ser Ile Arg Glu Ser Gly Val
    50                  55                  60

Pro Asp Arg Phe Ser Gly Gly Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Pro Pro Cys Ser Phe Gly Gln Gly Thr Lys Leu Glu Ile
            100                 105                 110

Gln

<210> SEQ ID NO 12
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

```
Asp Ile Val Met Thr Gln Ser Pro Asp Ser Leu Ala Val Ser Leu Gly
1               5                   10                  15

Glu Arg Ala Thr Ile Asn Cys Lys Ser Ser
            20                  25

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gln Ser Ile Leu Tyr Ser Ser Asp Asn Lys Asn Tyr
1               5                   10

<210> SEQ ID NO 14
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Leu Ala Trp Tyr Gln His Lys Pro Gly Gln Pro Pro Lys Leu Leu Phe
1               5                   10                  15

Tyr

<210> SEQ ID NO 15
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Trp Ala Ser
1

<210> SEQ ID NO 16
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Ile Arg Glu Ser Gly Val Pro Asp Arg Phe Ser Gly Gly Gly Ser Gly
1               5                   10                  15

Thr Asp Phe Thr Leu Thr Ile Ser Ser Leu Gln Ala Glu Asp Val Ala
            20                  25                  30

Val Tyr Tyr Cys
            35

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 17

Gln Gln Tyr Tyr Ser Pro Pro Cys Ser
1               5

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Phe Gly Gln Gly Thr Lys Leu Glu Ile Gln
1               5                   10

<210> SEQ ID NO 19
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
gaggtgcagc tggtggagtc tgggggaggc ttggtacagc ctggggggtc cctgagactc      60
tcctgtgcag cctctggatt cacctttagt agttatgcca tgagctgggt ccgccaggct     120
ccagggaagg gctggagtg gtctcaggt atttattgga gtggtggtag cacatactac      180
gcagactccg tgaagggccg gttcaccatc tccagagaca tatccaagaa cacgctgtat     240
ctgcaaatga acagtctgag agccgacgac acggccgtgt attactgtgc gagaggcgat     300
tactatggtt cgggggctca ctttgactac tggggccagg gaaccctggt caccgtctcc     360
tca                                                                    363

<210> SEQ ID NO 20
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Tyr Trp Ser Gly Gly Ser Thr Tyr Tyr Ala Asp Ser Val
    50                  55                  60

Lys Gly Arg Phe Thr Ile Ser Arg Asp Ile Ser Lys Asn Thr Leu Tyr
65                  70                  75                  80

Leu Gln Met Asn Ser Leu Arg Ala Asp Asp Thr Ala Val Tyr Tyr Cys
                85                  90                  95

Ala Arg Gly Asp Tyr Tyr Gly Ser Gly Ala His Phe Asp Tyr Trp Gly
            100                 105                 110

Gln Gly Thr Leu Val Thr Val Ser Ser
        115                 120

<210> SEQ ID NO 21
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Phe Thr Phe Ser Ser Tyr Ala
1               5

<210> SEQ ID NO 23
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Met Ser Trp Val Arg Gln Ala Pro Gly Lys Gly Leu Glu Trp Val Ser
1               5                   10                  15

Gly

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ile Tyr Trp Ser Gly Gly Ser Thr
1               5

<210> SEQ ID NO 25
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Tyr Tyr Ala Asp Ser Val Lys Gly Arg Phe Thr Ile Ser Arg Asp Ile
1               5                   10                  15

Ser Lys Asn Thr Leu Tyr Leu Gln Met Asn Ser Leu Arg Ala Asp Asp
            20                  25                  30

Thr Ala Val Tyr Tyr Cys

<210> SEQ ID NO 26
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 26

Ala Arg Gly Asp Tyr Tyr Gly Ser Gly Ala His Phe Asp Tyr
1               5                   10

<210> SEQ ID NO 27
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 27

Trp Gly Gln Gly Thr Leu Val Thr Val Ser Ser
1               5                   10

<210> SEQ ID NO 28
<211> LENGTH: 336
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 28
gatattgtga tgacccagac tccactctcc tcacctgtca cccttggaca gccggcctcc      60
atctcctgca ggtctagcca agcctcgta cacagtgatg aaacaccta cttgagttgg      120 cttcagcaga ggccaggcca gcctccaaga ctcctaattt atcagatttc taaccggttc     180
tctggggtcc cagacagatt cagtggcagt ggggcaggga cagatttcac actgaaaatc     240
agcagggtgg aagctgagga tgtcgggggtt tactactgca tgcaaggtac acaatttcct    300
cggacgttcg gccaagggac caaggtggaa atcaaa                               336

<210> SEQ ID NO 29
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 29

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Gln Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Gly
            85                  90                  95

Thr Gln Phe Pro Arg Thr Phe Gly Gln Gly Thr Lys Val Glu Ile Lys
        100                 105                 110

<210> SEQ ID NO 30
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Asp Ile Val Met Thr Gln Thr Pro Leu Ser Ser Pro Val Thr Leu Gly
1               5                   10                  15

Gln Pro Ala Ser Ile Ser Cys Arg Ser Ser
            20                  25

<210> SEQ ID NO 31
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gln Ser Leu Val His Ser Asp Gly Asn Thr Tyr
1               5                   10

<210> SEQ ID NO 32
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Leu Ser Trp Leu Gln Gln Arg Pro Gly Gln Pro Pro Arg Leu Leu Ile
1               5                   10                  15

Tyr

<210> SEQ ID NO 33
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gln Ile Ser
1

<210> SEQ ID NO 34
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Asn Arg Phe Ser Gly Val Pro Asp Arg Phe Ser Gly Ser Gly Ala Gly

```
1               5                   10                  15
Thr Asp Phe Thr Leu Lys Ile Ser Arg Val Glu Ala Glu Asp Val Gly
            20                  25                  30

Val Tyr Tyr Cys
        35

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Met Gln Gly Thr Gln Phe Pro Arg Thr
1               5

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Phe Gly Gln Gly Thr Lys Val Glu Ile Lys
1               5                   10

<210> SEQ ID NO 37
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37
gaggtgcagc tggtggagtc cggggggaggc ttagttcagc ctgggggatc cctgagactc      60
tcctgtgcag cctcagggtt caccttagt aataactgga tgcactgggt ccgccaggct      120
ccagggaagg gctggagtg atctcagag attagaagtg atgggaattt cacaaggtac       180
gcggactcca tgaagggccg attcaccatc tccagagaca cgccaagag cacactgtat       240 ttgcaaatga acagtctgag agtcgaggac acgggtctgt attactgtgc aagagactac      300
ccctatagca ttgactactg gggccaggga accctggtca ccgtctcctc a              351

<210> SEQ ID NO 38
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Asn
            20                  25                  30

Trp Met His Trp Val Arg Gln Ala Pro Gly Lys Gly Leu Glu Trp Ile
        35                  40                  45
```

```
Ser Glu Ile Arg Ser Asp Gly Asn Phe Thr Arg Tyr Ala Asp Ser Met
    50                  55                  60

Lys Gly Arg Phe Thr Ile Ser Arg Asp Asn Ala Lys Ser Thr Leu Tyr
 65                  70                  75                  80

Leu Gln Met Asn Ser Leu Arg Val Glu Asp Thr Gly Leu Tyr Tyr Cys
                 85                  90                  95

Ala Arg Asp Tyr Pro Tyr Ser Ile Asp Tyr Trp Gly Gln Gly Thr Leu
                100                 105                 110

Val Thr Val Ser Ser
        115

<210> SEQ ID NO 39
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Glu Val Gln Leu Val Glu Ser Gly Gly Gly Leu Val Gln Pro Gly Gly
1               5                  10                  15

Ser Leu Arg Leu Ser Cys Ala Ala Ser
            20                  25

<210> SEQ ID NO 40
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Phe Thr Phe Ser Asn Asn Trp
1               5

<210> SEQ ID NO 41
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Met His Trp Val Arg Gln Ala Pro Gly Lys Gly Leu Glu Trp Ile Ser
1               5                  10                  15

Glu

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ile Arg Ser Asp Gly Asn Phe Thr
1               5

<210> SEQ ID NO 43
<211> LENGTH: 38
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Arg Tyr Ala Asp Ser Met Lys Gly Arg Phe Thr Ile Ser Arg Asp Asn
1               5                   10                  15
Ala Lys Ser Thr Leu Tyr Leu Gln Met Asn Ser Leu Arg Val Glu Asp
            20                  25                  30
Thr Gly Leu Tyr Tyr Cys
        35

<210> SEQ ID NO 44
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ala Arg Asp Tyr Pro Tyr Ser Ile Asp Tyr
1               5                   10

<210> SEQ ID NO 45
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Trp Gly Gln Gly Thr Leu Val Thr Val Ser Ser
1               5                   10

<210> SEQ ID NO 46
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
gatattgtga tgacccagac tccactctcc tcacctgtca cccttggaca gccggcctcc      60
atctcctgca catctagtca aagcctcgta cacagtaatg gaaacaccta cttgagttgg     120
cttcagcaga ggccaggcca gccccccaaga ctcctaattt atgagatttc taagcgggtc     180
tctggggtcc cagacagatt cagtggcagt ggggcaggga cagatttcac actgaaaatc     240
agcagggtgg aagctgagga tgtcggggtt tattactgca tgcaaggtaa acaacttcgg     300
acttttggcc agggaccaa gctggagatc aaa                                   333

<210> SEQ ID NO 47
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47
```

```
Asp Ile Val Met Thr Gln Thr Pro Leu Ser Ser Pro Val Thr Leu Gly
1               5                   10                  15

Gln Pro Ala Ser Ile Ser Cys Thr Ser Ser Gln Ser Leu Val His Ser
            20                  25                  30

Asn Gly Asn Thr Tyr Leu Ser Trp Leu Gln Gln Arg Pro Gly Gln Pro
        35                  40                  45

Pro Arg Leu Leu Ile Tyr Glu Ile Ser Lys Arg Val Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Lys Gln Leu Arg Thr Phe Gly Gln Gly Thr Lys Leu Glu Ile Lys
            100                 105                 110

<210> SEQ ID NO 48
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Asp Ile Val Met Thr Gln Thr Pro Leu Ser Ser Pro Val Thr Leu Gly
1               5                   10                  15

Gln Pro Ala Ser Ile Ser Cys Thr Ser Ser
            20                  25

<210> SEQ ID NO 49
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gln Ser Leu Val His Ser Asn Gly Asn Thr Tyr
1               5                   10

<210> SEQ ID NO 50
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Leu Ser Trp Leu Gln Gln Arg Pro Gly Gln Pro Pro Arg Leu Leu Ile
1               5                   10                  15

Tyr

<210> SEQ ID NO 51
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51
```

Glu Ile Ser
1

<210> SEQ ID NO 52
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Lys Arg Val Ser Gly Val Pro Asp Arg Phe Ser Gly Ser Gly Ala Gly
1               5                   10                  15

Thr Asp Phe Thr Leu Lys Ile Ser Arg Val Glu Ala Glu Asp Val Gly
            20                  25                  30

Val Tyr Tyr Cys
        35

<210> SEQ ID NO 53
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Met Gln Gly Lys Gln Leu Arg Thr
1               5

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Phe Gly Gln Gly Thr Lys Leu Glu Ile Lys
1               5                   10

<210> SEQ ID NO 55
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55
gaggtgcagc tggtggagtc tgggggaggc ttggtacagc ctggggggctc cgtgagactg      60 tcttgtgcgg cctcaggctt cattcttagc aactttgcca tgagttgggt ccgccaggct     120
ccagggaagg ggctggactg ggtctcaggt aattttggtg gtcgtgaaaa tacatattac     180
gcagactccg tgaagggccg gttcaccatc tccagagaca gttccaagag cacactgtat     240
ctgcaaatga acaatttgag agccgaggac acggccgtat attactgtgc gcgaggcgat     300
taccatggtt cggggggctca ctttgactac tggggccagg gaatactggt caccgtctcc     360
tca                                                                    363

<210> SEQ ID NO 56
<211> LENGTH: 121

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Glu Val Gln Leu Val Glu Ser Gly Gly Gly Leu Val Gln Pro Gly Gly
1               5                   10                  15

Ser Val Arg Leu Ser Cys Ala Ala Ser Gly Phe Ile Leu Ser Asn Phe
            20                  25                  30

Ala Met Ser Trp Val Arg Gln Ala Pro Gly Lys Gly Leu Asp Trp Val
        35                  40                  45

Ser Gly Asn Phe Gly Gly Arg Glu Asn Thr Tyr Tyr Ala Asp Ser Val
    50                  55                  60

Lys Gly Arg Phe Thr Ile Ser Arg Asp Ser Ser Lys Ser Thr Leu Tyr
65                  70                  75                  80

Leu Gln Met Asn Asn Leu Arg Ala Glu Asp Thr Ala Val Tyr Tyr Cys
                85                  90                  95

Ala Arg Gly Asp Tyr His Gly Ser Gly Ala His Phe Asp Tyr Trp Gly
            100                 105                 110

Gln Gly Ile Leu Val Thr Val Ser Ser
        115                 120

<210> SEQ ID NO 57
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Glu Val Gln Leu Val Glu Ser Gly Gly Gly Leu Val Gln Pro Gly Gly
1               5                   10                  15

Ser Val Arg Leu Ser Cys Ala Ala Ser
            20                  25

<210> SEQ ID NO 58
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Phe Ile Leu Ser Asn Phe Ala
1               5

<210> SEQ ID NO 59
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Met Ser Trp Val Arg Gln Ala Pro Gly Lys Gly Leu Asp Trp Val Ser
1               5                   10                  15

Gly
```

<210> SEQ ID NO 60
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Asn Phe Gly Gly Arg Glu Asn Thr
1               5

<210> SEQ ID NO 61
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Tyr Tyr Ala Asp Ser Val Lys Gly Arg Phe Thr Ile Ser Arg Asp Ser
1               5                   10                  15

Ser Lys Ser Thr Leu Tyr Leu Gln Met Asn Asn Leu Arg Ala Glu Asp
            20                  25                  30

Thr Ala Val Tyr Tyr Cys
        35

<210> SEQ ID NO 62
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Ala Arg Gly Asp Tyr His Gly Ser Gly Ala His Phe Asp Tyr
1               5                   10

<210> SEQ ID NO 63
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Trp Gly Gln Gly Ile Leu Val Thr Val Ser Ser
1               5                   10

<210> SEQ ID NO 64
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64
gatattgtga tgacccagag tccactctcc tcacctgtca tccttggaca gccggcctcc      60
atctcctgca ggtctagtca aagcctccta cacagtgatg gaaacaccta cttgagttgg     120
cttcaccaga ggccaggcca gcctcctaga ctcctaattt atcagatttc taaccggttc     180

```
tctggggtcc cagacagatt cagtggcagt gggacaggga cagatttcac actgaaaatc    240
agcagggtgg aagctgagga tgccgggatt tattactgca tgcaaggtac agaatttcct    300
cggacgttcg gccaagggac caaggtggaa atcaaa                              336
```

<210> SEQ ID NO 65
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

```
Asp Ile Val Met Thr Gln Ser Pro Leu Ser Ser Pro Val Ile Leu Gly
1               5                   10                  15

Gln Pro Ala Ser Ile Ser Cys Arg Ser Ser Gln Ser Leu Leu His Ser
            20                  25                  30

Asp Gly Asn Thr Tyr Leu Ser Trp Leu His Gln Arg Pro Gly Gln Pro
        35                  40                  45

Pro Arg Leu Leu Ile Tyr Gln Ile Ser Asn Arg Phe Ser Gly Val Pro
    50                  55                  60

Asp Arg Phe Ser Gly Ser Gly Thr Gly Thr Asp Phe Thr Leu Lys Ile
65                  70                  75                  80

Ser Arg Val Glu Ala Glu Asp Ala Gly Ile Tyr Tyr Cys Met Gln Gly
                85                  90                  95

Thr Glu Phe Pro Arg Thr Phe Gly Gln Gly Thr Lys Val Glu Ile Lys
            100                 105                 110
```

<210> SEQ ID NO 66
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

```
Asp Ile Val Met Thr Gln Ser Pro Leu Ser Ser Pro Val Ile Leu Gly
1               5                   10                  15

Gln Pro Ala Ser Ile Ser Cys Arg Ser Ser
            20                  25
```

<210> SEQ ID NO 67
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

```
Gln Ser Leu Leu His Ser Asp Gly Asn Thr Tyr
1               5                   10
```

<210> SEQ ID NO 68
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

```
Leu Ser Trp Leu His Gln Arg Pro Gly Gln Pro Pro Arg Leu Leu Ile
1               5                   10                  15

Tyr

<210> SEQ ID NO 69
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gln Ile Ser
1

<210> SEQ ID NO 70
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Asn Arg Phe Ser Gly Val Pro Asp Arg Phe Ser Gly Ser Gly Thr Gly
1               5                   10                  15

Thr Asp Phe Thr Leu Lys Ile Ser Arg Val Glu Ala Glu Asp Ala Gly
            20                  25                  30

Ile Tyr Tyr Cys
        35

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Met Gln Gly Thr Glu Phe Pro Arg Thr
1               5

<210> SEQ ID NO 72
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Phe Gly Gln Gly Thr Lys Val Glu Ile Lys
1               5                   10

<210> SEQ ID NO 73
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73
```

```
gaggtgcagc tggtggagtc tgggggaggc ttgatacagc ctggggggtc cctgagactc    60
tcctgtgcaa cctctggatt cacctttaga acttcttcca tgagttgggt ccgtcgggct   120
ccagggaagg ggctggaatg ggtctcagct attggtgctg aaagtcatga cacgcactac   180
acagactccg cggagggccg gttcaccatc tccaaagact attcaaagaa cacagtatat   240
ctgcagatga acggcctgag agtcgacgac acggccatat attattgtgc ccatcactat   300
tactatggct cgcggcagaa acccaaagat tggggagatg cttttgatat gtggggccag   360
gggacaatgg tctccgtctc ttca                                          384
```

<210> SEQ ID NO 74
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

```
Glu Val Gln Leu Val Glu Ser Gly Gly Gly Leu Ile Gln Pro Gly Gly
1               5                   10                  15

Ser Leu Arg Leu Ser Cys Ala Thr Ser Gly Phe Thr Phe Arg Thr Ser
            20                  25                  30

Ser Met Ser Trp Val Arg Arg Ala Pro Gly Lys Gly Leu Glu Trp Val
        35                  40                  45

Ser Ala Ile Gly Ala Glu Ser His Asp Thr His Tyr Thr Asp Ser Ala
    50                  55                  60

Glu Gly Arg Phe Thr Ile Ser Lys Asp Tyr Ser Lys Asn Thr Val Tyr
65                  70                  75                  80

Leu Gln Met Asn Gly Leu Arg Val Asp Asp Thr Ala Ile Tyr Tyr Cys
                85                  90                  95

Ala His His Tyr Tyr Tyr Gly Ser Arg Gln Lys Pro Lys Asp Trp Gly
            100                 105                 110

Asp Ala Phe Asp Met Trp Gly Gln Gly Thr Met Val Ser Val Ser Ser
        115                 120                 125
```

<210> SEQ ID NO 75
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

```
Glu Val Gln Leu Val Glu Ser Gly Gly Gly Leu Ile Gln Pro Gly Gly
1               5                   10                  15

Ser Leu Arg Leu Ser Cys Ala Thr Ser
            20                  25
```

<210> SEQ ID NO 76
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

```
Gly Phe Thr Phe Arg Thr Ser Ser
1               5
```

<210> SEQ ID NO 77
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Met Ser Trp Val Arg Arg Ala Pro Gly Lys Gly Leu Glu Trp Val Ser
1               5                   10                  15

Ala

<210> SEQ ID NO 78
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Ile Gly Ala Glu Ser His Asp Thr
1               5

<210> SEQ ID NO 79
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

His Tyr Thr Asp Ser Ala Glu Gly Arg Phe Thr Ile Ser Lys Asp Tyr
1               5                   10                  15

Ser Lys Asn Thr Val Tyr Leu Gln Met Asn Gly Leu Arg Val Asp Asp
            20                  25                  30

Thr Ala Ile Tyr Tyr Cys
        35

<210> SEQ ID NO 80
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ala His His Tyr Tyr Tyr Gly Ser Arg Gln Lys Pro Lys Asp Trp Gly
1               5                   10                  15

Asp Ala Phe Asp Met
            20

<210> SEQ ID NO 81
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Trp Gly Gln Gly Thr Met Val Ser Val Ser Ser
1               5                   10

<210> SEQ ID NO 82
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 82
gacatccaga tgacccagtc tccatcttct gtgtctgcat ctgtaggaga cagagtcacc    60
atcacttgtc gggcgagtca ggatattagc acctggttaa cctggtatca gcagagagca   120
gggaaggccc ctaacctcct gatctatggt gcatccactt tggaagatgg ggtcccatcc   180
aggttcagcg gcagtggatc cgggacagat ttcactctca ctatcgacag cctgcagcct   240
gacgattttg caacttacta ttgtcaacag tctcacagtt tccccctacac ttttggccag   300 gggacccagc tggggatctc a                                              321

<210> SEQ ID NO 83
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ser Thr Trp
            20                  25                  30

Leu Thr Trp Tyr Gln Gln Arg Ala Gly Lys Ala Pro Asn Leu Leu Ile
        35                  40                  45

Tyr Gly Ala Ser Thr Leu Glu Asp Gly Val Pro Ser Arg Phe Ser Gly
    50                  55                  60

Ser Gly Ser Gly Thr Asp Phe Thr Leu Thr Ile Asp Ser Leu Gln Pro
65                  70                  75                  80

Asp Asp Phe Ala Thr Tyr Tyr Cys Gln Gln Ser His Ser Phe Pro Tyr
                85                  90                  95

Thr Phe Gly Gln Gly Thr Gln Leu Gly Ile Ser
            100                 105

<210> SEQ ID NO 84
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Asp Ile Gln Met Thr Gln Ser Pro Ser Ser Val Ser Ala Ser Val Gly
1               5                   10                  15

Asp Arg Val Thr Ile Thr Cys Arg Ala Ser
            20                  25

<210> SEQ ID NO 85
<211> LENGTH: 6
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 85

Gln Asp Ile Ser Thr Trp
1               5

<210> SEQ ID NO 86
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Leu Thr Trp Tyr Gln Gln Arg Ala Gly Lys Ala Pro Asn Leu Leu Ile
1               5                   10                  15

Tyr

<210> SEQ ID NO 87
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Gly Ala Ser
1

<210> SEQ ID NO 88
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Thr Leu Glu Asp Gly Val Pro Ser Arg Phe Ser Gly Ser Gly Ser Gly
1               5                   10                  15

Thr Asp Phe Thr Leu Thr Ile Asp Ser Leu Gln Pro Asp Asp Phe Ala
            20                  25                  30

Thr Tyr Tyr Cys
        35

<210> SEQ ID NO 89
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Gln Gln Ser His Ser Phe Pro Tyr Thr
1               5

<210> SEQ ID NO 90
<211> LENGTH: 10
<212> TYPE: PRT
<213> ORGANISM: Artificial Sequence
```

<220> FEATURE:
<223> OTHER INFORMATION: Description of Artificial Sequence: Synthetic
      peptide

<400> SEQUENCE: 90

Phe Gly Gln Gly Thr Gln Leu Gly Ile Ser
1               5                   10

<210> SEQ ID NO 91
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
taatacgact cactataggt tcggggaagt agtccttgac cagg                          44

<210> SEQ ID NO 92
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
taatacgact cactataggg atagaagtta ttcagcaggc acac                          44

<210> SEQ ID NO 93
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
taatacgact cactataggc gtcaggctca grtagctgct ggccgc                        46

<210> SEQ ID NO 94
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
aatacgactc actataggtt cggggaagta gtccttgacc agg                           43

<210> SEQ ID NO 95
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
taatacgact cactataggg atagaagtta ttcagcaggc acac                          44

<210> SEQ ID NO 96
<211> LENGTH: 46
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 96
taatacgact cactataggc gtcaggctca grtagctgct ggccgc              46

<210> SEQ ID NO 97
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
tcaccatgga ctgsacctgg a                                         21

<210> SEQ ID NO 98
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
ccatggacac actttgytcc ac                                        22

<210> SEQ ID NO 99
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
tcaccatgga gtttgggctg agc                                       23

<210> SEQ ID NO 100
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
agaacatgaa acayctgtgg ttctt                                     25

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
atggggtcaa ccgccatcct                                           20

<210> SEQ ID NO 102
<211> LENGTH: 23
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 102
acaatgtctg tctccttcct cat                                            23

<210> SEQ ID NO 103
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
gctcagctcc tggggctcct g                                              21

<210> SEQ ID NO 104
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
ctggggctgc taatgctctg g                                              21

<210> SEQ ID NO 105
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
ttcctcctgc tactctggct c                                              21

<210> SEQ ID NO 106
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
cagacccagg tcttcatttc t                                              21

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
cctctcctcc tcaccctcct                                                20

<210> SEQ ID NO 108
<211> LENGTH: 18
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 108
ctcctcactc agggcaca                                                 18

<210> SEQ ID NO 109
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
atggcctgga ycsctctcc                                                19

<210> SEQ ID NO 110
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
gccaggggga agacsgatg                                                19

<210> SEQ ID NO 111
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
tttcaactgc tcatcagatg gcgg                                          24

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
agctcctcag aggagggygg                                               20

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
caggtscagc tggtrcagtc                                               20

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
cagrtcacct tgaaggagtc					20

<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
saggtgcagc tggtggagtc					20

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
caggtgcagc tgcaggagtc					20

<210> SEQ ID NO 117
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
gargtgcagc tggtgcagtc					20

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
caggtacagc tgcagcagtc					20

<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
cgmcatccrg wtgacccagt					20

<210> SEQ ID NO 120
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 120
cgatrttgtg atgacycag                                          19

<210> SEQ ID NO 121
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
cgaaatwgtg wtgacrcagt ct                                      22

<210> SEQ ID NO 122
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
cgacatcgtg atgacccagt                                         20

<210> SEQ ID NO 123
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
ccagtctgtg ctgactcagc                                         20

<210> SEQ ID NO 124
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
ccagtctgcc ctgactcagc                                         20

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
ctcctatgag ctgacwcagc                                         20

<210> SEQ ID NO 126
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
```
gacsgatggg cccttggtgg a                                              21

<210> SEQ ID NO 127
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
aagatgaaga cagatggtgc                                                20

<210> SEQ ID NO 128
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
gggaacagag tgaccg                                                    16

<210> SEQ ID NO 129
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
tcactatgga ctggatttgg a                                              21

<210> SEQ ID NO 130
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
ccatggacay actttgytcc ac                                             22

<210> SEQ ID NO 131
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
gtaggagaca tgcaaatagg gcc                                            23

<210> SEQ ID NO 132
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
aacaaagcta tgacatatag atc                                    23

<210> SEQ ID NO 133
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
atggagttgg ggctgagctg ggtt                                   24

<210> SEQ ID NO 134
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
agttgttaaa tgtttatcgc aga                                    23

<210> SEQ ID NO 135
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
aggtaattca tggagaaata gaa                                    23

<210> SEQ ID NO 136
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
agaacatgaa gcayctgtgg ttctt                                  25

<210> SEQ ID NO 137
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
atggactgga cctggagcat c                                      21

<210> SEQ ID NO 138
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
cctctgctga tgaaaaccag ccc                                    23

<210> SEQ ID NO 139
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
caggtycagc tkgtgcagtc                                              20

<210> SEQ ID NO 140
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
caratgcagc tggtgcagtc                                              20

<210> SEQ ID NO 141
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
cagrtcacct tgarggagtc tggt                                         24

<210> SEQ ID NO 142
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
gargtgcagc tgktggagtc                                              20

<210> SEQ ID NO 143
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
gaggtacaac tggtggagtc                                              20

<210> SEQ ID NO 144
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
gaggatcagc tggtggagtc                                              20

<210> SEQ ID NO 145
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
caggtgcagc tacagcagtg                                              20

<210> SEQ ID NO 146
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
cagctgcagc tgcaggagtc                                              20

<210> SEQ ID NO 147
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
caggtgcagc tggtgcaatc                                              20

<210> SEQ ID NO 148
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 148
caggtgcagc tgcaggagtc gggcccagga ctggtggagc cttcgggac cctgtccctc    60 acctgcactg tgtctggtgg ctccatcagc aggagtaact ggtggagttg ggtccgccag  120
cccccagggg aggggctgga atggattgga gaaatccatc acattgggag gtccagctac  180
aatccgtccc tcaagagtcg agtcaccatg tctgtagaca gtcccagaa ccagttctcc   240 ctgaggctga cctctgtgac cgccgcggac acggccgtgt attactgtgc gaaaaatggc  300
tactacgcta tggacgtctg gggccaaggg accacggtca ccgtctcctc g           351

<210> SEQ ID NO 149
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Gln Val Gln Leu Gln Glu Ser Gly Pro Gly Leu Val Glu Pro Ser Gly
1               5                   10                  15

Thr Leu Ser Leu Thr Cys Thr Val Ser Gly Gly Ser Ile Ser Arg Ser
            20                  25                  30

Asn Trp Trp Ser Trp Val Arg Gln Pro Pro Gly Glu Gly Leu Glu Trp
            35                  40                  45

Ile Gly Glu Ile His His Ile Gly Arg Ser Ser Tyr Asn Pro Ser Leu
 50                  55                  60

Lys Ser Arg Val Thr Met Ser Val Asp Lys Ser Gln Asn Gln Phe Ser
 65                  70                  75                  80

Leu Arg Leu Thr Ser Val Thr Ala Ala Asp Thr Ala Val Tyr Tyr Cys
                 85                  90                  95

Ala Lys Asn Gly Tyr Tyr Ala Met Asp Val Trp Gly Gln Gly Thr Thr
                100                 105                 110

Val Thr Val Ser Ser
            115

<210> SEQ ID NO 150
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 150
gaaattgtgt tgacgcagtc tccaggcacc ctgtctttgt ctccagggga aagagccacc      60
ctctcctgca gggccagtca gagtgttagc agcgacttcc tagcctggta ccagcagaaa     120
cctggccagg ctcccaggct cctcatctac gctacatcct tcagggccac tggcatctca     180
gacaggttca gtggcagtgg gtctgggaca gacttctctc tcaccatcaa cagactggaa     240
cctgaagatt ttgcagtgta ttactgtcag cactatcgta gttcaccttcc gtggtacact     300 tttgcccagg ggaccaagct ggacatgaga cgtacggtgg ctgcaccatc tgtc            354

<210> SEQ ID NO 151
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Asp
             20                  25                  30

Phe Leu Ala Trp Tyr Gln Gln Lys Pro Gly Gln Ala Pro Arg Leu Leu
         35                  40                  45

Ile Tyr Ala Thr Ser Phe Arg Ala Thr Gly Ile Ser Asp Arg Phe Ser
 50                  55                  60

Gly Ser Gly Ser Gly Thr Asp Phe Ser Leu Thr Ile Asn Arg Leu Glu
 65                  70                  75                  80

Pro Glu Asp Phe Ala Val Tyr Tyr Cys Gln His Tyr Arg Ser Ser Pro
                 85                  90                  95

Pro Trp Tyr Thr Phe Ala Gln Gly Thr Lys Leu Asp Met Arg Arg Thr
                100                 105                 110

Val Ala Ala Pro Ser Val
            115

<210> SEQ ID NO 152
<211> LENGTH: 25

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Gln Val Gln Leu Gln Glu Ser Gly Pro Gly Leu Val Glu Pro Ser Gly
1               5                   10                  15
Thr Leu Ser Leu Thr Cys Thr Val Ser
            20                  25

<210> SEQ ID NO 153
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Gly Gly Ser Ile Ser Arg Ser Asn Trp
1               5

<210> SEQ ID NO 154
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Trp Ser Trp Val Arg Gln Pro Pro Gly Glu Gly Leu Glu Trp Ile Gly
1               5                   10                  15
Glu

<210> SEQ ID NO 155
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Gly Gln Gly Thr Thr Val Thr Val Ser Ser
1               5                   10

<210> SEQ ID NO 156
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Ile His His Ile Gly Arg Ser
1               5

<210> SEQ ID NO 157
<211> LENGTH: 37
<212> TYPE: PRT
<213> ORGANISM: Artificial Sequence
<220> FEATURE:
<223> OTHER INFORMATION: Description of Artificial Sequence: Synthetic
```

```
                          polypeptide

<400> SEQUENCE: 157

Ser Tyr Asn Pro Ser Leu Lys Ser Arg Val Thr Met Ser Val Asp Lys
1               5                   10                  15

Ser Gln Asn Gln Phe Ser Leu Arg Leu Thr Ser Val Thr Ala Ala Asp
            20                  25                  30

Thr Ala Val Tyr Tyr
        35

<210> SEQ ID NO 158
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Cys Ala Lys Asn Gly Tyr Tyr Ala Met Asp Val Trp
1               5                   10

<210> SEQ ID NO 159
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Glu Ile Val Leu Thr Gln Ser Pro Gly Thr Leu Ser Leu Ser Pro Gly
1               5                   10                  15

Glu Arg Ala Thr Leu Ser Cys Arg Ala Ser
            20                  25

<210> SEQ ID NO 160
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Gln Ser Val Ser Ser Asp Phe
1               5

<210> SEQ ID NO 161
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Leu Ala Trp Tyr Gln Gln Lys Pro Gly Gln Ala Pro Arg Leu Leu Ile
1               5                   10                  15

Tyr

<210> SEQ ID NO 162
<211> LENGTH: 3
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 162

Ala Thr Ser
1

<210> SEQ ID NO 163
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Phe Arg Ala Thr Gly Ile Ser Asp Arg Phe Ser Gly Ser Gly Ser Gly
1               5                   10                  15

Thr Asp Phe Ser Leu Thr Ile Asn Arg Leu Glu Pro Glu Asp Phe Ala
            20                  25                  30

Val Tyr Tyr
        35

<210> SEQ ID NO 164
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Cys Gln His Tyr Arg Ser Ser Pro Pro Trp Tyr Thr Phe
1               5                   10

<210> SEQ ID NO 165
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Ala Gln Gly Thr Lys Leu Asp Met Arg Arg Thr Val Ala Ala Pro Ser
1               5                   10                  15

Val

<210> SEQ ID NO 166
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Asn Ser Asn Pro Ser Leu Lys Ser Arg Val Ile Ile Ser Val Asp Lys
1               5                   10                  15

Ser Lys Asn His Phe Ser Leu Thr Leu Asn Ser Val Thr Ala Ala Asp
            20                  25                  30

Thr Ala Val Tyr Tyr
        35
```

<210> SEQ ID NO 167
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 167

```
caggtgcagc tgcaggagtc gggcccagga ctggtgaagc cttcggggac cctgtccctc      60
acctgcgctg tctctggtgc ctccattacc aatggtgcct ggtggagttg ggtccgccag     120
cccccaggga aggggctgga gtggattgga gaaatctatc ttaatgggaa caccaactcc     180
aacccgtccc tgaagagtcg agtcatcata tcagtggaca gtccaagaa  ccacttctcg     240 ctgaccctga actctgtgac cgccgcggac acggccgtgt attactgtgc gaagaacgct     300
gcctacaacc ttgagttctg gggccaggga gccctggtca ccgtctcctc a              351
```

<210> SEQ ID NO 168
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Gln Val Gln Leu Gln Glu Ser Gly Pro Gly Leu Val Lys Pro Ser Gly
1               5                   10                  15

Thr Leu Ser Leu Thr Cys Ala Val Ser Gly Ala Ser Ile Thr Asn Gly
            20                  25                  30

Ala Trp Trp Ser Trp Val Arg Gln Pro Pro Gly Lys Gly Leu Glu Trp
        35                  40                  45

Ile Gly Glu Ile Tyr Leu Asn Gly Asn Thr Asn Ser Asn Pro Ser Leu
    50                  55                  60

Lys Ser Arg Val Ile Ile Ser Val Asp Lys Ser Lys Asn His Phe Ser
65                  70                  75                  80

Leu Thr Leu Asn Ser Val Thr Ala Ala Asp Thr Ala Val Tyr Tyr Cys
                85                  90                  95

Ala Lys Asn Ala Ala Tyr Asn Leu Glu Phe Trp Gly Gln Gly Ala Leu
            100                 105                 110

Val Thr Val Ser Ser
        115

<210> SEQ ID NO 169
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 169

```
gaaattgtgt tgacgcagtc tccaggcacc ctgtctttgt ctccagggga aagagccacc      60
ctctcctgca gggccagtca gactgttagc agccccta cg tagcctggta ccagcagaaa    120
cgtggccagg ctcccaggct cctcatctat ggtgcatcca ccagggccac cggcatccca    180
gacaggttca gtggcagtgg gtctgggaca gacttcactc tcaccatcag cagactggag    240
cctgaagatt ttgcagtgta ttactgtcag cagtatgata gatcatacta ttacactttt    300
```
ggccagggga ccaagctgga gatcaaa                    327

<210> SEQ ID NO 170
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Thr Val Ser Ser Pro
            20                  25                  30

Tyr Val Ala Trp Tyr Gln Gln Lys Arg Gly Gln Ala Pro Arg Leu Leu
        35                  40                  45

Ile Tyr Gly Ala Ser Thr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Asp Arg Ser Tyr
                85                  90                  95

Tyr Tyr Thr Phe Gly Gln Gly Thr Lys Leu Glu Ile Lys
            100                 105

<210> SEQ ID NO 171
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Gln Val Gln Leu Gln Glu Ser Gly Pro Gly Leu Val Lys Pro Ser Gly
1               5                   10                  15

Thr Leu Ser Leu Thr Cys Ala Val Ser
            20                  25

<210> SEQ ID NO 172
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Gly Ala Ser Ile Thr Asn Gly Ala Trp
1               5

<210> SEQ ID NO 173
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Trp Ser Trp Val Arg Gln Pro Pro Gly Lys Gly Leu Glu Trp Ile Gly
1               5                   10                  15

Glu

```
<210> SEQ ID NO 174
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Ile Tyr Leu Asn Gly Asn Thr
1               5

<210> SEQ ID NO 175
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Gly Gln Gly Thr Leu Val Thr Val Ser Ser Ala Ser Thr Lys
1               5                   10

<210> SEQ ID NO 176
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Cys Ala Lys Asn Ala Ala Tyr Asn Leu Glu Phe Trp
1               5                   10

<210> SEQ ID NO 177
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Gly Gln Gly Ala Leu Val Thr Val Ser Ser
1               5                   10

<210> SEQ ID NO 178
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Glu Ile Val Leu Thr Gln Ser Pro Gly Thr Leu Ser Leu Ser Pro Gly
1               5                   10                  15

Glu Arg Ala Thr Leu Ser Cys Arg Ala Ser
            20                  25

<210> SEQ ID NO 179
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 179

Gln Thr Val Ser Ser Pro Tyr
1               5

<210> SEQ ID NO 180
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Val Ala Trp Tyr Gln Gln Lys Arg Gly Gln Ala Pro Arg Leu Leu Ile
1               5                   10                  15

Tyr

<210> SEQ ID NO 181
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Gly Ala Ser
1

<210> SEQ ID NO 182
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

Thr Arg Ala Thr Gly Ile Pro Asp Arg Phe Ser Gly Ser Gly Ser Gly
1               5                   10                  15

Thr Asp Phe Thr Leu Thr Ile Ser Arg Leu Glu Pro Glu Asp Phe Ala
            20                  25                  30

Val Tyr Tyr
        35

<210> SEQ ID NO 183
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Cys Gln Gln Tyr Asp Arg Ser Tyr Tyr Tyr Thr Phe
1               5                   10

<210> SEQ ID NO 184
<211> LENGTH: 9
<212> TYPE: PRT
<213> ORGANISM: Artificial Sequence
```

<220> FEATURE:
<223> OTHER INFORMATION: Description of Artificial Sequence: Synthetic
      peptide

<400> SEQUENCE: 184

Gly Gln Gly Thr Lys Leu Glu Ile Lys
1               5

<210> SEQ ID NO 185
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 185
caggtgcagc tgcaggagtc gggcccagga ctggtgaagc cttcggagaa cctgtcgctc      60
acctgcactg tctctgatgc ctccatgagt gattatcact ggagctggat ccggcaggcc     120
gccgggaagg gactggagtg gattgggcgt atgtacagca ctgggagtcc ctactacaaa     180
ccctccctca aggtcgggt caccatgtca atagacacgt ccaagaacca gttctccctg      240
aagctggcct ctgtgaccgc cgcagacacg gccatctatt attgtgcgag cggacaacat     300
attggtggct gggtcccccc tgacttctgg ggccagggaa ccctggtcac cgtctcctca     360

<210> SEQ ID NO 186
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Gln Val Gln Leu Gln Glu Ser Gly Pro Gly Leu Val Lys Pro Ser Glu
1               5                   10                  15

Asn Leu Ser Leu Thr Cys Thr Val Ser Asp Ala Ser Met Ser Asp Tyr
            20                  25                  30

His Trp Ser Trp Ile Arg Gln Ala Ala Gly Lys Gly Leu Glu Trp Ile
        35                  40                  45

Gly Arg Met Tyr Ser Thr Gly Ser Pro Tyr Tyr Lys Pro Ser Leu Lys
    50                  55                  60

Gly Arg Val Thr Met Ser Ile Asp Thr Ser Lys Asn Gln Phe Ser Leu
65                  70                  75                  80

Lys Leu Ala Ser Val Thr Ala Ala Asp Thr Ala Ile Tyr Tyr Cys Ala
                85                  90                  95

Ser Gly Gln His Ile Gly Gly Trp Val Pro Pro Asp Phe Trp Gly Gln
            100                 105                 110

Gly Thr Leu Val Thr Val Ser Ser
        115                 120

<210> SEQ ID NO 187
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 187
gatattgtga tgacccagac tccactctcc tcacctgtca cccttggaca gccggcctcc      60

```
atctcctgca ggtctagtga aggcctcgta tatagtgatg agacaccta cttgagttgg    120 tttcaccaga ggccaggcca gcctccaaga ctcctgattt ataaaatttc taaccggttc    180
tctggggtcc ccgacagatt cagtggcagt ggggcaggca cagatttcac actgaaaatc    240
agcagggtgg aggctgagga tgtcgggggtt tattactgca tgcaagctac acattttccg    300
tggacgttcg gccaggggac caaagtggaa gtcaaacgt                           339
```

<210> SEQ ID NO 188
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide <400> SEQUENCE: 188

```
Asp Ile Val Met Thr Gln Thr Pro Leu Ser Ser Pro Val Thr Leu Gly
1               5                   10                  15

Gln Pro Ala Ser Ile Ser Cys Arg Ser Ser Glu Gly Leu Val Tyr Ser
            20                  25                  30

Asp Gly Asp Thr Tyr Leu Ser Trp Phe His Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr His Phe Pro Trp Thr Phe Gly Gln Gly Thr Lys Val Glu Val Lys
            100                 105                 110

Arg
```

<210> SEQ ID NO 189
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide <400> SEQUENCE: 189

```
Gln Val Gln Leu Gln Glu Ser Gly Pro Gly Leu Val Lys Pro Ser Glu
1               5                   10                  15

Asn Leu Ser Leu Thr Cys Thr Val Ser
            20                  25
```

<210> SEQ ID NO 190
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide <400> SEQUENCE: 190

```
Asp Ala Ser Met Ser Asp Tyr His
1               5
```

<210> SEQ ID NO 191
<211> LENGTH: 17

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Trp Ser Trp Ile Arg Gln Ala Ala Gly Lys Gly Leu Glu Trp Ile Gly
1               5                   10                  15

Arg

<210> SEQ ID NO 192
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Met Tyr Ser Thr Gly Ser Pro
1               5

<210> SEQ ID NO 193
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

Tyr Tyr Lys Pro Ser Leu Lys Gly Arg Val Thr Met Ser Ile Asp Thr
1               5                   10                  15

Ser Lys Asn Gln Phe Ser Leu Lys Leu Ala Ser Val Thr Ala Ala Asp
            20                  25                  30

Thr Ala Ile Tyr Tyr
        35

<210> SEQ ID NO 194
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Cys Ala Ser Gly Gln His Ile Gly Gly Trp Val Pro Pro Asp Phe Trp
1               5                   10                  15

<210> SEQ ID NO 195
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Gly Gln Gly Thr Leu Val Thr Val Ser Ser
1               5                   10

<210> SEQ ID NO 196
<211> LENGTH: 26
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 196

Asp Ile Val Met Thr Gln Thr Pro Leu Ser Ser Pro Val Thr Leu Gly
1               5                   10                  15
Gln Pro Ala Ser Ile Ser Cys Arg Ser Ser
            20                  25

<210> SEQ ID NO 197
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Glu Gly Leu Val Tyr Ser Asp Gly Asp Thr Tyr
1               5                   10

<210> SEQ ID NO 198
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Leu Ser Trp Phe His Gln Arg Pro Gly Gln Pro Pro Arg Leu Leu Ile
1               5                   10                  15
Tyr

<210> SEQ ID NO 199
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Lys Ile Ser
1

<210> SEQ ID NO 200
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

Asn Arg Phe Ser Gly Val Pro Asp Arg Phe Ser Gly Ser Gly Ala Gly
1               5                   10                  15
Thr Asp Phe Thr Leu Lys Ile Ser Arg Val Glu Ala Glu Asp Val Gly
            20                  25                  30
Val Tyr Tyr
        35

<210> SEQ ID NO 201

<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Cys Met Gln Ala Thr His Phe Pro Trp Thr Phe
1               5                   10

<210> SEQ ID NO 202
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Gly Gln Gly Thr Lys Val Glu Val Lys Arg
1               5                   10

<210> SEQ ID NO 203
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 203
gaggtgcagc tgttggagtc tgggggaggc ttggtacagc ctggggggtc cctgagactc      60
tcctgtgcag cctctggatt cacctttagt tcatatggct tgacctggat acgccaggct    120
ccggggaagg gcctggagtg ggtctcaagt atcagtggca gtggcaataa cacatactac    180
gcagactctg tgaagggccg gttcaccatc tccagagaca agtcaagaa gacactatat    240 ctacaaatgg acagcctgac agtcggagac acggccgtct attactgctt aggagtcggt    300
cagggccacg gaattccggt catcgtctcc tca                                  333

<210> SEQ ID NO 204
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 204

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Leu Thr Trp Ile Arg Gln Ala Pro Gly Lys Gly Leu Glu Trp Val
        35                  40                  45

Ser Ser Ile Ser Gly Ser Gly Asn Asn Thr Tyr Tyr Ala Asp Ser Val
    50                  55                  60

Lys Gly Arg Phe Thr Ile Ser Arg Asp Lys Val Lys Lys Thr Leu Tyr
65                  70                  75                  80

Leu Gln Met Asp Ser Leu Thr Val Gly Asp Thr Ala Val Tyr Tyr Cys
                85                  90                  95

Leu Gly Val Gly Gln Gly His Gly Ile Pro Val Ile Val Ser Ser

<210> SEQ ID NO 205
<211> LENGTH: 336
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 205

```
gatattgtga tgacccagac tccactctcc tcacctgtca cccttggaca gccggcctcc      60
atctcctgca ggtctagtca gagcctcgta caccgtgatg aaacacccta cttgagttgg     120
tttctgcaga ggccaggcca ggctccaaga ctcctaattt atcggatttc taaccggttc     180
tctggggtcc cagacagatt cagtggcagt ggggcaggga cggatttcac actgaaaatc     240
agcagggtgg aagctgagga tgtcggcgtt tactactgca tgcaagctac acaaatcccc     300
aacacttttg gccaggggac caagctggag atcaag                                336
```

<210> SEQ ID NO 206
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 206

Asp Ile Val Met Thr Gln Thr Pro Leu Ser Ser Pro Val Thr Leu Gly
1               5                   10                  15
Gln Pro Ala Ser Ile Ser Cys Arg Ser Ser Gln Ser Leu Val His Arg
            20                  25                  30
Asp Gly Asn Thr Tyr Leu Ser Trp Phe Leu Gln Arg Pro Gly Gln Ala
        35                  40                  45
Pro Arg Leu Leu Ile Tyr Arg Ile Ser Asn Arg Phe Ser Gly Val Pro
    50                  55                  60
Asp Arg Phe Ser Gly Ser Gly Ala Gly Thr Asp Phe Thr Leu Lys Ile
65                  70                  75                  80
Ser Arg Val Glu Ala Glu Asp Val Gly Val Tyr Tyr Cys Met Gln Ala
                85                  90                  95
Thr Gln Ile Pro Asn Thr Phe Gly Gln Gly Thr Lys Leu Glu Ile Lys
            100                 105                 110

<210> SEQ ID NO 207
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 207

Glu Val Gln Leu Leu Glu Ser Gly Gly Gly Leu Val Gln Pro Gly Gly
1               5                   10                  15
Ser Leu Arg Leu Ser Cys Ala Ala Ser
            20                  25

<210> SEQ ID NO 208
<211> LENGTH: 8
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 208

Gly Phe Thr Phe Ser Ser Tyr Gly
1               5

<210> SEQ ID NO 209
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Leu Thr Trp Ile Arg Gln Ala Pro Gly Lys Gly Leu Glu Trp Val Ser
1               5                   10                  15

Ser

<210> SEQ ID NO 210
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Ile Ser Gly Ser Gly Asn Asn Thr
1               5

<210> SEQ ID NO 211
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 211

Tyr Tyr Ala Asp Ser Val Lys Gly Arg Phe Thr Ile Ser Arg Asp Lys
1               5                   10                  15

Val Lys Lys Thr Leu Tyr Leu Gln Met Asp Ser Leu Thr Val Gly Asp
            20                  25                  30

Thr Ala Val Tyr Tyr
        35

<210> SEQ ID NO 212
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Cys Leu Gly Val Gly Gln
1               5

<210> SEQ ID NO 213
<211> LENGTH: 10
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 213

Gly His Gly Ile Pro Val Ile Val Ser Ser
1               5                   10

<210> SEQ ID NO 214
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Asp Ile Val Met Thr Gln Thr Pro Leu Ser Ser Pro Val Thr Leu Gly
1               5                   10                  15

Gln Pro Ala Ser Ile Ser Cys Arg Ser Ser
            20                  25

<210> SEQ ID NO 215
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Gln Ser Leu Val His Arg Asp Gly Asn Thr Tyr
1               5                   10

<210> SEQ ID NO 216
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Leu Ser Trp Phe Leu Gln Arg Pro Gly Gln Ala Pro Arg Leu Leu Ile
1               5                   10                  15

Tyr

<210> SEQ ID NO 217
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Arg Ile Ser
1

<210> SEQ ID NO 218
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 218

-continued

```
Asn Arg Phe Ser Gly Val Pro Asp Arg Phe Ser Gly Ser Gly Ala Gly
1               5                   10                  15

Thr Asp Phe Thr Leu Lys Ile Ser Arg Val Glu Ala Glu Asp Val Gly
            20                  25                  30

Val Tyr Tyr
        35

<210> SEQ ID NO 219
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Cys Met Gln Ala Thr Gln Ile Pro Asn Thr Phe
1               5                   10

<210> SEQ ID NO 220
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Gly Gln Gly Thr Lys Leu Glu Ile Lys
1               5

<210> SEQ ID NO 221
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 221
gaggtgcagc tggtggagtc tgaggaggc ttaatccagc cggggggtc cctaagactc        60 tcctgtgcag cctcgggctt cctcatcagt agttatttca tgagctgggt ccgccaggct      120
ccagggaagg ggccggagtg ggtctcagtt atttatagcg atggtagtac atattacgta      180
gactccgtga agggccgatt caccatctcc acagacaatt ccaagaacac actatatctt      240
cagatgaaca gcctgagagc cgaggacacg gcccgatatt actgtgcgac acggcatttg      300
aattatgacg gtgaccactg gggccaggga accctggtca ccgtctcctc agcctccacc      360
aag                                                                   363

<210> SEQ ID NO 222
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 222

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Leu Ile Ser Ser Tyr
            20                  25                  30
```

Phe Met Ser Trp Val Arg Gln Ala Pro Gly Lys Gly Pro Glu Trp Val
            35                  40                  45

Ser Val Ile Tyr Ser Asp Gly Ser Thr Tyr Tyr Val Asp Ser Val Lys
 50                  55                  60

Gly Arg Phe Thr Ile Ser Thr Asp Asn Ser Lys Asn Thr Leu Tyr Leu
 65                  70                  75                  80

Gln Met Asn Ser Leu Arg Ala Glu Asp Thr Ala Arg Tyr Tyr Cys Ala
                 85                  90                  95

Thr Arg His Leu Asn Tyr Asp Gly Asp His Trp Gly Gln Gly Thr Leu
             100                 105                 110

Val Thr Val Ser Ser Ala Ser Thr Lys
            115                 120

<210> SEQ ID NO 223
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 223
gatgttgtga tgactcagtc tccactctcc ctgcccgtca cccttggaca gccggcctcc      60
atctcctgca ggtctagtca agcctcgta cacagtgacg aaacaccta cttgaattgg      120 tttcaccaga ggccaggcca atctccaagg cgcctaattt ataaggtttc taagcgggac      180 tctgggggtcc cagacagatt cagcggcagt gggtcaggta gtgatttcac actgaaaatc      240
agcagggtgg aggctgagga tgttggaatt tattactgca tgcaaggtac acattggccg      300
acgttcggcc aagggaccaa ggtggaaatc aaacgaactg tggctgca                  348

<210> SEQ ID NO 224
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 224

Asp Val Val Met Thr Gln Ser Pro Leu Ser Leu Pro Val Thr Leu Gly
  1               5                  10                  15

Gln Pro Ala Ser Ile Ser Cys Arg Ser Ser Gln Ser Leu Val His Ser
                 20                  25                  30

Asp Gly Asn Thr Tyr Leu Asn Trp Phe His Gln Arg Pro Gly Gln Ser
             35                  40                  45

Pro Arg Arg Leu Ile Tyr Lys Val Ser Lys Arg Asp Ser Gly Val Pro
 50                  55                  60

Asp Arg Phe Ser Gly Ser Gly Ser Gly Ser Asp Phe Thr Leu Lys Ile
 65                  70                  75                  80

Ser Arg Val Glu Ala Glu Asp Val Gly Ile Tyr Tyr Cys Met Gln Gly
                 85                  90                  95

Thr His Trp Pro Thr Phe Gly Gln Gly Thr Lys Val Glu Ile Lys Arg
             100                 105                 110

Thr Val Ala Ala
        115

<210> SEQ ID NO 225

```
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Glu Val Gln Leu Val Glu Ser Gly Gly Gly Leu Ile Gln Pro Gly Gly
1               5                   10                  15

Ser Leu Arg Leu Ser Cys Ala Ala Ser
            20                  25

<210> SEQ ID NO 226
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Gly Phe Leu Ile Ser Ser Tyr Phe
1               5

<210> SEQ ID NO 227
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Met Ser Trp Val Arg Gln Ala Pro Gly Lys Gly Pro Glu Trp Val Ser
1               5                   10                  15

Val

<210> SEQ ID NO 228
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Ile Tyr Ser Asp Gly Ser Thr
1               5

<210> SEQ ID NO 229
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 229

Tyr Tyr Val Asp Ser Val Lys Gly Arg Phe Thr Ile Ser Thr Asp Asn
1               5                   10                  15

Ser Lys Asn Thr Leu Tyr Leu Gln Met Asn Ser Leu Arg Ala Glu Asp
            20                  25                  30

Thr Ala Arg Tyr Tyr
            35
```

```
<210> SEQ ID NO 230
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Cys Ala Thr Arg His Leu Asn Tyr Asp Gly Asp His Trp
1               5                   10

<210> SEQ ID NO 231
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Asp Val Val Met Thr Gln Ser Pro Leu Ser Leu Pro Val Thr Leu Gly
1               5                   10                  15

Gln Pro Ala Ser Ile Ser Cys Arg Ser Ser
            20                  25

<210> SEQ ID NO 232
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Gln Ser Leu Val His Ser Asp Gly Asn Thr Tyr
1               5                   10

<210> SEQ ID NO 233
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Leu Asn Trp Phe His Gln Arg Pro Gly Gln Ser Pro Arg Arg Leu Ile
1               5                   10                  15

Tyr

<210> SEQ ID NO 234
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Lys Val Ser
1

<210> SEQ ID NO 235
<211> LENGTH: 35
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 235

Lys Arg Asp Ser Gly Val Pro Asp Arg Phe Ser Gly Ser Gly Ser Gly
1               5                   10                  15

Ser Asp Phe Thr Leu Lys Ile Ser Arg Val Glu Ala Glu Asp Val Gly
            20                  25                  30

Ile Tyr Tyr
        35

<210> SEQ ID NO 236
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Cys Met Gln Gly Thr His Trp Pro Thr Phe
1               5                   10

<210> SEQ ID NO 237
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Gly Gln Gly Thr Lys Val Glu Ile Lys Arg Thr Val Ala Ala
1               5                   10

<210> SEQ ID NO 238
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Gly Leu Asn Asp Ile Phe Glu Ala Gln Lys Ile Glu Trp His Glu
1               5                   10                  15
```